(12) United States Patent
Spevak et al.

(10) Patent No.: US 7,863,289 B2
(45) Date of Patent: *Jan. 4, 2011

(54) COMPOUNDS AND METHODS FOR KINASE MODULATION, AND INDICATIONS THEREFOR

(75) Inventors: Wayne Spevak, Berkeley, CA (US); Hanna Cho, Oakland, CA (US); Prabha N. Ibrahim, Mountain View, CA (US); Shenghua Shi, San Diego, CA (US); Shumeye Mamo, Oakland, CA (US); Samuel J. Gillette, Oakland, CA (US); Hongyao Zhu, Berkeley, CA (US)

(73) Assignee: Plexxikon, Inc., Berkeley, CA (US)

( * ) Notice: Subject to any disclaimer, the term of this patent is extended or adjusted under 35 U.S.C. 154(b) by 356 days.

This patent is subject to a terminal disclaimer.

(21) Appl. No.: 11/960,590

(22) Filed: Dec. 19, 2007

(65) Prior Publication Data

US 2008/0167338 A1 Jul. 10, 2008

Related U.S. Application Data

(60) Provisional application No. 60/876,953, filed on Dec. 21, 2006.

(51) Int. Cl.
*A61K 31/437* (2006.01)
*C07D 487/04* (2006.01)
*A61P 25/00* (2006.01)
*A61P 29/00* (2006.01)
*A61P 35/04* (2006.01)

(52) U.S. Cl. ..................... 514/300; 546/113
(58) Field of Classification Search ............ 514/300; 546/113

See application file for complete search history.

(56) References Cited

U.S. PATENT DOCUMENTS

| | | |
|---|---|---|
| 2,234,705 A | 3/1941 | Normington et al. |
| 2,413,258 A | 12/1946 | Soday et al. |
| 4,150,949 A | 4/1979 | Smith |
| 4,568,649 A | 2/1986 | Bertoglio-Matte |
| 4,626,513 A | 12/1986 | Burton et al. |
| 4,727,395 A | 2/1988 | Oda et al. |
| 5,120,782 A | 6/1992 | Hubsch et al. |
| 5,143,854 A | 9/1992 | Pirrung et al. |
| 5,338,849 A | 8/1994 | Festal et al. |
| 5,426,039 A | 6/1995 | Wallace et al. |
| 5,432,177 A | 7/1995 | Baker et al. |
| 5,434,049 A | 7/1995 | Okano et al. |
| 5,449,614 A | 9/1995 | Danos et al. |
| 5,474,935 A | 12/1995 | Chatterjee et al. |
| 5,556,752 A | 9/1996 | Lockhart et al. |
| 5,576,319 A | 11/1996 | Baker et al. |
| 5,580,859 A | 12/1996 | Felgner et al. |
| 5,631,236 A | 5/1997 | Woo et al. |
| 5,632,957 A | 5/1997 | Heller et al. |
| 5,658,775 A | 8/1997 | Gilboa |
| 5,681,959 A | 10/1997 | Bishop et al. |
| 5,700,637 A | 12/1997 | Southern |
| 5,700,809 A | 12/1997 | Leeson et al. |
| 5,712,285 A | 1/1998 | Curtis et al. |
| 5,721,118 A | 2/1998 | Scheffler |
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,877,007 A | 3/1999 | Housey |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |
| 6,110,456 A | 8/2000 | During |
| 6,110,458 A | 8/2000 | Freeman et al. |

(Continued)

FOREIGN PATENT DOCUMENTS

DE 24 13 258 A1 10/1975

(Continued)

OTHER PUBLICATIONS

Alfthan, K., Surface Plasmon Resonance Biosensors as a Tool in Antibody Engineering, Biosensors & Bioelectronics 13:653-663 (1998).

(Continued)

*Primary Examiner*—D. Margaret Seaman
*Assistant Examiner*—Niloofar Rahmani
(74) *Attorney, Agent, or Firm*—Foley & Lardner LLP

(57) ABSTRACT

Compounds active on protein kinases are described, as well as methods of using such compounds to treat diseases and conditions associated with aberrant activity of protein kinases.

24 Claims, No Drawings

U.S. PATENT DOCUMENTS

| | | |
|---|---|---|
| 6,113,913 A | 9/2000 | Brough et al. |
| 6,117,681 A | 9/2000 | Salmons et al. |
| 6,161,776 A | 12/2000 | Byles |
| 6,178,384 B1 | 1/2001 | Kolossvary |
| 6,235,769 B1 | 5/2001 | Clary |
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,288,234 B1 | 9/2001 | Griffin |
| 6,294,330 B1 | 9/2001 | Michnick et al. |
| 6,310,074 B1 | 10/2001 | Depreux et al. |
| 6,545,014 B2 | 4/2003 | Verner |
| 6,858,860 B2 | 2/2005 | Hosono et al. |
| 7,259,165 B2 | 8/2007 | Bernotas et al. |
| 7,361,763 B2 | 4/2008 | Arnold et al. |
| 7,361,764 B2 | 4/2008 | Arnold et al. |
| 7,452,993 B2 | 11/2008 | Arnold et al. |
| 7,498,342 B2 | 3/2009 | Ibrahim et al. |
| 7,504,509 B2 | 3/2009 | Ibrahim et al. |
| 7,582,637 B2 | 9/2009 | Arnold et al. |
| 7,601,839 B2 | 10/2009 | Arnold et al. |
| 7,626,021 B2 | 12/2009 | Arnold et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2003/0003004 A1 | 1/2003 | Stones et al. |
| 2004/0002534 A1 | 1/2004 | Lipson et al. |
| 2004/0022534 A1 | 2/2004 | Amano et al. |
| 2004/0077595 A1 | 4/2004 | Cheng et al. |
| 2004/0142864 A1 | 7/2004 | Bremer et al. |
| 2004/0167030 A1 | 8/2004 | Bernotas et al. |
| 2005/0085463 A1 | 4/2005 | Weiner et al. |
| 2005/0154014 A1 | 7/2005 | Bloxham et al. |
| 2005/0164300 A1 | 7/2005 | Artis et al. |
| 2005/0170431 A1 | 8/2005 | Ibrahim et al. |
| 2005/0256151 A1 | 11/2005 | Salom et al. |
| 2006/0035898 A1 | 2/2006 | Arnold et al. |
| 2006/0058339 A1 | 3/2006 | Ibrahim et al. |
| 2006/0058340 A1 | 3/2006 | Ibrahim et al. |
| 2007/0032519 A1 | 2/2007 | Zhang et al. |
| 2007/0049615 A1 | 3/2007 | Ibrahim et al. |
| 2007/0287711 A1 | 12/2007 | Arnold et al. |
| 2008/0167338 A1 | 7/2008 | Spevak et al. |
| 2008/0188514 A1 | 8/2008 | Wu et al. |
| 2009/0005356 A1 | 1/2009 | Blaney et al. |
| 2009/0143352 A1 | 6/2009 | Arnold et al. |
| 2009/0306056 A1 | 12/2009 | Arnold et al. |

FOREIGN PATENT DOCUMENTS

| | | |
|---|---|---|
| EP | 0 154 734 | 8/1990 |
| EP | 0 465 970 | 1/1992 |
| EP | 1 057 826 | 12/2000 |
| EP | 0 870 768 | 5/2002 |
| EP | 1 267 111 | 12/2002 |
| EP | 1 749 829 | 2/2007 |
| GB | 2 292 143 | 2/1996 |
| GB | 2 292 145 | 2/1996 |
| GB | 2 298 198 | 8/1996 |
| GB | 2 299 581 | 10/1996 |
| JP | 06-135946 | 5/1994 |
| JP | 10-130269 | 5/1998 |
| JP | 15-073357 | 3/2003 |
| WO | WO-93/13099 | 7/1993 |
| WO | WO-94/14808 | 7/1994 |
| WO | WO-94/20459 | 9/1994 |
| WO | WO-94/20497 | 9/1994 |
| WO | WO-95/04742 | 2/1995 |
| WO | WO-95/07910 | 3/1995 |
| WO | WO-95/28387 | 10/1995 |
| WO | WO-96/00226 | 1/1996 |
| WO | WO-96/11929 | 2/1996 |
| WO | WO-96/05200 | 4/1996 |
| WO | WO-96/17958 | 6/1996 |
| WO | WO-96/18738 | 6/1996 |
| WO | WO-97/46313 | 12/1997 |
| WO | WO-97/46558 | 12/1997 |
| WO | WO-97/49703 | 12/1997 |
| WO | WO-98/06433 | 2/1998 |
| WO | WO-98/22457 | 5/1998 |
| WO | WO-98/47899 | 10/1998 |
| WO | WO-99/00386 | 1/1999 |
| WO | WO-99/09217 | 2/1999 |
| WO | WO-99/51231 | 10/1999 |
| WO | WO-99/51232 | 10/1999 |
| WO | WO-99/51233 | 10/1999 |
| WO | WO-99/51234 | 10/1999 |
| WO | WO-99/51595 | 10/1999 |
| WO | WO-99/51596 | 10/1999 |
| WO | WO 99/51773 | 10/1999 |
| WO | WO-00/09162 | 2/2000 |
| WO | WO-00/12074 | 3/2000 |
| WO | WO-00/12514 | 3/2000 |
| WO | WO-00/29411 | 5/2000 |
| WO | WO-00/53582 | 9/2000 |
| WO | WO-00/64898 | 11/2000 |
| WO | WO-00/71537 | 11/2000 |
| WO | WO-00/75139 | 12/2000 |
| WO | WO-01/09121 | 2/2001 |
| WO | WO-01/24236 | 4/2001 |
| WO | WO-01/29036 | 4/2001 |
| WO | WO-01/46196 | 6/2001 |
| WO | WO-01/60822 | 8/2001 |
| WO | WO-01/62255 | 8/2001 |
| WO | WO-01/98299 | 12/2001 |
| WO | WO-02/00657 | 1/2002 |
| WO | WO-02/18346 | 3/2002 |
| WO | WO-02/083175 | 10/2002 |
| WO | WO-02/085896 | 10/2002 |
| WO | WO-02/102783 | 12/2002 |
| WO | WO-03/000258 | 1/2003 |
| WO | WO-03/003004 A2 | 1/2003 |
| WO | WO-03/006459 | 1/2003 |
| WO | WO-03/008422 | 1/2003 |
| WO | WO-03/011868 | 2/2003 |
| WO | WO-03/020698 | 3/2003 |
| WO | WO-03/028724 | 4/2003 |
| WO | WO-03/037862 | 5/2003 |
| WO | WO-03/051838 | 6/2003 |
| WO | WO-03/064413 | 8/2003 |
| WO | WO-03/068221 | 8/2003 |
| WO | WO-03/082289 | 10/2003 |
| WO | WO-03/082868 | 10/2003 |
| WO | WO-03/082869 | 10/2003 |
| WO | WO-03/087087 | 10/2003 |
| WO | WO-03/101990 | 12/2003 |
| WO | WO-2004/009600 | 1/2004 |
| WO | WO-2004/009601 | 1/2004 |
| WO | WO-2004/016609 | 2/2004 |
| WO | WO-2004/016610 | 2/2004 |
| WO | WO-2004/024895 | 3/2004 |
| WO | WO-2004/065393 | 8/2004 |
| WO | WO-2004/065394 | 8/2004 |
| WO | WO-2004/074286 | 9/2004 |
| WO | WO-2004/078756 | 9/2004 |
| WO | WO-2004/078923 | 9/2004 |
| WO | WO-2004/101565 | 11/2004 |
| WO | WO-2005/028475 | 3/2005 |

| | | |
|---|---|---|
| WO | WO-2005/028624 | 3/2005 |
| WO | WO-2005/044181 | 5/2005 |
| WO | WO-2005/058891 | 6/2005 |
| WO | WO-2005/062795 | 7/2005 |
| WO | WO-2005/063746 | 7/2005 |
| WO | WO-2005/063747 | 7/2005 |
| WO | WO-2005/082367 | 9/2005 |
| WO | WO-2005/085244 | 9/2005 |
| WO | WO-2005/095400 | 10/2005 |
| WO | WO-2005/103050 | 11/2005 |
| WO | WO-2005/115363 | 12/2005 |
| WO | WO-2006/004984 | 1/2006 |
| WO | WO 2006/009755 | 1/2006 |
| WO | WO-2006/009797 | 1/2006 |
| WO | WO 2006/015123 | 2/2006 |
| WO | WO-2006/015124 | 2/2006 |
| WO | WO-2006/114180 | 11/2006 |
| WO | WO-2006/127587 | 11/2006 |
| WO | 2007002325 * | 1/2007 |
| WO | WO 2007/002325 | 1/2007 |
| WO | WO 2007/002433 | 1/2007 |
| WO | WO-2007/013896 | 2/2007 |
| WO | WO-2007/106236 | 9/2007 |

OTHER PUBLICATIONS

Allegretti, et al., Palladium-Catalysed Functionalisation at 4- and 6-Position of the 7-Azaindole System, Synlett 5:609-612 (2001).

Al-Obeidi, et al., Peptide and Peptidomimetic Libraries, Mol Biotechnol 9:205-223, 1998.

Alvarez, et al., Synthesis of 3-Aryl- and 3-Heteroaryl-7-Azaindoles, Synthesis 4:615-620 (1999).

Amersdorfer and Marks, Phage Libraries for Generation of Anti-Botulinum scFv Antibodies, Methods in Molecular Biology 145:219-240, 2000.

Anderson, et al., Cooperative Catalyst Effects in Palladium-Mediated Cyanation Reactions of Aryl Halides and Triflates, J. Org. Chem. 63:8224-8228 (1998).

Antonini, et al., Synthesis of 4-Amino-1-β-D-Ribofuranosyl-1H-pyrrolo[2,3-b]pyridine (1-Deazatubercidin) as a Potential Antitumor Agent, J. Med. Chem. 25:1258-1261 (1982).

Ashman et al., The biology of stem cell factor and its receptor C-kit, The International Journal of Biochemistry & Cell Biology, 31:1037-1051, 1999.

Baghestanian, et al., A Case of Malignant Mastocytosis with Circulating Mast Cell Precursors: Biologic and Phenotypic Characterization of the Malignant Clone, Leuk. 10:159-166 (1996).

Bagshawe, Antibody-Directed Enzyme Prodrug Therapy: A Review; 1995, Drug Dev. Res., 34:220-230.

Balak, et. al., Novel D761Y and common secondary T790M mutations in epidermal growth factor receptor-mutant lung adenocarcinomas with acquired resistance to kinase inhibitors. Clin. Cancer Res. 12:6494-501 (2006).

Bancalari, et al., Blood Markers of Early and Late Airway Responses to Allergen in Asthmatic Subjects. Relationship with Functional Findings Allergy 52:32-40, 1997.

Bartlett, et al., CAVEAT: A Program to Facilitate the Structure-Derived Design of Biologically Active Molecules Royal Society of Chemistry 78:180-196, 1989.

Barton et al, The chemistry of pentavalent organobismuth reagants. Part X. Studies on the phenylation and oxidation of phenols, Tetrahedron, vol. 43, No. 2, 1987, pp. 323-332.

Bashford and Harris, Measurement of Ligand Binding to Proteins, Spectrophotometry and Spectrofluorimetry: A Practical Approach 4:91-113 (1987).

Basta et al, High-dose Intravenous Immunoglobulin Exerts Its Beneficial Effect in Patients with Dermatomyositis by Blocking Endomysial Deposition of Activated Complement Fragments; J Clin Invest 1994, 94:1729-1735.

Bedi, et al., BCR-ABL-Mediated Inhibition of Apoptosis With Delay of G2/M Transition After DNA Damage: A Mechanism of Resistance to Multiple Anticancer Agents; Blood 1995, 86:1148-1158.

Bell, (1981) Spectroscopy in Biochemistry, vol. I, pp. 155-194, CRC Press.

Bellone, et al., Growth Stimulation of Colorectal Carcinoma Cells Via the c-Kit Receptor is Inhibited by TGF-β1, Cell Physiol. 172:1-11 (1997).

Berdel, et al., Recombinant Human Stem Cell Factor Stimulates Growth of a Human Glioblastoma Cell c-kit Protooncogene, Canc. Res. 52:3498-3502 (1992).

Bertolini et al., A new Rational Hypothesis for the Pharmacophore of the Active Metabolite of Leflunomide, A Potent Immunosuppressive Drug; 1997, J. Med. Chem., 40:2011-2016.

Bjorntorp, Neuroendocrine Pertuirbations as a Cause of Insulin Resistance; Diabetes Metab. Res. Rev., 1999, 15: 427-441.

Bloom, A. and Day. A.R., The Preparation of 2-Alkylaminobenzimidazoles, J. Org. Chem. 14, 17 (1939).

Blundell et al., Knowledge-Based Protein Modelling and Design Eur. J. Biochem. 172:513-520 1988.

Böhm, H., On the Use of LUDI to Search the Fine Chemicals Directory for Ligands of Proteins of Known Three-Dimensional Structure, J. Comp. Aided Molec. Design 8:623-632, 1994.

Bokenmeyer, et al., Expression of Stem-Cell Factor and Its Receptor c-kit Protein in Normal Testicular Tissue and Malignant Germ-Cell Tumours, J. Cancer Res. Clin. Oncol. 122:301-306 (1996).

Bolger et al, Computer Modeling of Combining Site Structure of Anti-Hapten Monoclonal Antibodies, Methods Enz., 203:21-45, 1991.

Bongarzone, et al., High Frequency of Activation of Tyrosine Kinase Oncogenes in Human Papillary Thyroid Carcinoma, Oncogene 4(12):1457-1462 (1989).

Bothwell, M., Keeping Track of Neurotrophin Receptors Cell, 65:915-918, 1991.

Bowtell, D., Options Available From Start to Finish for Obtaining Expression Data by Microarray, Nature Genetics Supp. 21:25-32 (1999).

Brenner et al., Encoded Combinatorial Chemistry, Proc. Natl. Acad. Sci. USA 89:5381-5383, 1992.

Broudy, V., Stem Cell Factor and Hematopoiesis, Blood 90:1345-1364 (1997).

Brünger, A., Free R Value: a Novel Statistical Quantity for Assessing the Accuracy of Crystal Structures Nature 355:472-475 (1992).

Buchschacher, Human Immunodeficiency Virus Vectors for Inducible Expression of Foreign Genes; (1992) J. Virol. 66:2731-2739.

Capon, et al., Designing CD4 Immunoadhesins for AIDS Therapy, Nature 337:525-531 (1989).

Carell et al., New Promise in Combinatorial Chemistry: Synthesis, Characterization, and Screening of Small-Molecule Libraries in Solution, Chem. Biol. 2:171-183 (1995).

Carpino, et al., p62dok: A Constitutively Tyrosine-Phosphorylated, GAP-Associated Protein in Chronic Myelogenous Leukemia Progenitor Cells; Cell 1997, 88:197-204.

Castells, et al., The Presence of Membrane-Bound Stem Cell Factor on Highly Immature Nonmetachromatic Mast Cells in the Peripheral Blood of a Patient with Aggressive Systemic Mastocytosis, J. Aller. Clin. Immunol. 98:831-840 (1996).

Chabala, J., Solid-Phase Combinatorial Chemistry and Novel Tagging Methods for Identifying Leads, Curr Opin Biotechnol 6:632-639 (1995).

Chayer, et al., Synthesis of Carboranylpyrroles, Tetrahedron Lett. 42(44):7759-7761 (2001).

Checovich, et al., Fluorescence Polarization—A New Tool for Cell and Molecular Biology, Nature 375:254-256 (1995).

Clark, et al., PRO_LIGAND: An Approach to De Novo Molecular Design. 1. Application to the Design of Organic Molecules, J. Comp. Aided Molec. Design 9:13-32 (1995).

Cohisy et al, Review of Cellular Mechanisms of Tumor Osteolysis; Clin. Orthop. 2000, 373: 104-14.

Coe, et al., Solution-Phase Combinatorial Chemistry, Mol Divers. 4:31-38 (1999).

Cohen, et al., Expression of Stem Cell Factor and C-Kit in Human Neuroblastoma; 1994, Blood 84:3465-3472.

Collioud et al., Oriented and Covalent Immobilization of Target Molecules to Solid Supports: Synthesis and Application of a Light-Activatable and Thiol-Reactive Cross-Linking Reagent; (1993) Bioconjugate Chem. 4:528-536.

Colman, P.M., Structure-Based Drug Design, Current Opinion in Struc. Biol. 4: 868-874 (1994).

Columbo, et al., The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils, J. Immunol 149:599-608 (1992).

Costa, et al., The Cells of the Allergic Response, JAMA 278:1815-1822 (1997).

Coste, et al., Coupling N-Methylated Amino Acids Using PyBroP1 and PyCloP Halogenophosphonium Salts: Mechanism and Fields of Application, Journal of Organic Chemistry 59:2437-2446 (1994).

Creighton, T., An Empirical Approach to Protein Conformation Stability and Flexibility, Biopolymers 22(1):49-58 (1983).

Crouch et al., The use of ATP bioluminescence as a measure of cell proliferation and cytotoxicity. Journal of Immunological Methods, 160:81-8 (1993).

Crump, M., Inhibition of Raf Kinase in the Treatment of Acute Myeloid Leukemia, Curr. Pharm. Design 8(25):2243-8 (2002).

Curtin et al., Discovery and Evaluation of a Series of 3-Acylindole Imidazopyridine Platelet-Activating Factor Antagonists, J. Med. Chem., vol. 41, 1998, pp. 74-95.

Cwirla et al., Peptides on Phage: A Vast Library of Peptides for Identifying Ligands, Biochemistry 87:6378-6382 (1990).

Dai et al., Targeted disruption of the mouse colony-stimulating factor 1 receptor gene results in osteopetrosis, mononuclear phagocyte deficiency, increased primitive progenitor cell frequencies, and reproductive defects; Blood, 2002, 99: 111-120.

Dandliker, et al., Equilibrium and Kinetic Inhibition Assays Based Upon Fluorescence Polarization, Methods in Enzymology 74:3-28 (1981).

Dastych, et al., Stem Cell Factor Induces Mast Cell Adhesion to Fibronectin; 1994, J. Immunol. 152:213-219.

Demetri, Targeting c-kit mutations in solid tumors: Scientific rationale and novel therapeutic options, Seminars in Oncology, 28(5), Supp. 17, 19-26, 2001.

Dewar et al., Inhibition of c-fms by Imatinib Expanding the Spectrum of Treatment; Cell Cycle 2005, 4(7):851-3.

Dobeli, H., et al., Recombinant Fusion Proteins for the Industrial Production of Disulfide Bridge containing Peptides: Purification, Oxidation without Cancatamer Formation, and Selective Cleavage; 1998 Protein Expr. Purif. 12:404-414.

Dolle et al., Comprehensive Survey of Combinatorial Library Synthesis: 1998, J Comb Chem 1:235-282 (1999).

Donis-Keller, et al., Mutations in the RET Proto-Oncogene are Associated with MEN 2A and FMTC, Hum Mol Genet. 2(7):851-856 (1993).

Doyle and Bryker, Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media; J. Org. Chem. 1979, 44:1572.

Dube and Scholte, Reductive N-Alkylation of Amides, Carbamates and Ureas, Tetrahedron Lett. 40:2295-2298 (1999).

Durbec, et al., GDNF Signalling Through the Ret Receptor Tyrosine Kinase, Nature 381:789-793 (1996).

Dyson, et al., The Human Papilloma Virus 13 16 E7 Oncoprotein is Able to Bind to the Retinoblastoma Gene Product, Science 243:934-937 (1989).

Eklund and Joensuu, Treatment of rheumatoid arthritis with imatinib mesylate: clinical improvements in three refractory cases, Annals of Medicine, 35:362-367, 2003.

Eliseev et al, Dynamic Combinatorial Chemistry: Evolutionary Formation and Screening of Molecular Libraries, Current Topics in Microbiology & Immunology 243:159-172 (1999).

Enjalbal, et al., Mass Spectrometry in Combinatorial Chemistry, Mass Spectrometry Reviews. 19:139-161 (2000).

Escribano, et al., Expression of the c-kit (CD117) Molecule in Normal and Malignant Hematopoiesis, Leuk. Lymph. 30:459-466 (1998).

Feng et al, Tyrosines 559 and 807 in the Cytoplasmic Tail of the Macrophage colony-Stimulating Factor Receptor Play Distinct Roles in Osteoclast Differentiation and Function; Endocrinology 2002, 143: 4868-74.

Feng, et al., Stable in Vivo Gene Transduction Via a Novel Adenoviral/Retroviral Chimeric Vector, Nature Biotechnology 15:866-870 (1997).

Finotto, et al., Glucocorticoids Disease Tissue Mast Cell Number by Reducing the Production of the c-kit Ligand, Stem Cell Factor, by Resident Cells, J. Clin. Invest. 99:1721-1728 (1997).

Fivash et al., BIAcore for macromolecular interaction; (1998) BIAcore for macromolecular interaction, Current Opinion in Biotechnology. 9:97-101.

Flanagan & Lader, Macrophages and the various isoforms of macrophage colony-stimulating factor; Curr Opin Hematol. 1998, 5:181-5.

Franz and Martin, Sulfuranes. X. A Reagent for the Facile Cleavage of Secondary Amides, JACS, 95(6):2017-2019 (1973).

Furitsu, et al., Identification of Mutations in the Coding Sequence of the Proto-oncogene c-kit in a Human Mast Cell Leukemia Cell Line Causing Ligand-independent Activation of the c-kit Product;1993, J. Clin Invest. 92:1736-1744.

Furuta, et al., Stem Cell Factor Influences Mast Cell Mediator Release in Response to Eosinophil-Derived Granule Major Basic Protein, Blood 92:1055-1061 (1998).

Gallop et al., Applications of Combinatorial Technologies to Drug Discovery. 1. Background and Peptide Combinatorial Libraries, J. Med. Chem. 37:1233-1251 (1994).

Gassman et al., Journal of the American Chemical Society, 95(13), pp. 4453-4455, (Jun. 27, 1973).

Girgis, N. et.al., The Synthesis of 5-Azaindoles by Substitution-Rearrangement of 7-Azaindoles upon Treatment with Certain Primary Amines; J. Heterocyclic. Chem. 1989, 26:317-325.

Golkar, et al., Mastocytosis, Lancet 349:1379-1385 (1997).

Goodford, P.J., A Computational Procedure for Determining Energetically Favorable Binding Sites on Biologically Important Macromolecules, J. Med. Chem. 28:849-857 (1985).

Goodsell et al, Automated Docking of Substrates to Proteins by Simulated Annealing, Proteins: Structure, Function, and Genetics 8:195-202 (1990).

Gordon et al., Applications of Combinatorial Technologies to Drug Discovery. 2. Combinatorial Organic Synthesis, Library Screening Strategies, and Future Directions, J. Med. Chem. 37:1384-1401 (1994).

Gordon, and Ford, Detection of Peroxides and Their Removal, The Chemist's Companion: A Handbook of Practical Data, Techniques, And ReferenceS p. 437 (1972).

Gram H., Phage Display in Proteolysis and Signal Transduction, Combinatorial Chemistry & High Throughput Screening 2:19-28 (1999).

Gravert et al, Synthesis on Soluble Polymers: New Reactions and the Construction of Small Molecules, Curr Opin Chem Biol 1:107-113 (1997).

Greer, J., Model Structure for the Inflammatory Protein C5a, Science 228:1055-1060 (1985).

Grieco, et al., PTC is a Novel Rearranged Form of the ret Proto-Oncogene and is Frequently Detected in Vivo in Human Thyroid Papillary Carcinomas, Cell 60(4):557-563 (1990).

Guida, W., Software for Structure-Based Drug Design, Current Opinion in Struc. Biol. 4:777-781 (1994).

Hafner, et al., Isothermal Amplification and Multimerization of DNA by Bst DNA Polymerase, Biotechniques 2001 Apr;30(4):852-867.

Hallek, et al., Interaction of the Receptor Tyrosine Kinase p145c-kit with the p210bcr/abl Kinase in Myeloid Cells, Brit. J Haem. 94:5-16 (1996).

Hamel, et al., The Road Less Traveled: c-kit and Stem Cell Factor, J. Neuro-Onc. 35:327-333 (1997).

Hands et. al., A convenient Method for the Preparation of 5-, 6- and 7-Azaindoles and Their Derivatives; Synthesis 1996, 877-882.

Hanselman, et al., A cDNA-Dependent Scintillation Proximity Assay for Quantifying Apolipoprotein A-1, J. Lipid Res. 38:2365-2373 (1997).

Hassan and Zander, Stem Cell Factor as a Survival and Growth Factor in Human Normal and Malignant Hematopoiesis, Acta. Hem. 95:257-262 (1996).
Hassan, et al., Expression of Protooncogene c-kit and Its Ligand Stem Cell Factor (SCF) in Gastric Carcinoma Cell Lines; 1998, Digest. Dis. Science 43:8-14.
Hayashi, et al., Dichloro[1,1 19-bis(diphenylophosphino)ferrocene]palladium-(II), An Effective Catalyst for Cross-Coupling of Secondary and Primary Alkyl Grignard and Alkylzinc Reagents with Organic Halides, J. Am. Chem. Soc. 106:158-163 (1984).
Heacock et al., Orientation and Relative Reaction rate Factors in aromatic Substitution by the Benzensulfonimido Radical, J. Am. Chem. Soc., vol. 82, 1960, pp. 3460-3463.
Heim, et al., Engineering Green Fluorescent Protein for Improved Brightness, Longer Wavelengths and Fluorescence Resonance Energy Transfer, Curr. Biol. 6:178-182 (1996).
Heinrich et al., PDGFRA Activating Mutations in Gastrointestinal Stromal Tumors; (Science 2003, 299:708-10).
Herbst, et al., Differential Effects of W Mutations on p145c-kit Tyrosine Kinase Activity and Substrate Interaction, J. Biol. Chem. 267:13210-13216 (1992).
Hibi, et al., Coexpression of the stem cell factor and the c-kit genes in small-cell lung cancer; 1991, Oncogene 6:2291-2296.
Hirota, et al., Gain-of-function Mutations of c-kit in Human Gastrointestinal Stromal Tumors; 1998, Science 279:577-580.
Hoffmann, m-Trifluoromethylbenzenesulfonyl Chloride, Organic Syntheses, Coll. vol. 60, p. 121-126, 1981.
Hogaboam, et al., Novel Role of Transmembrane SCF for Mast Cell Activation and Eotaxin Production in Mast Cell-Fibroblast Interactions, J. Immunol. 160:6166-6171 (1998).
Houghten, et al., Generation and Use of Synthetic Peptide Combinatorial Libraries for Basic Research and Drug Discovery, Nature 354:84-86 (1991).
Houghten, R., Parallel Array and Mixture-Based Synthetic Combinatorial Chemistry: Tools for the Next Millennium, Annu Rev Pharmacol Toxicol 40:273-282 (2000).
Houghten, R., Peptide Libraries: Criteria and Trends, Trends Genet. 9:235-239 (1993).
Hudson, P. B. et al., A Simple Method for the Determination of Serum Acid Phosphatase, Journal of Urology 58:89-92 (1947).
Hughes-Jones, et al., Synthesis of Rh Fv Phage-Antibodies Using VH and VL Germline Genes, British Journal of Haematology 105:811-816 (1999).
Iemura, et al., The c-kit Ligand, Stem Cell Factor, Promotes Mast Cell Survival by Suppressing Apoptosis, Amer. J. Pathol 144:321-328 (1994).
Inoue, et al., Coexpression of the c-kit Receptor and the Stem Cell Factor in Gynecological Tumors, Cancer Res. 54:3049-3053 (1994).
International Search Report and Written Opinion of the ISA dated Oct. 24, 2006 for PCT Application No. PCT/US2006/024524.
International Search Report and Written Opinion of the ISA dated Apr. 4, 2007 for PCT Application No. PCT/US2006/018726.
International Search Report and Written Opinion of the ISA dated Jun. 5, 2008 for PCT Application No. PCT/US2007/083910.
International Search Report and Written Opinion of the ISA dated Jun. 5, 2008 for PCT Application No. PCT/US2007/085289.
International Search Report and Written Opinion of the ISA dated Jun. 5, 2008 for PCT Application No. PCT/US2007/088243.
International Search Report and Written Opinion of the ISA dated Jul. 25, 2008 for PCT Application No. PCT/US2007/088443.
International Search Report and Written Opinion of the ISA dated Jul. 28, 2008 for PCT Application No. PCT/US2007/085299.
International Search Report and Written Opinion of the ISA dated Oct. 24, 2006 for PCT Application No. PCT/US2006/024361.
International Search Report and Written Opinion of the ISA dated Nov. 17, 2008 for PCT Application No. PCT/US07/088412.
International Search Report and Written Opinion of the ISA dated Nov. 25, 2005 for PCT Application No. PCT/U504/42470.
Isbel et al., Local macrophage proliferation correlates with increased renal M-CSF expression in human glomerulonephritis; Nephrol Dial Transplant 2001, 16: 1638-1647.
Ishizaka, et al., Human ret Proto-Oncogene Mapped to Chromsome 10q11.2, Oncogene 4(12):1519-1521 (1989).
Isozaki, et al., Deficiency of c-kit cells in patients with a myopathic form of chronic idiopathic intestinal pseudo-obstruction; 1997, Amer. J. of Gast. 9 332-334.
Iwane, et al., Myosin Subfragment-1 is Fully Equipped with Factors Essential for Motor Function, Biochem. and Biophys. Res. Comm. 230:76-80 (1997).
Izquierdo, et al., Differential Expression of the c-kit Proto-Oncogene in Germ Cel Tumours, J. Pathol. 177:253-258 (1995).
Jarugula et al., Nonlinear pharmacokinetics of 5-fluorouracil in rats. 1997, J Pharm Sci 86(7):756-757.
Jing, et al., GDNF-Induced Activation of the Ret Protein Tyrosine Kinase is Mediated by GDNFR-a, a Novel Receptor for GDNF, Cell 85:1113-1124 (1996).
Johann, S., et al., GLVR1, a Receptor for gibbon Ape Leukemia Virus, Is Homologous to a Phosphate Permease of *Neurospora crassa* and is Expressed at High Levels in the Brain and Thymus; (1992) J. Virol. 66:1635-1640.
Johnston, M., Gene Chips: Array of hope for understanding gene regulation; (1998) Curr. Biol. 8:R171-R174.
Jones, R., Biology and Treatment of Chronic Myeloid Leukemia, Curr. Opin. Onc. 9:3-7 (1997).
Jones, T., Interactive Computer Graphics: FRODO, Methods in Enzymology 115:157-171 (1985).
Jose et al., Blockade or Macrophage colony-Stimulating Factor Reduces Macrophage Proliferation and Accumulation in Renal Allograft Rejection; Am J Transplant 2003, 3(3):294-300.
Joseph-McCarthy, D., Computational Approaches to Structure-Based Ligand Design, Pharmacology & Therapeutics 84:179-191 (1999).
Kahl, et al., A Multiple-Approach Scintillation Proximity Assay to Measure the Association Between Ras and Raf, Anal. Biochem. 243:282-283 (1996).
Katritzky, et al., Regiospecific C-Acylation of Pyrroles and Indoles Using N-Acylbenzotriazoles, J. Org. Chem. 68:5720-5723 (2003).
Kay, et al., Eosinophils and Eosinophil-Associated Cytokines in Allergic Inflammation, Int. Arch. Aller. Immunol. 113:196-199 (1997).
Kern and Hampton, Direct Hybridization of Large-Insert Genomic Clones on High-Density Gridded cDNA Filter Arrays, Biotechniques 23:120-124 (1997).
Kim et al, A Merger of Rational Drug Design and Combinatorial Chemistry: Development and Application of Peptide Secondary Structure Mimetics, Combinatorial Chemistry & High Throughput Screening 3:167-183 (2000).
Kim et al, Database CAS on STN (Columbus, OH, USA) No. 138:55974, Preparation of 2-anilino-4-indolyl pyrimidines as tyrosine kinase inhibitors, abstract, 2002) see whole article.
Kinashi and Springer, Steel Factor and c-kit Cell-Matrix Adhesion; Blood 83:1033-1038 (1994).
Kirkpatrick, et al., Structure-Based Drug Design: Combinatorial Chemistry and Molecular Modeling, Combinatorial Chemistry & High Throughput Screening 2:211-221 (1999).
Kitamura, et al., Synthesis of Quinolines and 2H-Dihydropyrroles by Nucleophilic Substitution at the Nitrogen Atom of Oxime Derivatives, Synthesis 15:2415-2426 (2003).
Kline et al., Studies by 1H Nuclear Magnetic Resonance and Distance Geometry of the Solution Conformation of the x-Amylase Inhibitor Tendamistat, J. Mol. Biol. 189:377-382 (1986).
Knighton, et al., Structural Basis of the Intrasteric Regulation of Myosin Light Chain Kinases, Science 258:130-135 (1992).
Kodama et al, Congenital Osteoclast Deficiency in Osteopetrotic (op/op) Mice Is Cured by Injections of Macrophage colony-stimulating Factor; J. Exp,. Med. 1991, 173: 269-72.
Kolaskar et al, A Semi-Empirical Method for Prediction of Antigenic Determinants on Protein Antigens, FEBS Lett. 276:172-174 (1990).
Komoyira, S. et. al., Design, synthesis and biological activity of amidinobicyclic compounds (derivatives of DX-9065a) as a factor Xa inhibitors: SAR study of S1 and aryl binding sites, Bioorg. Med. Chem. 12, 2099 (2004).
Kondoh, et al., An in vivo model for receptor tyrosine kinase autocrine/paracrine activation: auto-stimulated Kit receptor acts as a tumor promoting factor in papillomavirus-induced tumorigenesis; 1995, Oncogene 10:341-347.

Kondoh, et al., Establishment and Further Characterization of a Line of Transgenic Mice Showing Testicular Tumorigenesis at 100% Incidence, J. Urol. 152:2151-2154 (1994).

Kondoh, et al., Very High Incidence of Germ Cell tumorigenesis (Seminomagenesis) in Human Papillomavirus Type 16 Transgenic Mice; 1991, J. Virol. 65:3335-3339.

Kroll, David J., et al., A Malfunctional Prokaryotic Protein Expression System: Overproduction, Affinity Purification, and Selective Detection; (1993) DNA Cell. Biol. 12:441-53.

Kundu, et al., Combinatorial Chemistry: Polymer Supported Synthesis of Peptide and Non-Peptide Libraries, Progress in Drug Research 53:89-156 (1999).

Kunisada, et al., Murine Cutaneous Mastocytosis and Epidermal Melanocytosis Induced by Keratinocyte Expression of Transgenic Stem Cell Factor; 1998, J. Exp. Med. 187:1565-1573.

Kunkel, T., Rapid and Efficient Site-Specific Mutagenesis Without Phenotypic Selection, Proc. Natl. Acad. Sci. USA 82:488-492 (1985).

Kuntz, et al., A Geometric Approach to Macromolecule-Ligand Interactions, J. Mol. Biol. 161:269-288 (1982).

Kuntz, et al., Structure-Based Molecular Design, Acc. Chem. Res. 27:117-123 (1994).

Lahm, et al., Interleukin 4 Down-Regulates Expression of c-kit and Autocrine Stem Cell Factor in Human Colorectal Carcinoma Cells, Cell Growth & Differ 6:1111-1118 (1995).

Lam et al., A new type of synthetic peptide library for identifying ligand-binding activity, Nature, 354: 82-84, 1991.

Langham et al., Metalation of Halogen-Metal Interconversion Reactions of Some Halogenated Phenyl Ethers, J. Am. Chem. Soc., vol. 63, 1941, pp. 545-549.

Lawicki et al., The pretreratment plasma level and disgnostic utility of M-CSF in benign breast tumor and breast cancer patients, Clinica Chimica Acta, 371: 112-116, 2006.

Le Meur et.al., Macrophage accumulation at a site of renal inflammation is dependent on the M-CSF/c-fms pathway; J Leukocyte Biology, 2002, 72: 530-537.

Lebl, et al., One-Bead-One-Structure Combinatorial Libraries, Biopolymers 37:177-198 (1995).

Lee, et al., HLA-DR-Triggered Inhibition of Hemopoiesis Involves Fas/Fas Ligand Interactions and is Prevented by c-kit Ligand, J. Immunol. 159:3211-3219 (1997).

Lee, et al., Mast Cells: A Cellular Link Between Autoantibodies and Inflammatory Arthritis, Science 297:1689-1692 (2002).

Levin, et al., Neoplasms of the Central Nervous System, Cancer Principles & Practice of Oncology 2:2022-2082 (1997).

Li, et al., Abrogation of c-kit/Steel Factor-Dependent Tumorigenesis by Kinase Defective Mutants of the c-kit Receptor: c-kit Kinase Defective Mutants as Candidate Tools for Cancer Gene Therapy, Canc. Res. 56:4343-4346 (1996).

Libby, Inflammation in atherosclerosis, Nature, 2002;420:868-874.

Liparoto, et al., Biosensor Analysis of the Interleukin-2 Receptor Complex, Journal of Molecular Recognition 12:316-321 (1999).

Lipinski, et al., Experimental and Computational Approaches to Estimate Solubility and Permeability in Drug Discovery and Development Settings, Advanced Drug Delivery Reviews 23:3-25 (1997).

Lipschultz et al., Experimental design for analysis of complex kinetics using surface plasmon resonance, Methods; (2000) 20(3):310-318.

London, et al., Expression of Stem Cell Factor Receptor (c-kit) by the Malignant Mast Cells from Spontaneous Canine Mast Cell Tumors, 1996, J. Compar. Pathol. 115:399-414.

Longley, et al., Altered Metabolism of Mast-cell Growth Factor (c-kit Ligand) in Cutaneous Mastocytosis, 1993, New Engl. J. Med. 328:1302-1307.

Longley, et al., Chymase Cleavage of Stem Cell Factor Yields a Bioactive Soluble Product, Proc. Natl. Acad. Sci. 94:9017-9021 (1997).

Longley, et al., Somatic c-KIT Activating Mutation in Urticaria Pigmentosa and Aggressive Mastocytosis: Establishment of Clonality in a Human Mast Cell Neoplasm, Nat. Gen. 12:312-314 (1996).

Loveland et al., Stem Cell Factor and c-kit in the Mammalian Testis: Lessons Originating from Mother Nature 19s Gene Knockouts, J. Endocrinol 153:337-344 (1997).

Lu, et al., Oriented Immobilization of Fab 19 Fragments on Silica Surfaces, Anal. Chem. 67:83-87 (1995).

Lukacs, et al., Stem Cell Factor (c-kit Ligand) Influences Eosinophil Recruitment and Histamine Levels in Allergic Airway Inflammation, J. Immunol. 156:3945-3951 (1996).

Luo, et al., Close Linkage with the RET Proto-Oncogene and Boundaries of Deletion Mutations in Autosomal Dominant Hirschsprung Disease, Hum Mol Genet. 2(11):1803-1808 (1993).

Lyman, et al., c-kit Ligand and Flt3 Ligand: Stem/Progenitor Cell Factors With Overlapping Yet Distinct Activities, Blood 91:1101-1134 (1998).

Ma et al., Indolinone Derivatives Inhibit Constitutively Activated KIT Mutants and Kill Neoplastic Mast Cells, 2000, J Invest Dermatol. 114:392-394.

Ma, et al., The c-KIT Mutation Causing Human Mastocytosis is Resistant to ST1571 and Other KIT Kinase Inhibitors; Kinases with Enzymatic Site Mutations Show Different Inhibitor Sensitivity Profiles Than Wild-type Kinases and Those With Regulatory-Type Mutations, Blood 99:1741-1744 (2002).

Madden, et al., Synthetic Combinatorial Libraries: Views on Techniques and Their Application Perspectives in Drug Discovery and Design 2:269-285 (1994).

Malmborg, et al., BIAcore as a Tool in Antibody Engineering, Journal of Immunological Methods 183:7-13 (1995).

Malmqvist, et al., Biomolecular Interaction Analysis: Affinity Biosensor Technologies for Functional Analysis of Proteins, Current Opinion in Chemical Biology 1:378-383 (1997).

Malmqvist., BIACORE: an affinity biosensor system for characterization of biomolecular interactions, (1999) Biochemical Society Transactions 27:335-40.

Markiewicz, et al., Synthetic Oligonucleotide Combinatorial Libraries and Their Applications, II Farmaco 55:174-177 (2000).

Martin, Y., Computer-Assisted Rational Drug Design, Methods Enz. 203:587-613 (1991).

Matayoshi, S. et al, Actions of brain-derived neurotrophic factor on spinal nociceptive transmission during inflammation in the rat, J Physiol. 569:685-95 (2005).

Mazeas, et. al., Synthesis of new melatoninergic ligands including azaindole moiety. Heterocycles, 50:1065 (1999).

McCall, et al., Characterization of Anti-Mouse FcyRII Single-Chain Fv Fragments Derived from Human Phage Display Libraries, Immunotechnology 4:71-87 (1998).

McPherson, A., Current Approaches to Macromolecule Crystallization, Eur. J. Biochem. 189:1-23 (1990).

Mekori, et al., Transforming Growth Factor-β Prevents Stem Cell Factor-Mediated Rescue of Mast Cells from Apoptosis After IL-3 Deprivation, 1994, J. Immunol 153:2194-2203.

Mekori, et al., The Role of c-Kit and Its Ligand, Stem Cell Factor, in Mast Cell Apoptosis, 1995, Int. Arch. Allergy Immunol. 107:136-138.

Meltzer, The pharmacological basis for the treatment of perennial allergic rhinitis and non-allergic rhinitis with topical corticosteroids, 1997, Aller. 52:33-40.

Meng, et al., Automated Docking with Grid-Based Energy Evaluation, J. Compt. Chem. 13:505-524 (1992).

Merour and Joseph, Synthesis and Reactivity of 7-Azaidoles (1H-Pyrrolo[2,3-b]pyridine), Curr. Org. 2001, 5:471-506.

Merritt, A., Solution Phase Combinatorial Chemistry, Comb Chem High Throughput Screen 1:57-72 (1998).

Metcalf, D., Lineage Commitment in the Progeny of Murine Hematopoietic Preprogenitor Cells: Influence of Thrombopoietin and Interleukin 5, Proc. Natl. Acad. Sci. USA 95:6408-6412 (1998).

Metcalfe, Classification and Diagnosis of Mastocytosis: Current Status, 1991, J. Invest. Derm 93:2S-4S.

Metcalfe, et al., Mast Cells, Physiol. Rev. 77:1033-1079 (1997).

Miller, et al., FLOG: A System to Select Quasi-Flexible Ligands Complementary to a Receptor of Known Three-Dimensional Structure, J. Comp. Aided Molec. Design 8:153-174 (1994).

Minakata et al., Functionalization of 1H-Pyrrolo[2,3-b]pyridine, Bulletin of the Chemical Society of Japan (1992), 65(11): 2992-2997.

Minakata, et al., Regioselective Funtionalization of 1H-Pyrrolo[2,3-b]pyridine Via its N-Oxide, Synthesis pp. 661-663 (1992).

Miranker et al, Functionality Maps of Binding Sites: A Multiple Copy Simultaneous Search Method, Proteins: Structure, Function, and Genetics 11:29-34 (1991).

Mitra, et al., Fluorescence Resonance Energy Transfer Between Blue-Emitting and Red-Shifted Excitation Derivatives of the Green Fluorescent Protein, Gene 173:13-17 (1996).

Miyaura and Suzuki, Palladium-Catalyzed Cross-Coupling Reactions of Organoboron Compounds, Chem. Rev. 1995, 95:2457.

Mol, et al. Structural Basis for the Autoinhibition and STI-571 Inhibition of c-Kit Tyrosine Kinase, J. Biol. Chem. 279:31655-31663 (2004).

Mol, et al., Structure of a c-Kit Product Complex Reveals the Basis for Kinase Transactivation, J. Biol. Chem. 278:31461-31464 (2003).

Morgan, C., Pollard, J.W., and Stanley, E.R., Isolation and Characterization of a Cloned Growth Factor Dependent Macrophage Cell Line, BAC1.2F5, Journal of Cellular Physiology, 130:420-427 (1987).

Motoyoshi, Biological activities and clinical application of M-CSF, Int J Hematol. 1998, 67:109-22.

Murty, et al., A Genetic Perspective of Male Germ Cell tumors, 1998, Sem. Oncol. 25:133-144.

Naclerio, et al., Rhinitis and Inhalant Allergens, JAMA 278:1842-1848 (1997).

Nagafuji and Cushman, A General Synthesis of Pyrroles and Fused Pyrrole Systems from Ketones and Amino Acids, J. Org. Chem. 61:4999-5003 (1996).

Nagata, et al., Elevated Expression of the Proto-Oncogene c-kit in Patients with Mastocytosis, Leukemia 12:175-181 (1998).

Nahm and Weinreb, N-Methoxy-N-Methylamides as Effective Acylating Agents, Tetrahedron Lett. 22(39):3815-3818 (1981).

Navaza, J., AMoRe: an Automated Package for Molecular Replacement, Acta Cryst. A50:157-163 (1994).

Neidle, et al., Molecular Modeling to Study DNA Intercalation by Anti-Tumor Drugs, Methods Enz. 203:433-458 (1991).

Ng, et al., Engineering Protein-lipid Interactions: Targeting of Histidine-Tagged Proteins to Metal-Chelating Lipid Monolayers, Langmuir 11:4048-4055 (1995).

Nicholls, et al., Protein Folding and Association: Insights From the Interfacial and Thermodynamic Properties of Hydrocarbons, Proteins 11:281-296 (1991).

Nichols, et al., Development of a Scintillation Proximity Assay for Peroxisome Proliferator-Activated Receptor y Ligand Binding Domain, Anal. Biochem. 257:112-119 (1998).

Notice of Allowance dated Dec. 26, 2007 for U.S. Appl. No. 11/016,350.

Notice of Allowance dated Jun. 6, 2008 for U.S. Appl. No. 11/154,988.

Okada, et al., Gene Therapy Against an Experimental Glioma Using Adeno-Associated Virus Vectors, Gene Ther. 3:957-964 (1996).

Okayama, et al., Human Lung Mast Cells are Enriched in the Capacity to Produce Granulocyte-Macrophage Colony-Stimulating Factor in Response to IgE-Dependent Stimulation, Eur. J. Immunol. 28:708-715 (1998).

Okayama, et al., Activation of Eosinophils with Cytokines Produced by Lung Mast Cells, Int. Arch. Aller. Immunol. 114(suppl. 1):75-77 (1997).

Olah, et al., Synthetic Methods and Reactions: Part 209. Improved Preparation of Aldehydes and Ketones from N,N-Dimethylamides and Grignard Reagents, Synthesis pp. 228-230 (1984).

O'Shannessy and Winzor, Interpretation of Deviations from Pseudo-First-Order Kinetic Behavior in the Characterization of Ligand Binding by Biosensor Technology, Analytical Biochemistry 236:275-283 (1996).

O'Shannessy, Determination of kinetic rate and equilibrium binding constants for macromolecular interactions: a critique of the surface plasmon resonance literature, (1994) Current Opinions in Biotechnology, 5:65-71.

Ottoni, et al., Efficient and Simple Methods for the Introduction of the Sulfonyl, Acyl and Alkyl Protecting Groups on the Nitrogen of Indole and its Derivatives, Tetrahedron 54:13915-13928 (1998).

Otwinowski, Z., Maximum Likelihood Refinement of Heavy Atom Parameters, Dept. of Molecular Biophysics and Biochemistry pp. 80-86 (1991).

Owicki et al., Application of Fluorescence Polarization Assays in High-Throughput Screening, (1997), Genetic Engineering News, 17:27.

Parker, et al., Development of High Throughput Screening Assays Using Fluorescence Polarization: Nuclear Receptor-Ligand-Binding and Kinase/Phosphatase Assays, J Biomol Screen 5:77-88 (2000).

Perrin, D., Nucleic Acids for Recognition and Catalysis: Landmarks, Limitations, and Looking to the Future, Combinatorial Chemistry & High Throughput Screening 3:243-269 (2000).

Petty et al, The effect of systemically administered recombinant human nerve growth factor in healthy human subjects. Ann Neurol. 36:244-6 (1994).

Pflugrath, et al., Crystal Structure Determination, Refinement and the Molecular Model of the x-Amylase Inhibitor Hoe-467A, J. Mol. Biol. 189:383-386 (1986).

Pierce et al., Local anaesthetics. I. beta-Monoaklylaminoethyl Esters of Alkoxybenzoic Acids, J. Am. Chem. Soc., vol. 64, 1942, pp. 1691-1694.

Pignon, J.M., C-kit mutations and mast cell disorders A model of activating mutations of growth factor receptors, Hermatol Cell Ther 39:114-116 (1997).

Plunkett et al, A Silicon-Based Linker for Traceless Solid-Phase Synthesis, J. Org. Chem. 60:6006-6007 (1995).

Poul, et al., Selection of Tumor-Specific Internalizing Human Antibodies from Phage Libraries, J. Mol. Biol. 301:1149-1161 (2000).

Price et al.; Summary report on the ISOBM TD-4 Workshop: analysis of 56 monoclonal antibodies against the MUC1 mucin, (1998) Tumour Biology 19 Suppl 1:1-20.

Qiao, et. al., Role of Macrophage Colony-Stimulating Factor in Atherosclerosis, Am. J. Path. 1997;150:1687-1699.

Rajavashisth, et. al., Heterozygous Osteopetrotic (op) Mutation Reduces Atherosclerosis in LDL Receptor-deficient Mice, J. Clin. Invest. 1998;101:2702-2710.

Rajpert-de Meyts, et al., Expression of the c-kit Protein Product in Carcinoma-in-situ and Invasive Testicular Germ Cell Tumours, Int. J. Androl. 17:85-92 (1994).

Ricotti, et al., c-kit Is Expressed in Soft Tissue Sarcoma of Neuroectodermic Origin and Its Ligand Prevents Apoptosis of Neoplastic Cells, Blood 91:2397-2405 (1998).

Ridge et al, FMS mutations in myelodysplastic, leukemic, and normal subjects, Proc. Nat. Acad. Sci., 1990, 87:1377-1380.

Roberts, S., et al., Generation of an antibody with enhanced affinity and specificity for its antigen by protein engineering, (1987) Nature 328:731-734.

Robinson et al., Stimulation of Bone Marrow Colony Growth in Vitro by Human Urine; Blood, 1969, 33:396-9.

Robison et al, 7-Azaindole. I. Synthesis and Conversion to 7-Azatryptophan and Other Derivatives, J. Am. Chem. Soc. 77:457-460 (1955).

Rodan, G., et al., Therapeutic Approaches to Bone Diseases, Science. 2000;289:1508.

Rosenfeld, Human artificial chromosomes get real, (1997) Nat. Genet. 15:333-335.

Ryan, et al., Role for the Stem Cell Factor/KIT Complex in Schwann Cell Neoplasia and Mast Cell Proliferation Associated with Neurofibromatosis, 1994, J. Neuro. Res. 37:415-432.

Saify et al, Database CAS on STN (Columbus, OH, USA) No. 124:170379, Synthesis of some 2-azaindole derivatives: their cyctotoxicity and antibacterial activity, abstract, (1996), See RN 271-63-6.

Saify et al., Synthesis of some 7-azaindole derivatives: Their cytotoxicity and antibacterial activity, Pakistan Journal of Scientific and Industrial Research, 37(10): 439-441, 1994.

Saiki, Amplification of Genomic DNA, in PCR Protocols, Innis et al., Eds., Academic Press, San Diego, CA 1990, pp. 13-20.

Sambrook et al, Molecular Cloning: A Laboratory Manual, 1989, Cold Spring Harbor Laboratory Press, Cold Spring Harbor N.Y, pp. 16.30-16.37.

Sandlow, et al., Expression of c-KIT and its Ligand, Stem Cell Factor, in Normal and Subfertile Human Testicular Tissue, 1996, J. Androl. 17:403-408.

Santoro, et al., The ret Proto-Oncogene is Consistently Expressed in Human Pheochromocytomas and Thyroid Medullary Carcinomas, Oncogene, 5(10):1595-1598 (1990).

Sawada et al., 4-(Benzoylindolizinyl)butyric acids; Novel nonsteroidal inhibitors of steroid 5;1-reductase. III, Chemical and Pharmaceutical Bulletin (2001), 49(7): 799-813.

Sawada, et al., Role of Cytokines in Leukemic type Growth of Myelodysplastic CD34+ Cells, 1996, Blood 88:319-327.

Sawai, et al., Aberrant growth of granulocyte-macrophage progenitors in juvenile chronic myelogenous leukemia in serum-free culture, 1996, Exp. Hem. 2:116-122.

Scheffner, et al., The E6 Oncoprotein Encoded by Human Papillomavirus Types 16 and 18 Promotes the Degradation of p53, Cell 63:1129-1136 (1990).

Schiemann and Winkelmüller, p-Fluorobenzoic Acid, Org. Syn. Coll. vol. 2:299, 1943.

Schneider, et al., Functional Purification of a Bacterial ATP-Binding Cassette Transporter Protein (MalK) from the Cytoplasmic Fraction of an Overproducing Strain, (1995) Protein Expr, Purif. 6435:10.

Schneller et. al., Synthesis of 4-Amino-1 H-pyrrolo[2,3-b]pyridine {1 ,7-Dideazaadenine) and 1H-Pyrrolo[2,3-b]pyridine-4-ol (1,7-Dideazahypoxanthine), J. Org. Chem. 1980, 45:4045.

Schuhmann, et al., Immobilization of Enzymes on Langmuir-Blodgett Films via a Membrane-Bound Receptor. Possible Applications for Amperometric Biosensors, Adv. Mater. 3:388-391 (1991).

Schummer, et al., Inexpensive Handheld Device for the Construction of High-Density Nucleic Acid Arrays, Biotechniques 23:1087-1092 (1997).

Schweizer, et al., Combinatorial Synthesis of Carbohydrates, Curr Opin. Chem. Biol., 3:291-298 (1999).

Secor, et al., Mast cells are essential for early onset and severe disease in a murine model of multiple sclerosis. J. Exp. Med. 5:813-821 (2000).

Selvin, P., Fluorescence Resonance Energy Transfer, Meth. Enzymol. 246:300-345 (1995).

Sheets, et al., Efficient Construction of a Large Nonimmune Phage Antibody Library: The Production of High-Affinity Human Single-Chain Antibodies to Protein Antigens, Proc Natl Acad Sci USA 95:6157-6162 (1998).

Shibata et al, Alveolar macrophage deficiency in osteopetrotic mice deficient in macrophage colony-stimulating factor is spontaneously corrected with age and associated with matrix metalloproteinase expression and emphysema, Blood 2001, 98: pp. 2845-2852.

Siegel, et al., Mass Spectral Analysis of a Protein Complex Using Single-Chain Antibodies Selected on a Peptide Target: Applications to Functional Genomics, Journal of Molecular Biology 302:285-293 (2000).

Sigal, et al., A Self-Assembled Monolayer for the Binding and Study of histidine-Tagged Proteins by Surface Plasmon Resonance, (1996) Anal. Chem. 68:490-497.

Smalley et al., c-KIT signaling as the driving oncogenic event in sub-groups of melanomas. Histol Histopathol, 24:643-650, 2009.

Solinas-Toldo, et al., Matrix-Based Comparative Genomic Hybridization Biochips to Screen for Genomic Imbalances, Genes, Chromosomes & Cancer 20:399-407 (1997).

Song et al., Isomerism of Bis(7-azaindolyl)methane, Organic Letters (2002), 4:23, 4049-4052, Table of content p. 1-16 and Supporting information p. 1-15.

Sperling, et al., Expression of the Stem Cell Factor Receptor C-Kit (CD117) in Acute Leukemias, Haemat 82:617-621 (1997).

Stanulla, et al., Coexpression of Stem Cell Factor and Its Receptor c-Kit in Human Malignant Glioma Cell Lines, Act Neuropath 89:158-165 (1995).

Steinman, Multiple sclerosis: A coordinated immunological attack against myelin in the central nervous system. Cell 85:299-302 (1996).

Strohmeyer, et al., Expression of the C-kit Proto-Oncogene and its Ligand Stem Cell Factor (SCF) in Normal and Malignant Human Testicular Tissue, 1995, J. Urol. 153:511-515.

Strohmeyer, et al., Expression of the hst-1 and c-kit Protooncogenes in Human Testicular Germ Cell Tumors, Canc. Res. 51:1811-1816 (1991).

Su & Tsou, Synthesis of bromo-substituted Idoxyl Esters for Cytochemical Demonstration of Enzyme Activity, J. Am. Chem. Soc.,82, 1960, 1187.

Sun, C., Recent Advances in Liquid-Phase Combinatorial Chemistry, Comb. Chem. & High Throughput Screening 2:299-318 (1999).

Sun, et al., Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases, J. Med. Chem. 42:5120-5130 (1999).

Supplemental Notice of Allowance dated Jul. 23, 2008 for U.S. Appl. No. 11/154,988.

Supplemental Notice of Allowance dated Sep. 8, 2008 for U.S. Appl. No. 11/154,988.

Supplementary Search Report dated Aug. 4, 2009 for European Application No. 04814626.0.

Tada, et al., Analysis of Cytokine Receptor Messenger RNA Expression in Human Glioblastoma Cells and Normal Astrocytes by Reverse-Transcription Polymerase Chain Reaction, J. Neuro 80:1063-1073 (1994).

Takahashi et al, ret Transforming Gene Encodes a Fusion Protein Homologous to Tyrosine Kinases, Mol Cell Biol. 7:1378-1385 (1987).

Takahashi, et al., Activation of a Novel Human Transforming Gene, ret, by DNA Rearrangement, Cell 42(2):581-588 (1985).

Takahashi, et al., Cloning and Expression of the ret Proto-Oncogene Encoding a Tyrosine Kinase with Two Potential Transmembrane Domains, Oncogene 3(5):571-578 (1988).

Taylor et al. The Rapid Generation of Oligonucleotide-directed Mutations at High Frequency Using Phosphorothloate-Modified DNA; (1985) Nucl. Acids Res. 13:8764-8785.

Teitelbaum, Bone Resorption by Osteoclasts, Science. 2000;289:1504.

Thibault et. al., Concise and Efficient Synthesis of 4-fluoro-1H-pyrrolo[2,3-b] pyridine, Org. Lett. 2003, 5:5023-5025.

Thomas et al, The Eosinophil and its Role in Asthma, Gen. Pharmac 27:593-597 (1996).

Thomas, et. al., Light-Emitting Carbazole Derivatives: Potential Electroluminescent Materials, J. Am. Chem. Soc. 123:9404-9411 (2001).

Toste, et al., A Versatile Procedure for the Preparation of Aryl Thiocyanates Using N-Thiocyanatosuccinimide (NTS), Synth. Comm. 25(8):1277-1286 (1995).

Toyota, et al., Expression of c-kit and kit Ligand in Human Colon Carcinoma Cells, 1993, Turn Biol 14:295-302.

Trupp, et al., Functional Receptor for GDNF Encoded by the c-ret Proto-Oncogene, Nature 381:785-789 (1996).

Tsujimura, et al., Substitution of an Aspartic Acid Results in Constitutive Activation of c-kit Receptor Tyrosine Kinase in a Rat Tumor Mast Cell Line RBL-2H3, 1995, Int. Arch. Aller. Immunol 106:377-385.

Tsujimura, et al.,Ligand-Independent Activation of c-kit Receptor Tyrosine Kinase in a Murine Mastocytoma Cell Line P-815 Generated by a Point Mutation, Blood 9:2619-2626 (1994).

Tsujimura, T., Role of c-kit Receptor Tyrosine Kinase in the Development, Survival and Neoplastic Transformation of Mast Cells, Pathol Int 46:933-938 (1996).

Turner, et al., Nonhematopoeietic Tumor Cell Lines Express Stem Cell Factor and Display c-kit Receptors, 1992, Blood 80:374-381.

Undenfriend, et al., Scintillation Proximity Assay: A Sensitive and Continuous Isotopic Method for Monitoring Ligand/Receptor and Antigen/Antibody Interactions, Anal. Biochem., 161:494-500 (1987).

Uritskaya et al., STN Accession No. 1974-27133; Document No. 08:27133; Abstract of Khimiya Geterotsiklicheskikh Soedinenii (1973, (10), 1370-3).

US Notice of Allowance dated May 27, 2010 in related U.S. Appl. No. 11/435,381.

US Office Action dated Jan. 4, 2008 for U.S. Appl. No. 11/154,988.
US Office Action dated Jun. 6, 2007 for U.S. Appl. No. 11/016,350.
US Office Action dated Aug. 22, 2007 for U.S. Appl. No. 11/487,134.
US Office Action dated Sep. 22, 2009 for U.S. Appl. No. 11/986,667.
US Office Action dated Sep. 23,2009 for U.S. Appl. No. 11/962,044.
US Office Action dated Oct. 19, 2007 for U.S. Appl. No. 11/154,988.

US Office Action dated Oct. 26, 2007 for U.S. Appl. No. 11/016,350.
US Office Action dated Feb. 17, 2010 for U.S. Appl. No. 11/962,044.
US Office Action dated Aug. 2, 2007 in related U.S. Appl. No. 11/016,350.
US Office Action dated Feb. 19, 2010 for U.S. Appl. No. 11/435,381.
US Office Action dated Feb. 26, 2010 for U.S. Appl. No. 11/986,667.
US Office Action dated Jun. 1, 2009 for U.S. Appl. No. 11/435,381.
US Office Action dated Mar. 4, 2009 for U.S. Appl. No. 11/435,381.
US Office Action dated May 15, 2008 in related U.S. Appl. No. 11/487,134.
US Office Action Dec. 18, 2009 for U.S. Appl. No. 11/473,347.
Valent, P., Biology, Classification and Treatment of Human Mastocytosis, Wein/Klin Wochenschr 108:385-397 (1996).
Van Heyningen,V., One Gene—Four Syndromes, Nature 367:319-320 (1994).
Van Regenmortel, Use of biosensors to characterize recombinant proteins, (1994), Developments in Biological Standardization, 83:143-51.
Vely F. et al., BIAcore® analysis to test phosphopeptide-SH2 domain interactions, (2000), Methods in Molecular Biology, 121:313-21.
Verfaillie, Chronic myelogenous leukemia: too much or too little growth, or both?; Leukemia, 1998, 12:136-138.
Viskochil, D., It Takes Two to Tango: Mast Cell and Schwann Cell Interactions in Neurofibromas, J Clin Invest., 112:1791-1793 (2003).
Vliagoftis, et al., The protooncogene c-kit and c-kit ligand in human disease, Journ. Clin. Immunol, 100:435-440 (1997).
Weber, P., Physical Principles of Protein Crystallization, Adv. Protein Chem., 41:1-36 (1991).
Wendt, et al, Identification of novel binding interactions in the development of potent, selective 2-naphthamidine inhibitors of urokinase, synthesis, structural analysis, and SAR of y-Phenyl amide 6-substitution. J. Med. Chem., 47(2):303 (2004).
Werness, et al., Association of Human Papillomavirus Types 16 and 18 E6 Proteins with p53, Science 248:76-79 (1990).
Wessjohann, L., Synthesis of Natural-Product-Based Compound Libraries, Curr Opin Chem Biol., 4:303-309 (2000).
Wharam, et al., Specific Detection of DNA and RNA Targets Using a Novel Isothermal Nucleic Acid Amplification Assay Based on the Formation of a Three-Way Junction Structure, Nucleic Acids Res., 29:1-8 (2001).
Williams et al., Dissection of the Extracellular Human Interferon y Receptor a-Chain into two Immunoglobulin-like domains. Production in an *Escherichia coli* Thioredoxin Gene Fusion Expression system and Recognition by Neutralizing Antibodies, (1995) Biochemistry 34:1787-1797.
Woon, et al., Construction and Characterization of a 10-Fold Genome Equivalent Rat P1-Derived Artificial Chromosome Library, Genomics, 50:306-316 (1998).
Wuthrich, K., Chapter 10: Three-Dimensional Protein Structures by NMR, NMR of Proteins and Nucleic Acids, 10:176-199 (1986).
Wyckoff et al., Direct visualization of macrophage-assisted tumor cell intravasation in mammary tumors. Cancer Research, 67(6): 2649-2656, 2007.
Xu et al, Modulation of Endothelial Cell function by Normal Polyspecific Human Intraveneous immunoglobulins, Am. J. Path. 1998;153:1257-1266.
Yakhontov et al., Derivatives of 7-azaindole. XV. Electrophilic substitution of 4-methyl-7-azaindole and its derivatives, Zhurnal Obshchei Khimii (1965), 1(11): 2032-2040. (English abstract only).
Yang et al., Nf1-Dependent tumors require a microenvironment containing Nf1+/_-and c-kit-Dependent bone marrow, Cell, 135:437-448, 2008.
Yang et. al., Synthesis of some 5-substituted indoles. Heterocycles, 34:1169 (1992).
Yang, et al., Neurofibromin-Deficient Schwann Cells Secrete a Potent Migratory Stimulus for NF1+/-Mast Cells, J Clin Invest., 112:1851-1861 (2003).
Yee, et al., Role of kit-Ligand in Proliferation and Suppression of Apoptosis in Mast Cells: Basis for Radiosensitivity of White Spotting and Steel Mutant Mice, J. Exp. Med., 179:1777-1787 (1994).
Yeung et al., Friedel-Crafts acylation of indoles in acidic imidazolium chloroaluminate ionic liquid at room temperature, Tetrahedron Letters, (2002), 43(33), 5793-5795.

Yuan, et al., Human Peripheral Blood Eosinophils Express a Functional c-kit Receptor for Stem Cell Factor that Stimulates Very Late Antigen 4 (VLA-4)-Mediated Cell Adhesion to Fibronectin and Vascular Cell Adhesion Molecule 1 (VCAM-1), J. Exp. Med. 186:313-323 (1997).
Zanon, et. al., Cooper-Catalyzed Domino Halide Exchange-Cyanation of Aryl Bromides, J. Am. Chem. Soc. 125:2890-2891 (2003).
Zhang et al., An effective procedure for the acylation of azaindoles at C-3, Journal of Organic Chemistry (2002), 67(17): 6226-6227 and p. S1-S30.
Bouzakri, K. and Zierath, J.R., MAP4K4 Gene silencing in Human Skeletal Muscle Prevents Tumor Necrosis Factor-α-induced Insulin Resistance, J. Biol. Chem. 282:7783-7789 (2007).
Chou, T. and Talalay, P., Quantitative analysis of Dose-Effect Relationships: The Combined Effects of Multiple Drugs or Enzyme Inhibitors, Adv. Enzyme Regul. 22:27-55 (1984).
Chou et al., Computerized Quantitation of Synergism and Antagonism of Taxol, Topotecan, and Cisplatin Against Human Teratocarcinoma Cell Growth: a Rational Approach to Clinical Protocol Design, J. Natl. Cancer Inst. 86:1517-24 (1994).
Collins et al., A small interfereing RNA screen for modulators of tumor cell motility identifies MAP4K4 as a prommigratory kinase, Proc. Natl. Acad. Sci. USA, 103:3775-3780.
Coulie et al, Recombinant Human Neurotropic Factors Accelerate Colonic Transit and Relieve Constipation in Humans, Gastroenterology 119:41-50 (2000).
Douma, S. et al, Suppression of anoikis and induction of metastasis by the neurotropic receptor TrkB, Nature 430:1034-9 (2004).
Chou, T. et al., Chemotherapeutic Synergism, Potentiation and Antagonism, Encyclopedia of Human Biology, Academic Press, 2:371-9 (1991).
Halvorson, K.G. et al., A Blocking Antibody to Nerve Growth Factor Attenuates Skeletal Pain Induced by Prostate Tumor Cells Growing in Bone, Cancer Res. 65:9426-35 (2005).
Hood, J.D. et al., Tumor Regression by Targeted Gene Delivery to the Neovasculature, Science 296, 2404 (2002).
Kassel, O. et al., Local increase in the No. Of mast cells and expression of nerve growth factor in the bronchus of asthmatic patients after repeated inhalation of allergen at low-dose, Clin. Exp. Allergy 31:1432-40 (2001).
Kunnimalaiyaan, M. and Chen, H. et al., The Raf-1 pathway: a molecular target for treatment of select neuroendocrine tumors? Anticancer Drugs 17(2):139-42 (2006).
Machida, N. et al., Mitogen-activated Protein Kinase Kinase Kinase Kinase 4 as a Putative Effector of Rap2 to Activate the c-Jun N-terminal Kinase, J. Biol. Chem. 279: 15711-1571412004).
Mack, K.D. et al., Functional identification of kinases essential for T-cell activation through a genetic suppression screen, Immunol. Lett. 96, 129-145 (2005).
Nakagawara, A. et al., Expression and Function of *TRK-B* an *BDNF* in Human Neuroblastomas, Mol. Cell Biol. 14:759-767 (1994).
Nassentein, C. et al, The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma, J. Exp. Med. 198:455-467 (2003).
Niihori, T. et al., Germline *KRAS* and *BRAF* mutations in cardio-facio-cutaneous syndrome, Nature Genet. 38(3):294-6 (2006).
Ochs, G. et al, A phase I/II trial of recombinant methionyl human brain derived neurotrophic factor administered by intrathecal infusion to patients with amyotrophic lateral sclerosis, Amyotroph Lateral Scler Other Motor Neuron Disord. 1:201-6 (2000).
Sclabas, G.M. et al, Overexpression of Tropomysin-Related Kinase B in Metastatic Human Pancreatic Cancer Cells, Clin. Cancer. Res. V11:440-449 (2005).
Chou, T.C. and Rideout, D.C., Synergism and Antagonism in Chemotherapy, Academic Press, 61-102 (1991).
Tang, X. et al., An RNA interference-based screen identifies MAP4K4/NIK as a negative regulator of PPARγ, adipogenesis, and insulin-responsive hexose transport, Proc. Natl. Acad. Sci. U. S. A. 103:2087-2092 (2006).

Wild, K.D. et al, Antibodies to Nerve Growth Factor Reverse Established Tactile Allodynia in Rodent Models of Neuropathic Pain without Tolerance, J. Pharmacol. Exp. Ther. 322:282-287 (2007).

Wright, J.H. et al., The STE20 Kinase KGK Is Broadly Expressed in Human tumor Cells and Can Modulate Cellular Transformation, Invasion, and Adhesion, Mol. Cell. Biol. 23:2068-2082 (2003).

Yang, Z.F. et al, Identification of Brain-Derived Neurotrophic Factor as a Novel Functional Protein in Hepatocellular Carcinoma, Cancer Res. 65:219-225 (2005).

Yao, Z. et al., A Novel Human STE20-related Protein Kinase, HGK, That Specifically Activates the c-Jun N-terminal Kinase Signaling Pathway, J. Biol. Chem. 274:2118-2125 (1999).

International Search Report for PCT Patent Application No. PCT/US2007/088231.

International Search Report for PCT Patent Application No. PCT/US2007/088237.

* cited by examiner

COMPOUNDS AND METHODS FOR KINASE MODULATION, AND INDICATIONS THEREFOR

RELATED PATENT APPLICATIONS

This application claims priority to U.S. Provisional App. No. 60/876,953, entitled "Compounds and Methods for Kinase Modulation, and Indications Therefor", filed Dec. 21, 2006, and is related to U.S. patent application Ser. No. 11/473,347, entitled "Compounds and Methods for Kinase Modulation, and Indications Therefor", filed Jun. 21, 2006, which claims the benefit of U.S. Provisional App. No. 60/731,528, entitled "Compounds and Methods for Kinase Modulation, and Indications Therefor", filed Oct. 28, 2005, and U.S. Provisional App. No. 60/692,960, entitled "Compounds and Methods for Kinase Modulation, and Indications Therefor", filed Jun. 22, 2005, all of which are incorporated herein by reference in their entirctics and for all purposes.

FIELD OF THE INVENTION

The present invention relates to kinases and compounds which modulate kinases, and uses therefor. Particular embodiments contemplate disease indications which are amenable to treatment by modulation of kinase activity by the compounds of the present invention.

BACKGROUND OF THE INVENTION

The information provided herein is intended solely to assist the understanding of the reader. None of the information provided nor references cited is admitted to be prior art to the present invention. Each of the references cited herein is incorporated in its entirety.

Receptor protein kinases regulate key signal transduction cascades that control or are involved in the control of a plethora of physiological functions including cellular growth and proliferation, cell differentiation, cellular development, cell division, cell adhesion, stress response, short-range contact-mediated axonal guidance, transcription regulation, aberrant mitogenesis, angiogenesis, abnormal endothelial cell-cell or cell-matrix interactions during vascular development, inflammation, lymphohematopoietic stem cell activity, protective immunity against specific bacteria, allergic asthma, aberrant tissue-specific responses to the activation of the JNK signal transduction pathway, cell transformation, memory, apoptosis, competitive activity-dependent synapse modification at the neuromuscular synapse, immunological mediation of disease, and calcium regulation.

Specific disease states associated with aberrant regulation of protein kinases include, for example without limitation, acrocephalo-syndactyly type I, acute mycloid leukemia, AIDS-induced non-Hodgkin's lymphoma, Alzheimer's disease, amyotrophic lateral sclerosis, arthritis, asthma, atherosclerosis, atopic dermatitis, autoimmune diseases, bacterial infection, bladder cancer, cancer of the breast, cancer of the central nervous system, cancer of the colon, cancer of the endometrium, cancer of the fallopian tube, cancer of the gastrointestinal tract, cancer of the ovary, heart failure, chronic myeloid leukemia, colon carcinoma, colorectal cancer, chronic obstructive pulmonary disease (COPD), Crouzon Syndrome, diabetes, diabetic nephropathy, emphysema, endometriosis, epidermoid cancer, fibrotic disorders, gastrointestinal stromal tumor (GIST), glomerulonephritis, Graves' disease, head injury, hepatocellular carcinoma, Hirschsprung's disease, human gliomas, immunodeficiency diseases, inflammatory disorders, ischemic stroke, Jackson-Weiss syndrome, leiomyosarcoma, leukemias, lupus nephritis, malignant melanoma, malignant nephrosclerosis, mastocytosis, mast cell tumors, melanoma of the colon, MEN2 syndromes, metabolic disorders, migraine, multiple sclerosis, myeloproliferative disorders, nephritis, neurodegenerative diseases, neurotraumatic diseases, non small cell lung cancer, organ transplant rejection, osteoporosis, pain, Parkinson's disease, Pfeiffer Syndrome, polycystic kidney disease, primary lymphoedema, prostate cancer, psoriasis, vascular restenosis, rheumatoid arthritis, dermal and tissue scarring, selective T-cell defect (STD), severe combined immunodeficiency (SCID), small cell lung cancer, spinal cord injury, squamous cell carcinoma, systemic lupus erythematosis, testicular cancer, thrombotic microangiopathy syndromes, Wegener's granulomatosis, X-linked agammaglobulinemia, viral infection, diabetic retinopathy, alopecia, erectile dysfunction, macular degeneration, chronic lymphocytic leukemia (CLL), myelodysplastic syndrome (MDS), neurofibromatosis, and tuberous sclerosis.

This application is related to the following published patent applications: WO 2004024895, US 20040142864, WO 2004078923, US 20050170431, WO 2005028624, US 20050164300, and WO 2005062795, each of which are hereby incorporated by reference herein in their entireties including all specifications, figures, and tables, and for all purposes.

SUMMARY OF THE INVENTION

Compounds are contemplated that are active on protein kinases in general, including, but not limited to, Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGFIR, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, IEC, Tie2, TrkA, TrkB, Yes, and/or Zap70, including any mutations of these kinases. In some aspects, the compounds are active on protein kinases including A-Raf, B-Raf and/or c-Raf-1, including any mutations thereof. In some aspects, compounds are of Formula I, Formula II, or Formula III as described below.

Also contemplated in accordance with the present invention are methods for the use of the above-described compounds in treating diseases and conditions associated with regulation of the activity of the above-described kinases. Thus, the use of compounds for therapeutic methods involving modulation of protein kinases are provided, as well as compounds that can be used for therapeutic methods involving modulation of protein kinases.

In some embodiments, compounds have the structure according to the following Formula I:

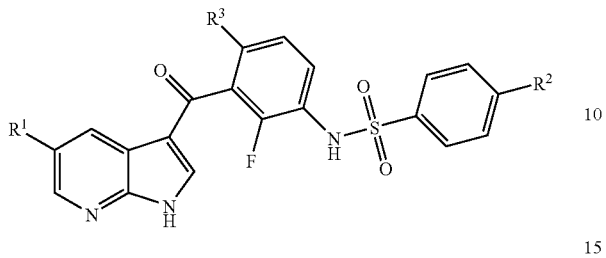

Formula I all salts, prodrugs, tautomers and isomers thereof,
wherein:
R¹ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —NH₂, —CN, —NO₂, —C(O)OH, —S(O)₂NH₂, —C(O)NH₂, —C(S)NH₂, —NHC(O)NH₂, —NHC(S)NH₂, —NHS(O)₂NH₂, —OR⁴, —SR⁴, —NR⁵R⁴, —C(O)R⁴, —C(S)R⁴, —C(O)OR⁴, —C(O)NR⁵R⁴, —C(S)NR⁵R⁴, —S(O)₂NR⁵R⁴, —NR⁵C(O)R⁴, —NR⁵C(S)R⁴, —NR⁵S(O)₂R⁴, —NR⁵C(O)NH₂, —NR⁵C(O)NR⁵R⁴, —NR⁵C(S)NH₂, —NR⁵C(S)NR⁵R⁴, —NR⁵S(O)₂NH₂, —NR⁵S(O)₂NR⁵R⁴, —S(O)R⁴, and —S(O)₂R⁴;

R² is selected from the group consisting of halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —NH₂, —CN, —NO₂, —C(O)OH, —S(O)₂NH₂, —C(O)NH₂, —C(S)NH₂, —NHC(O)NH₂, —NHC(S)NH₂, —NHS(O)₂NH₂, —OR⁴, —SR⁴, —NR⁵R⁴, —C(O)R⁴, —C(S)R⁴, —C(O)OR⁴, —C(O)NR⁵R⁴, —C(S)NR⁵R⁴, —S(O)₂NR⁵R⁴, —NR⁵C(O)R⁴, —NR⁵C(S)R⁴, —NR⁵S(O)₂R⁴, —NR⁵C(O)NH₂, —NR⁵C(O)NR⁵R⁴, —NR⁵C(S)NH₂, —NR⁵C(S)NR⁵R⁴, —NR⁵S(O)₂NH₂, —NR⁵S(O)₂NR⁵R⁴, —S(O)R⁴, and —S(O)₂R⁴;

R³ is selected from the group consisting of hydrogen, fluoro and chloro;

R⁴ is selected from the group consisting of optionally substituted lower alkyl, optionally substituted lower alkenyl, provided, however, that when R⁴ is optionally substituted lower alkenyl, no alkene carbon thereof is bound to N, S, O, S(O), S(O)₂, C(O) or C(S) of —OR⁴, —SR⁴, —NR⁵R⁴, —C(O)R⁴, —C(S)R⁴, —C(O)OR⁴, —C(O)NR⁵R⁴, —C(S)NR⁵R⁴, —S(O)₂NR⁵R⁴, —NR⁵C(O)R⁴, —NR⁵C(S)R⁴, —NR⁵S(O)₂R⁴, —NR⁵C(O)NH₂, —NR⁵C(O)NR⁵R⁴, —NR⁵C(S)NH₂, —NR⁵C(S)NR⁵R⁴, NR⁵S(O)₂NH₂, —NR⁵S(O)₂NR⁵R⁴, —S(O)R⁴, or —S(O)₂R⁴, optionally substituted lower alkynyl, provided, however, that when R⁴ is optionally substituted lower alkynyl, no alkyne carbon thereof is bound to N, S, O, S(O), S(O)₂, C(O) or C(S) of —OR⁴, —SR⁴— NR⁵R⁴, —C(O)R⁴, —C(S)R⁴, —C(O)OR⁴, —C(O)NR⁵R⁴, —C(S)NR⁵R⁴, S(O)₂NR⁵R⁴, —NR⁵C(O)R⁴, —NR⁵C(S)R⁴, —NR⁵S(O)₂R⁴, NR⁵C(O)NR⁵R⁴, —NR⁵C(S)NH₂, —NR⁵C(S)NR⁵R⁴, —NR⁵S(O)₂NH₂, —NR⁵S(O)₂NR⁵R⁴, —S(O)R⁴, or —S(O)₂R⁴, optionally substituted cycloalkyl, optionally substituted heterocycloalkyl, optionally substituted aryl, and optionally substituted heteroaryl; and R⁵ is selected from the group consisting of hydrogen and optionally substituted lower alkyl, provided, however, the compound is not

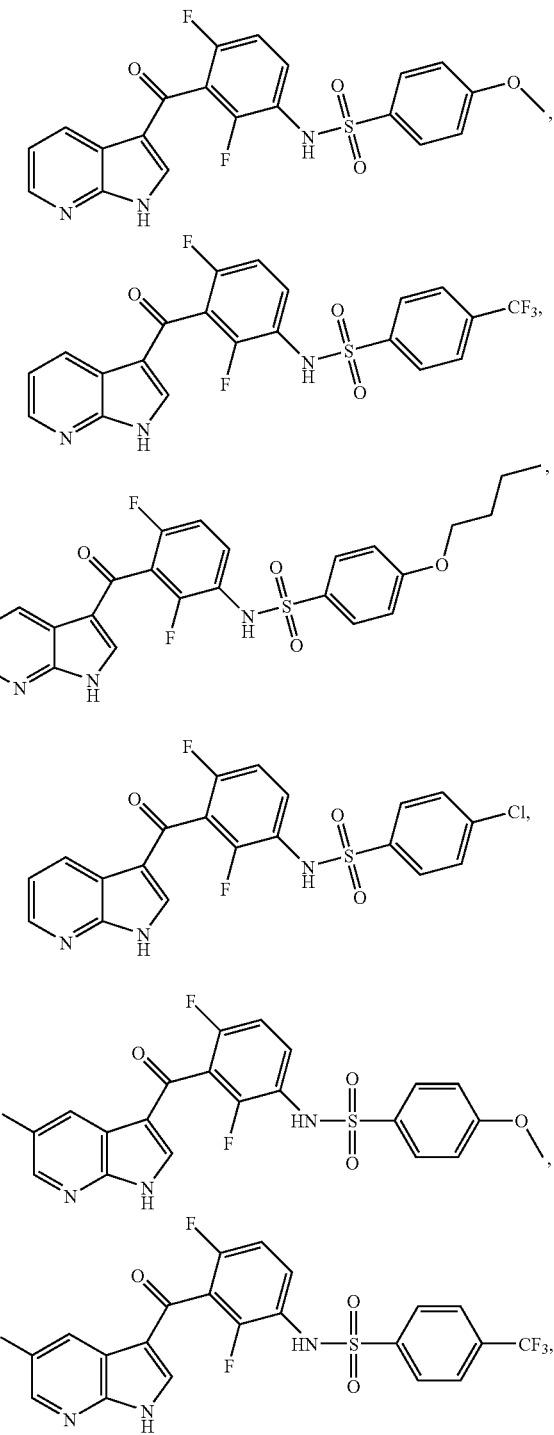

-continued
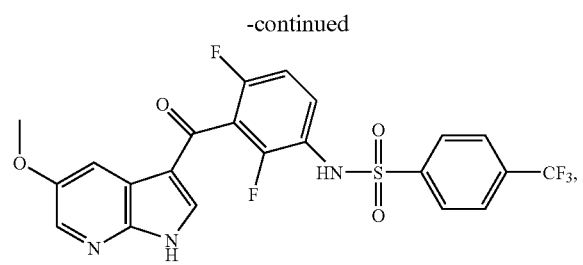
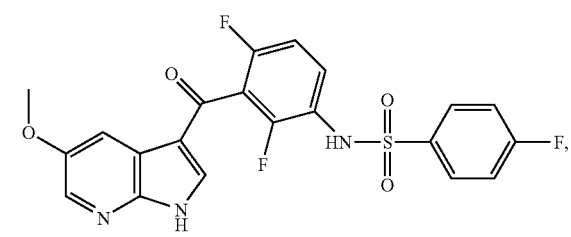
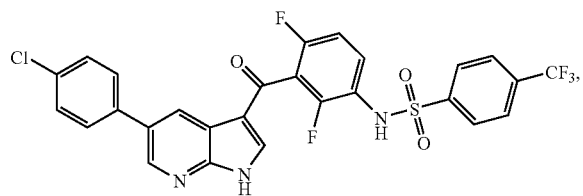
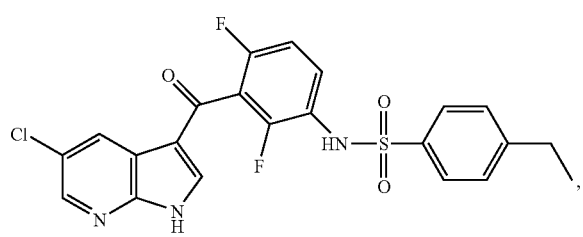
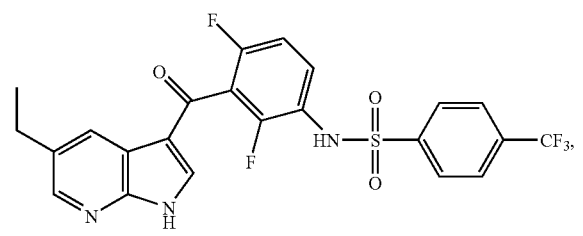
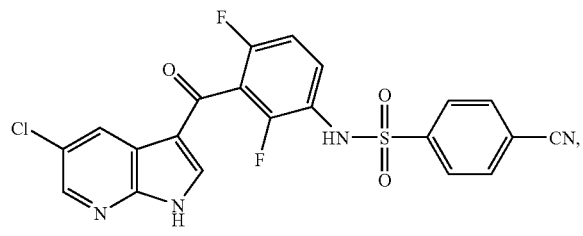
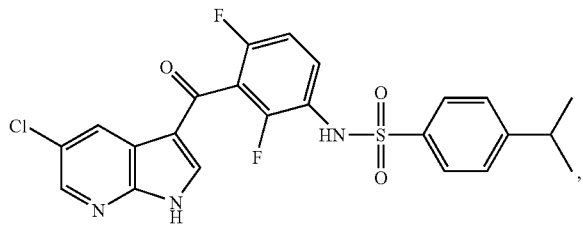
-continued
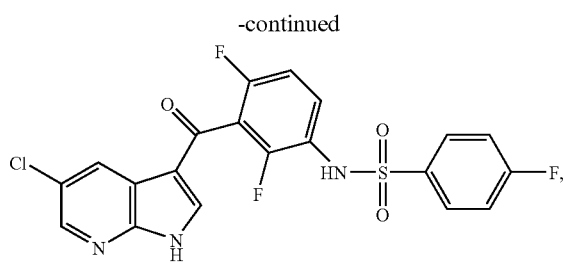
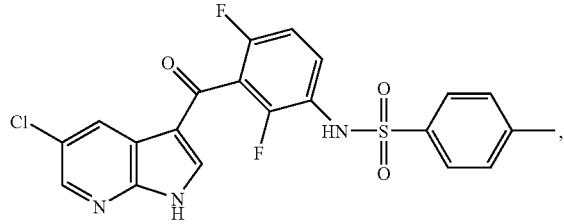
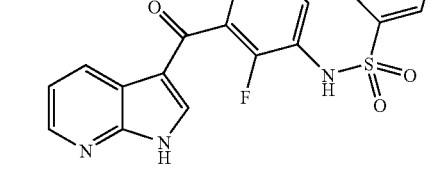
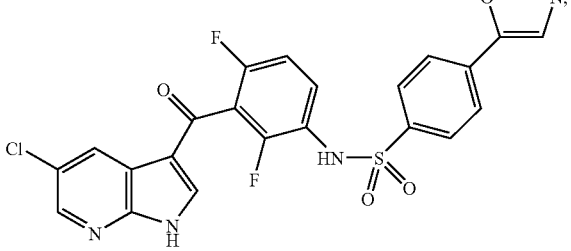
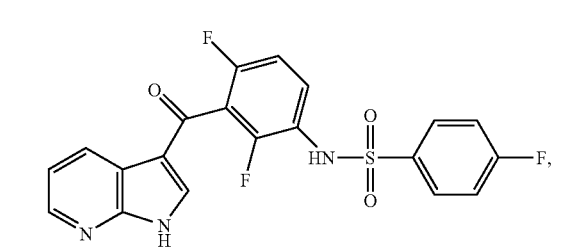
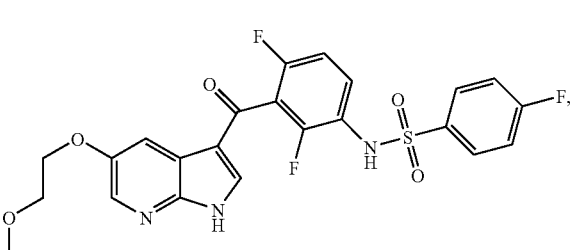
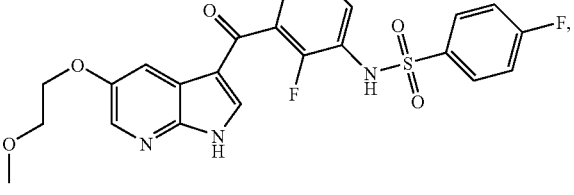

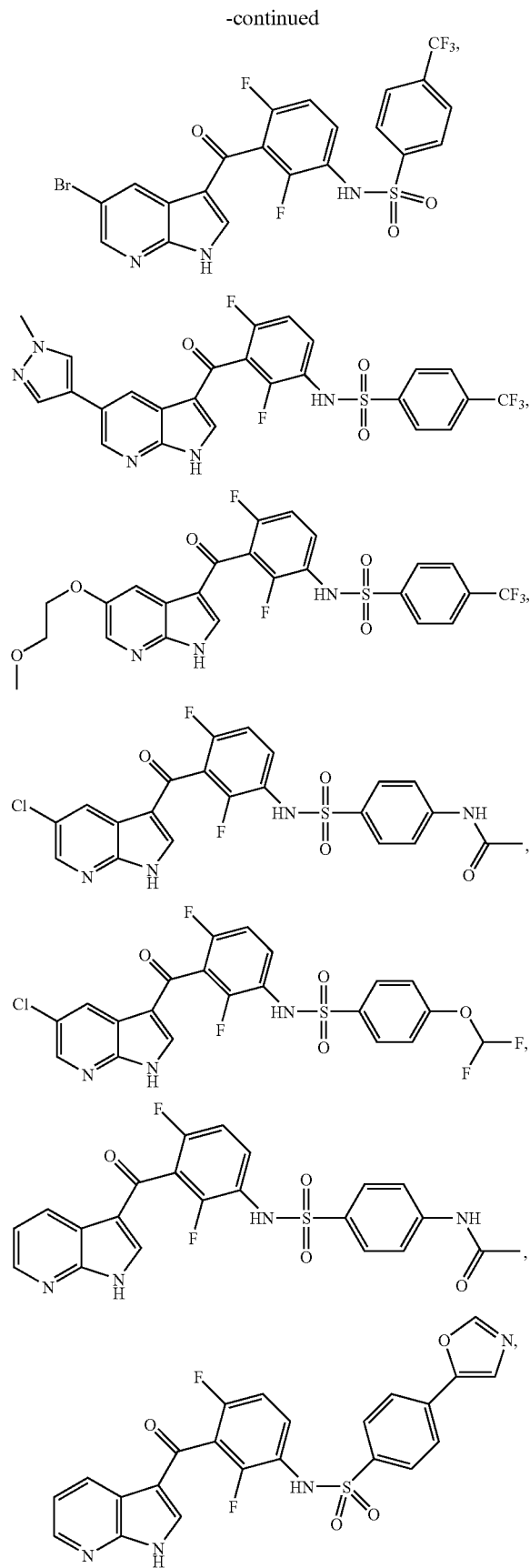

In some embodiments of compounds of Formula I, $R^1$ is selected from the group consisting of hydrogen, halogen, optionally substituted lower alkyl, optionally substituted cycloalkyl, optionally substituted heterocycloalkyl, optionally substituted aryl, optionally substituted heteroaryl, —CN, —$OR^4$, —$SR^4$—$NR^5R^4$, —$C(O)R^4$, —$C(O)NR^5R^4$, —$S(O)_2NR^5R^4$, —$NR^5C(O)R^4$, —$NR^5S(O)_2R^4$, —$S(O)R^4$, and —$S(O)_2R^4$, and $R^2$ is selected from the group consisting of halogen, optionally substituted lower alkyl, optionally substituted cycloalkyl, optionally substituted heterocycloalkyl, optionally substituted aryl, optionally substituted heteroaryl, —CN, —$OR^4$, —$SR^4$, —$NR^5R^4$, —$C(O)R^4$, —$C(O)NR^5R^4$, —$S(O)_2NR^5R^4$, —$NR^5C(O)R^4$, —$NR^5S(O)_2R^4$, —$S(O)R^4$, and —$S(O)_2R^4$.

In some embodiments of compounds of Formula I, $R^1$ is selected from the group consisting of hydrogen, halogen, lower alkyl, lower alkenyl, lower alkynyl, cycloalkyl, heterocycloalkyl, aryl, heteroaryl, —OH, —$NH_2$, —CN, —$NO_2$, —C(O)OH, —$S(O)_2NH_2$, —$C(O)NH_2$, —$C(S)NH_2$, —NHC(O)$NH_2$, —NHC(S)$NH_2$, —NHS(O)$_2NH_2$, —$OR^7$, —$SR^7$, —$NR^8R^7$, —$C(O)R^7$, —$C(S)R^7$, —$C(O)OR^7$, —$C(O)NR^8R^7$, —$C(S)NR^8R^7$, —$S(O)_2NR^8R^7$, —$NR^8C(O)R^7$, —$NR^8C(S)R^7$, —$NR^8S(O)_2R^7$, $R^8C(O)NH_2$, —$NR^8C(O)NR^8R^7$, —$NR^8C(S)NH_2$, —$NR^8C(S)NR^8R^7$, —$NR^8S(O)NH_2$, —$NR^8S(O)_2NR^8R^7$, —$S(O)R^7$, and —$S(O)_2R^7$, wherein lower alkyl, lower alkenyl or lower alkynyl are optionally substituted with one or more substituents selected from the group consisting of fluoro, —OH, —$NH_2$, C(O)OH, —$C(O)NH_7$, —$OR^7$, —$NR^8R^7$, —$C(O)OR^7$, —$C(O)NR^8R^7$, cycloalkyl, heterocycloalkyl, aryl, and heteroaryl, wherein cycloalkyl, heterocycloalkyl, aryl, and heteroaryl as $R^1$ or as substituents of lower alkyl, lower alkenyl or lower alkynyl are optionally substituted with one or more substituents selected from the group consisting of —OH, —$NH_2$, —CN, —$NO_2$, —$S(O)_2NH_2$, —$C(O)NH_2$, —$OR^9$, —$SR^9$, —$NR^8R^9$, —$NR^8C(O)R^9$, —$NR^8S(O)_2R^9$, —$S(O)_2R^9$, —$S(O)_2NR^8R^9$, —$C(O)R^9$, —$C(O)NR^8R^9$, halogen, lower alkyl, fluoro substituted lower alkyl, and cycloalkylamino; and $R^2$ is selected from the group consisting of halogen, lower alkyl, cycloalkyl, heterocycloalkyl, aryl, heteroaryl, —OH, —$NH_2$, —CN, —$NO_2$, —C(O)OH, —$S(O)_2NH_2$, —$C(O)NH_2$, —$C(S)NH_2$—NHC(O)$NH_2$, —NHC(S)$NH_2$, —NHS(O)$_2NH_2$, —$OR^7$, —$SR^7$, —$NR^8R^7$, —$C(O)R^7$, —$C(S)R^7$, —$C(O)OR^7$, —$C(O)NR^8R^7$, —$C(S)NR^8R^7$, —$S(O)_2NR^8R^7$, —$NR^8C(O)R^7$, —$NR^8C(S)R^7$, —$NR^8S(O)_2 R^7$, —$NR^8C(O)NH_2$, —$NR^8C(O)NR^8R^7$, —$NR^8C(S)NH_2$, —$NR^8C(S)NR^8R^7$, —$NR^8S(O)_2NH_2$, —$NR^8S(O)_2NR^8R^7$, —$S(O)R^7$, and —$S(O)_2R^7$, wherein lower-alkyl is optionally substituted with one or more substituents selected from the group consisting of fluoro, —OR⁷, —NR⁸R⁷, cycloalkyl, heterocycloalkyl, aryl, and heteroaryl, wherein cycloalkyl, heterocycloalkyl, aryl, and heteroaryl as R⁷ or as substituents of lower alkyl are optionally substituted with one or more substituents selected from the group consisting of —OH, —NH₂, —CN, —NO₂, —S(O)₂NH₂, —C(O)NH₂, —OR⁹, —SR⁹, —NR⁸R⁹, —NR⁸C(O)R⁹, —NR⁸S(O)₂R⁹, —S(O)₂R⁹, —S(O)₂NR⁸R⁹, —C(O)R⁹, —C(O)NR⁸R⁹, halogen, lower alkyl, fluoro substituted lower alkyl, and cycloalkylamino; wherein R⁷ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R⁷ or as substituents of lower alkyl are optionally substituted with one or more substituents selected from the group consisting of —OH, —NH₂, —CN, —NO₂, —S(O)₂NH₂, —C(O)NH₂, —OR⁹, —SR⁹, —NR⁸R⁹, —NR⁸C(O)R⁹, —NR⁸S(O)₂R⁹, —S(O)₂R⁹, —S(O)₂NR⁸R⁹, —C(O)R⁹, —C(O)NR⁸R⁹, halogen, lower alkyl, fluoro substituted lower alkyl, and cycloalkylamino; R⁸ at each occurrence is independently hydrogen or lower alkyl; and R⁹ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

In some embodiments of compounds of Formula I, R¹ is selected from the group consisting of hydrogen, —CN, —OR⁷, —SR⁷, —NR⁸R⁷, —NR⁸C(O)R⁷, —NR⁸S(O)₂R⁷, —C(O)NR⁸R⁷, —C(O)R⁷, —S(O)₂NR⁸R⁷, —S(O)R⁷, —S(O)₂R⁷, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R¹ or as substituents of lower alkyl are optionally substituted with one or more substituents selected from the group consisting of —OH, —N₂, —CN, —NO₂, —S(O)₂NH₂, —C(O)NH₂, —OR⁹, —SR⁹, —NR⁸R⁹, —NR⁸C(O)R⁹, —NR⁸S(O)₂R⁹, —S(O)₂R⁹, —S(O)₂NR⁸R⁹, —C(O)R⁹, —C(O)NR⁸R⁹, halogen, lower alkyl, fluoro substituted lower alkyl, and cycloalkylamino, and R² is selected from the group consisting of —CN, —OR⁷, —SR⁷, —NR⁸R⁷, —NR⁸C(O)R⁷, —NR⁸S(O)₂R⁷, —C(O)NR⁸R⁷, —C(O)R⁷, —S(O)₂NR⁸R⁷, —S(O)R⁷, —S(O)₂R⁷, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as R² or as a substituent of lower alkyl are optionally substituted with one or more substituents selected from the group consisting of —OH, —NH₂, —CN, —NO₂, —S(O)₂NH₂, —C(O)NH₂, —OR⁹, —SR⁹, —NR⁸R⁹, —NR⁸C(O)R⁹, —NR⁸S(O)₂R⁹, —S(O)₂R⁹, —S(O)₂NR⁸R⁹, —C(O)R⁹, —C(O)NR⁸R⁹, halogen, lower alkyl, fluoro substituted lower alkyl, and cycloalkylamino; wherein R⁷, R⁸ and R⁹ are as defined.

In some embodiments of compounds of Formula I, R¹ is hydrogen, —CN, —NR⁸R⁷, —OR⁷, —S(O)₂R⁷, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NR⁸R⁷, —OR⁷ and —S(O)₂R⁷, and R² is —CN, fluoro, chloro, lower alkyl, fluoro substituted lower alkyl, —NR⁸R⁷, —OR⁷ or —S(O)₂R⁷; wherein R⁷ and R⁸ are as defined.

In some embodiments of compounds of Formula I, R¹ is hydrogen, —CN, fluoro, chloro, lower alkyl, fluoro substituted lower alkyl, lower alkoxy, fluoro substituted lower alkoxy, lower alkoxy substituted C₂₋₆ alkoxy, aryl or heteroaryl, wherein aryl or heteroaryl are optionally substituted with one or more substituents selected from the group consisting of fluoro, chloro, lower alkyl, fluoro substituted lower alkyl, lower alkoxy, fluoro substituted lower alkoxy, monoalkylamino, di-alkylamino, and cycloalkylamino, and R² is —CN, fluoro, chloro, lower alkyl, fluoro substituted lower alkyl, lower alkoxy, fluoro substituted lower alkoxy, monoalkylamino, di-alkylamino, or cycloalkylamino.

In one embodiment of compounds of Formula I, the compound is selected from the group consisting of:

4-Butoxy-N-[3-(5-chloro-1H-pyrrolo[2,3-b]pyridine-3-carbonyl)-2,4-difluoro-phenyl]-benzenesulfonamide (P-0007), N-[3-(5-Chloro-1H-pyrrolo[2,3-b]pyridine-3-carbonyl)-2,4-difluoro-phenyl]-4-pyrazol-1-yl-benzenesulfonamide (P-0008), N-[3-(5-Chloro-1H-pyrrolo[2,3-b]pyridine-3-carbonyl)-2,4-difluoro-phenyl]-4-isopropoxy-benzenesulfonamide (P-0011), 4-tert-Butyl-N-[3-(5-chloro-1H-pyrrolo[2,3-b]pyridine-3-carbonyl)-2,4-difluoro-phenyl]-benzenesulfonamide (P-0014), N-[3-(5-Chloro-1H-pyrrolo[2,3-b]pyridine-3-carbonyl)-2,4-difluoro-phenyl]-4-propyl-benzenesulfonamide (P-0015), N-{2,4-Difluoro-3-[5-(2-methoxy-ethoxy)-1H-pyrrolo[2,3-b]pyridine-3-carbonyl]-phenyl}-4-isopropyl-benzenesulfonamide (P-0018), N-{2,4-Difluoro-3-[5-(4-methyl-1H-imidazol-2-yl)-1H-pyrrolo[2,3-b]pyridine-3-carbonyl]-phenyl}-4-isopropyl-benzenesulfonamide (P-0019), 4-Difluoromethoxy-N-{2,4-difluoro-3-[5-(1-methyl-1H-pyrazol-4-yl)-1H-pyrrolo[2,3-b]pyridine-3-carbonyl]-phenyl}-benzenesulfonamide (P-0020), N-{2,4-Difluoro-3-[5-(1-methyl-1H-pyrazol-4-yl)-1H-pyrrolo[2,3-b]pyridine-3-carbonyl]-phenyl}-4-propyl-benzenesulfonamide (P-0021), N-{2,4-Difluoro-3-[5-(1-methyl-1H-pyrazol-4-yl)-1H-pyrrolo[2,3-b]pyridine-3-carbonyl]-phenyl}-4-isopropyl-benzenesulfonamide (P-0022), N-{2,4-Difluoro-3-[5-(5-methyl-1H-imidazol-2-yl)-1H-pyrrolo[2,3-b]pyridine-3-carbonyl]-phenyl}-4-propyl-benzenesulfonamide (P-0023), N-{2,4-Difluoro-3-[5-(5-methyl-1H-imidazol-2-yl)-1H-pyrrolo[2,3-b]pyridine-3-carbonyl]-phenyl}-4-trifluoromethyl-benzenesulfonamide (P-0025), N-{2,4-Difluoro-3-[5-(1-methyl-1H-imidazol-2-yl)-1H-pyrrolo[2,3-b]pyridine-3-carbonyl]-phenyl}-4-propyl-benzenesulfonamide (P-0026),
N-{3-[5-(1,5-Dimethyl-1H-imidazol-2-yl)-1H-pyrrolo[2,3-b]pyridine-3-carbonyl]-2,4-difluorophenyl}-4-propyl-benzenesulfonamide (P-0027),
N-[2,4-Difluoro-3-(5-methyl-1H-pyrrolo[2,3-b]pyridine-3-carbonyl)-phenyl]-4-trifluoromethyl-benzenesulfonamide (P-0030),
N-[3-(5-Cyano-1H-pyrrolo[2,3-b]pyridine-3-carbonyl)-2,4-difluoro-phenyl]-4-trifluoromethyl-benzenesulfonamide (P-0031),
(E)-3-{3-[2,6-Difluoro-3-(4-trifluoromethyl-benzenesulfonylamino)-benzoyl]-1H-pyrrolo[2,3-b]pyridin-5-yl}-acrylic acid methyl ester (P-0032),
3-{3-[2,6-Difluoro-3-(4-trifluoromethyl-benzenesulfonylamino)-benzoyl]-1H-pyrrol[2,3-b]pyridin-5-yl}-propionic acid methyl ester (P-0033),
3-{3-[2,6-Difluoro-3-(4-trifluoromethyl-benzenesulfonylamino)-benzoyl]-1H-pyrrolo[2,3-b]pyridin-5-yl}-propionic acid (P-0034),
3-{3-[2,6-Difluoro-3-(4-trifluoromethyl-benzenesulfonylamino)-benzoyl]-1H-pyrrolo[2,3-b]pyridin-5-yl}-N-ethyl-propionamide (P-0035) and all salts, prodrugs, tautomers, and isomers thereof.

In some embodiments, compounds have the structure according to the following Formula II:

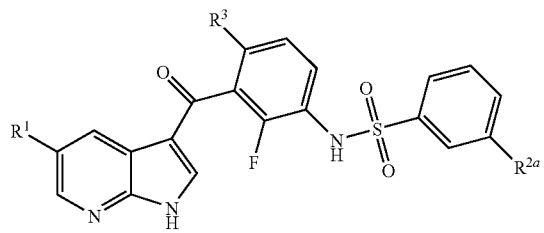

Formula II all salts, prodrugs, tautomers and isomers thereof,
wherein:
R$^{2a}$ is as defined for R$^2$ for Formula I; and
R$^1$ and R$^3$ are as defined for Formula I, provided, however, the compound is not

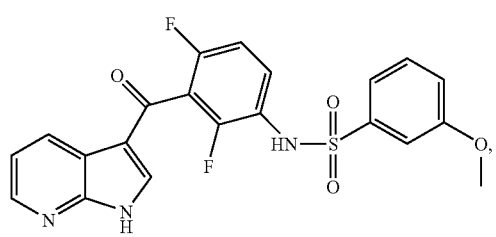

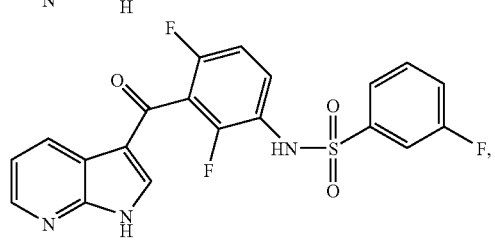

-continued

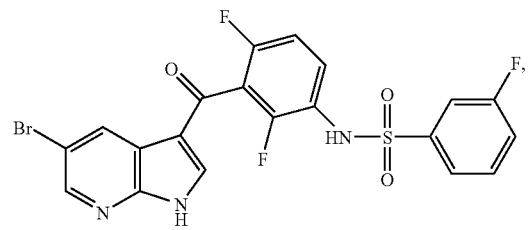

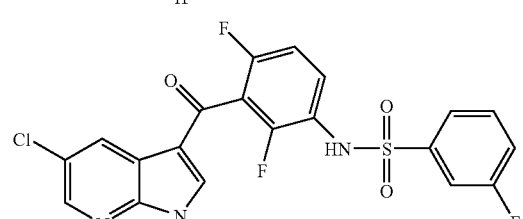

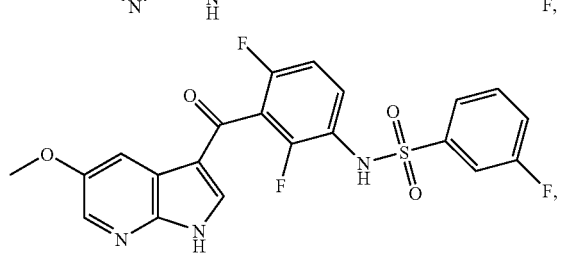

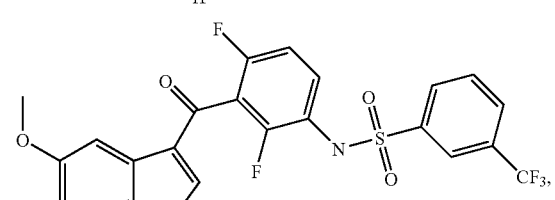

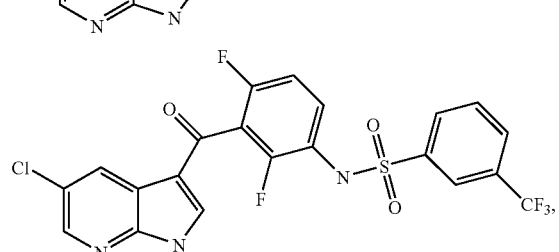

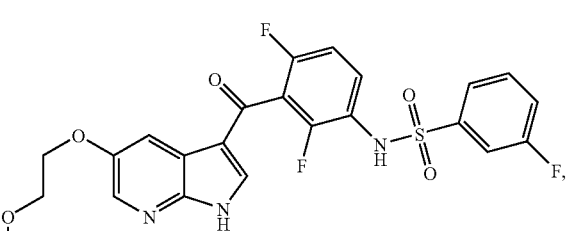

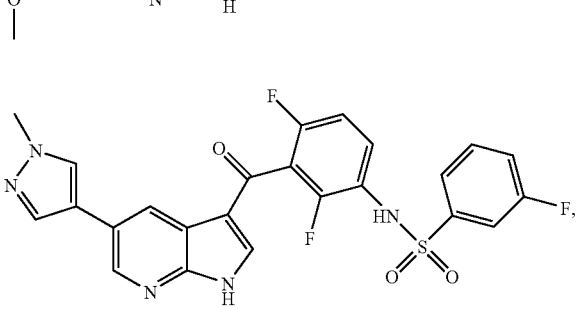

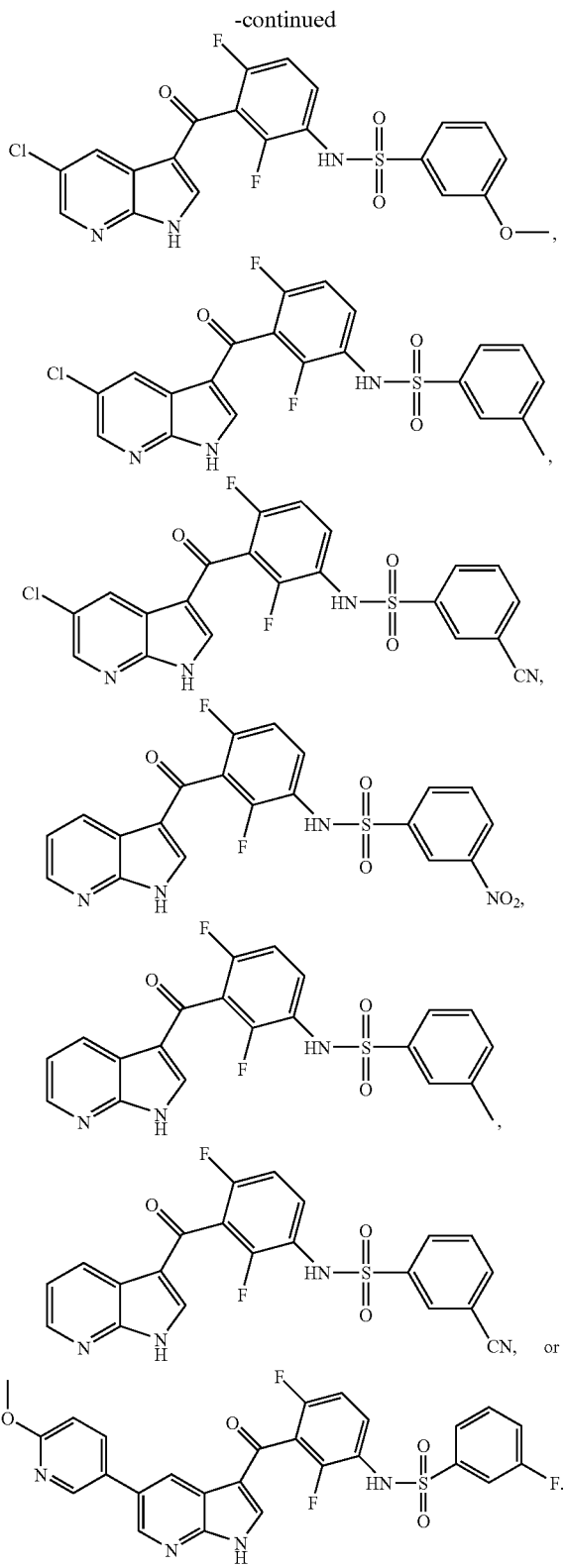

—OR⁴, —SR⁴, —NR⁵R⁴, —C(O)R⁴, —C(O)NR⁵R⁴, —S(O)₂NR⁵R⁴, —NR⁵C(O)R⁴, —NR⁵S(O)₂R⁴, —S(O)R⁴, and —S(O)₂R⁴, and R²ᵃ is selected from the group consisting of halogen, optionally substituted lower alkyl, optionally substituted cycloalkyl, optionally substituted heterocycloalkyl, optionally substituted aryl, optionally substituted heteroaryl, —CN, —OR⁴, —SR⁴, —NR⁵R⁴, —C(O)R⁴, —C(O)NR⁵R⁴, —S(O)₂NR⁵R⁴, —NR⁵C(O)R⁴, —NR⁵S(O)₂R⁴, —S(O)R⁴, and —S(O)₂R⁴.

In some embodiments of compounds of Formula II, R¹ is selected from the group consisting of hydrogen, halogen, lower alkyl, lower alkenyl, lower alkynyl, cycloalkyl, heterocycloalkyl, aryl, heteroaryl, —OH, —NH₂, —CN, —NO₂, —C(O)OH, —S(O)₂NH₂, —C(O)NH₂, —C(S)NH₂, —NHC(O)NH₂, —NHC(S)NH₂, —NHS(O)₂NH₂, —OR⁷, —SR⁷, —NR⁸R⁷, —C(O)R⁷, —C(S)R⁷, —C(O)OR⁷, —C(O)NR⁸R⁷, —C(S)NR⁸R⁷, —S(O)₂NR⁸R⁷, —NR⁸C(O)R⁷, —NR⁸C(S)R⁷, —NR⁸S(O)₂R⁷, —NR⁸C(O)NH₂, —NR⁸C(O)NR⁸R⁷, —NR⁸C(S)NH₂, —NR⁸C(S)NR⁸R⁷, —NR⁸S(O)₂NH₂, —NR⁸S(O)₂NR⁸R⁷, —S(O)R⁷, and —S(O)₂R⁷, wherein lower alkyl, lower alkenyl or lower alkynyl are optionally substituted with one or more substituents selected from the group consisting of fluoro, —OH, —NH₂, —C(O)OH, —C(O)NH₂, —OR⁷, —NR⁸R⁷, —C(O)OR⁷, —C(O)NR⁸R⁷, cycloalkyl, heterocycloalkyl, aryl, and heteroaryl, wherein cycloalkyl, heterocycloalkyl, aryl, and heteroaryl as R¹ or as substituents of lower alkyl, lower alkenyl or lower alkynyl are optionally substituted with one or more substituents selected from the group consisting of —OH, —NH—, —CN, —NO₂, —S(O)₂NH₂, —C(O)NH₂, —OR⁹, —SR⁹, —NR⁸R⁹, —NR⁸C(O)R⁹, —NR⁸S(O)₂R⁹, —S(O)₂R⁹, —S(O)₂NR⁸R⁹, —C(O)R⁹, —C(O)NR⁸R⁹, halogen, lower alkyl, fluoro substituted lower alkyl, and cycloalkylamino; and R²ᵃ is selected from the group consisting of halogen, lower alkyl, cycloalkyl, heterocycloalkyl, aryl, heteroaryl, —OH, —NH₂, —CN, —NO₂, —C(O)OH, —S(O)₂NH₂, —C(O)NH₂, —C(S)NH₂, —NHC(O)NH₂, —NHC(S)NH₂, —NHS(O)₂NH₂, —OR⁷, —SR⁷, —NR⁸R⁷, —C(O)R⁸R⁷, —C(S)R⁷, —C(O)OR⁷, —C(O)NR⁸R⁷, —C(S)NR⁸R⁷, —S(O)₂NR⁸R⁷, —NR⁸C(O)R⁷, —NR⁸C(S)R⁷, —NR⁸S(O)₂R⁷, —NR⁸C(O)NH₂, —NR⁸C(O)NR⁸R⁷, —NR⁸C(S)NH₂, —NR⁸C(S)NR⁸R⁷, —NR⁸S(O)₂NH₂, —NR⁸S(O)₂NR⁸R⁷, —S(O)R⁷, and —S(O)₂R⁷, wherein lower alkyl is optionally substituted with one or more substituents selected from the group consisting of fluoro, —OR⁷, —NR⁸R⁷, cycloalkyl, heterocycloalkyl, aryl, and heteroaryl, wherein cycloalkyl, heterocycloalkyl, aryl, and heteroaryl as R²ᵃ or as substituents of lower alkyl are optionally substituted with one or more substituents selected from the group consisting of —OH, —NH₂, —CN, —NO₂, —S(O)₂NH₂, —C(O)NH₂, —OR⁹, —SR⁹, —NR⁸R⁹, —NR⁸C(O)R⁹, —NR⁸S(O)₂R⁹, —S(O)₂R⁹, —S(O)₂NR⁸R⁹, —C(O)R⁹, —C(O)NR⁸R⁹, halogen, lower alkyl, fluoro substituted lower alkyl, and cycloalkylamino; wherein R⁷ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R⁷ or as substituents of lower alkyl are optionally substituted with one or more substituents selected from the group consisting of —OH, —NH₂, —CN, —NO₂, —S(O)₂NH₂, —C(O)NH₂, —OR⁹, —SR⁹, —NR⁸R⁹, —NR⁸C(O)R⁹, —NR⁸S(O)₂R⁹, —S(O)₂R⁹, —S(O)₂NR⁸R⁹, —C(O)R⁹, —C(O)NR⁸R⁹, halogen, lower alkyl, In some embodiments of compounds of Formula II, R¹ is selected from the group consisting of hydrogen, halogen, optionally substituted lower alkyl, optionally substituted cycloalkyl, optionally substituted heterocycloalkyl, optionally substituted aryl, optionally substituted heteroaryl, —CN, fluoro substituted lower alkyl, and cycloalkylamino; $R^8$ at each occurrence is independently hydrogen or lower alkyl; and $R^9$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino; and heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

In some embodiments of compounds of Formula II, $R^1$ is selected from the group consisting of hydrogen, —CN, —OR$^7$, —SR$^7$, —NR$^8$R$^7$, —NR$^8$C(O)R$^7$, —NR$^8$S(O)$_2$R$^7$, —C(O)NR$^8$R$^7$, —C(O)R$^7$, —S(O)$_2$NR$^8$R$^7$, —S(O)R$^7$, —S(O)$_2$R$^7$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^1$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NR$^8$R$^9$, —NR$^5$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino; and $R^{2a}$ is selected from the group consisting of —CN, —OR$^7$, —SR$^7$, —NR$^8$R$^7$, —NR$^8$C(O)R$^7$, —NR$^8$S(O)$_2$R$^7$, —C(O)NR$^8$R$^7$, —C(O)R$^7$, —S(O)$_2$NR$^8$R$^7$, —S(O)R$^7$, —C(O)$_2$R$^7$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{2a}$ or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)NR$^8$R$^9$, —C(O)NR$^8$R$^9$, halogen, lower alkyl, fluoro substituted lower alkyl, and cycloalkylamino; wherein $R^7$, $R^8$ and $R^9$ are as defined.

In some embodiments of compounds of Formula II, $R^1$ is hydrogen, —CN, —NR$^8$R$^7$, —OR$^7$, —S(O)$_2$R$^7$, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^8$R$^7$, —OR$^7$ and —S(O)$_2$R$^7$, and $R^{2a}$ is —CN, fluoro, chloro, lower alkyl, fluoro substituted lower alkyl, —NR$^8$R$^7$, —OR$^7$ or —S(O)$_2$R$^7$; wherein $R^7$ and $R^8$ are as defined.

In some embodiments of compounds of Formula II, $R^1$ is hydrogen, —CN, fluoro, chloro, lower alkyl, fluoro substituted lower alkyl, lower alkoxy, fluoro substituted lower alkoxy, lower alkoxy substituted $C_{2-6}$ alkoxy, aryl or heteroaryl, wherein aryl or heteroaryl are optionally substituted with one or more substituents selected from the group consisting of fluoro, chloro, lower alkyl, fluoro substituted lower alkyl, lower alkoxy, fluoro substituted lower alkoxy, mono-alkylamino, di-alkylamino, and cycloalkylamino, and $R^{2a}$ is —CN, fluoro, chloro, lower alkyl, fluoro substituted lower alkyl, lower alkoxy, fluoro substituted lower alkoxy, mono-alkylamino, di-alkylamino, or cycloalkylamino.

In one embodiment of compounds of Formula II, the compound is selected from the group consisting of:

3-[3-(5-Chloro-1H-pyrrolo[2,3-b]pyridine-3-carbonyl)-2,4-difluoro-phenylsulfamoyl]-benzoic acid (P-0004), N-[3-(5-Chloro-1H-pyrrolo[2,3-b]pyridine-3-carbonyl)-2,4-difluoro-phenyl]-3-difluoromethoxy-benzenesulfonamide (P-0016), 3-Difluoromethoxy-N-{2,4-difluoro-3-[5-(5-methyl-1H-imidazol-2-yl)-1H-pyrrolo[2,3-b]pyridine-3-carbonyl]-phenyl}-benzenesulfonamide (P-0024) and all salts, prodrugs, tautomers, and isomers thereof.

In some embodiments, compounds have the structure according to the following Formula III:

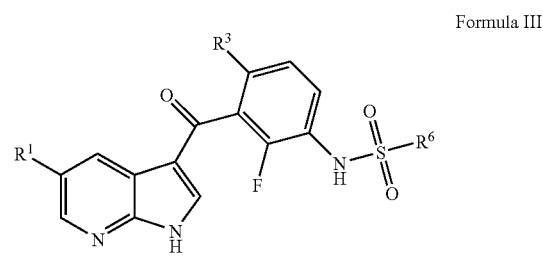

Formula III all salts, prodrugs, tautomers and isomers thereof:
wherein:
$R^1$ and $R^3$ are as defined for Formula I; and
$R^6$ is optionally substituted heteroaryl, provided, however, the compound is not

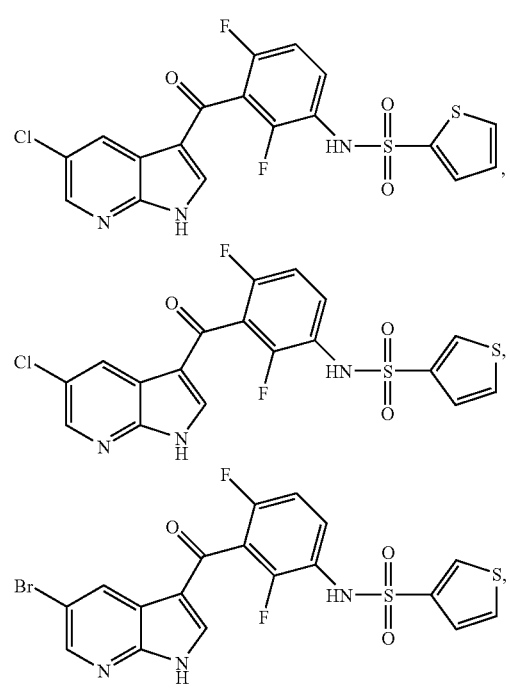

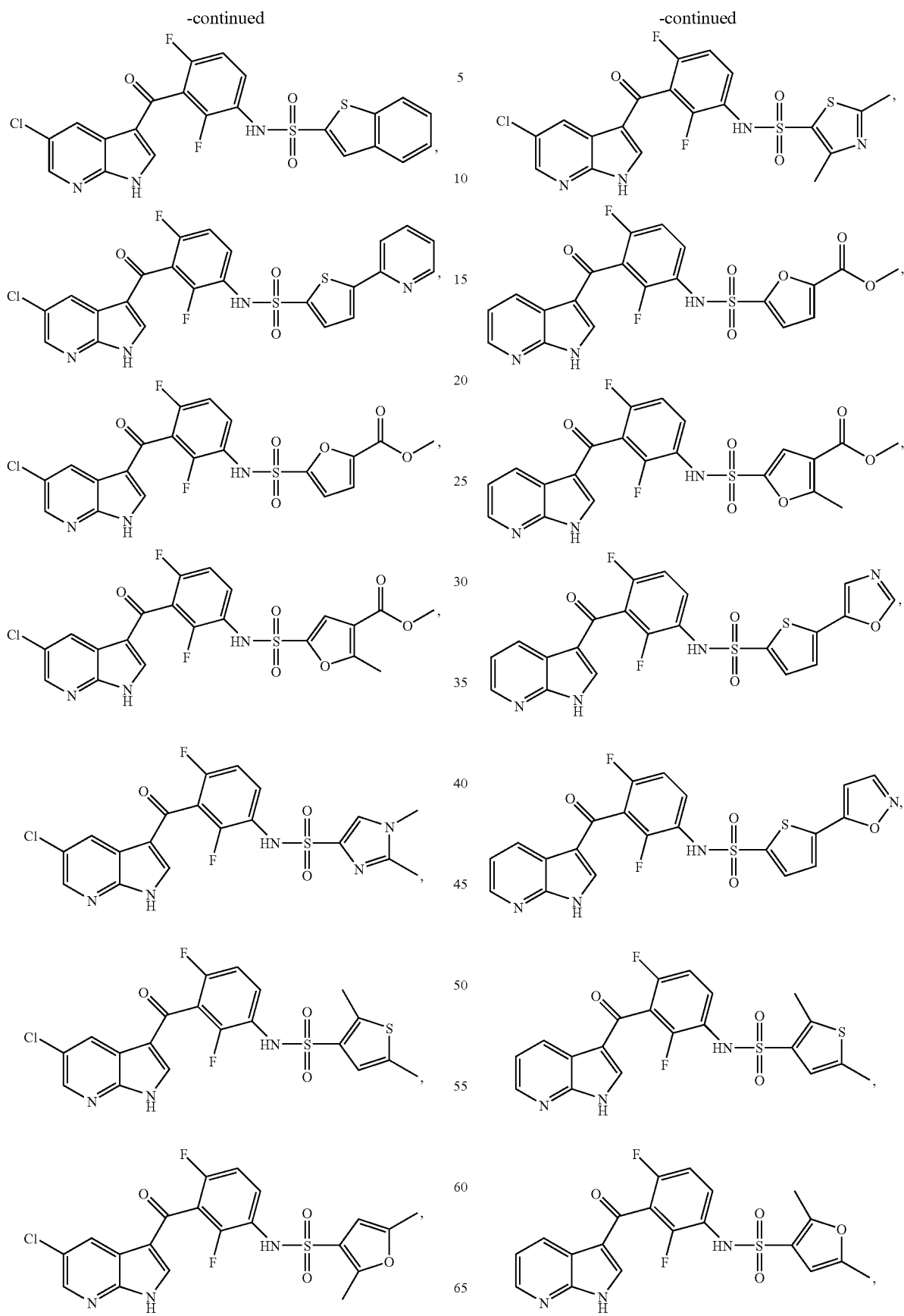

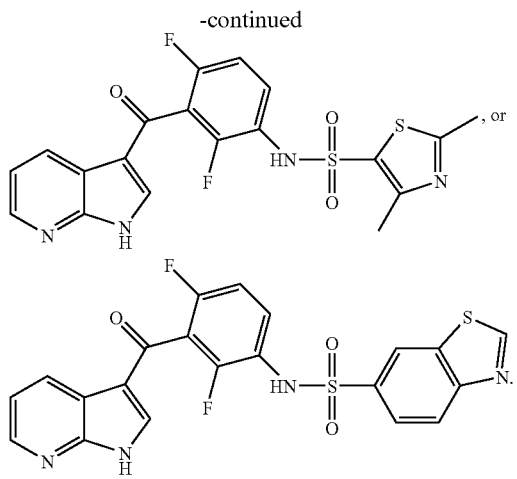

In some embodiments of compounds of Formula III, $R^1$ is selected from the group consisting of hydrogen, halogen, optionally substituted lower alkyl, optionally substituted cycloalkyl, optionally substituted heterocycloalkyl, optionally substituted aryl, optionally substituted heteroaryl, —CN, —OR$^4$, —SR$^4$, —NR$^5$R$^4$, —C(O)R$^4$, —C(O)NR$^5$R$^4$, —S(O)$_2$NR$^5$R$^4$, —NR$^5$C(O)R$^4$, —NR$^5$S(O)$_2$R$^4$, —S(O)R$^4$, and —S(O)$_2$R$^4$, and $R^6$ is heteroaryl optionally substituted with one or more substituents selected from the group consisting of halogen, optionally substituted lower alkyl, optionally substituted cycloalkyl, optionally substituted heterocycloalkyl, optionally substituted aryl, optionally substituted heteroaryl, —CN, —OR$^4$, —SR$^4$, —NR$^5$R$^4$, —C(O)R$^4$, —C(O)NR$^5$R$^4$, —S(O)$_2$NR$^5$R$^4$, —NR$^5$C(O)R$^4$, —NR$^5$S(O)$_2$R$^4$, —S(O)R$^4$, and —S(O)$_2$R$^4$, where $R^4$ and $R^5$ are as defined for Formula I.

In some embodiments of compounds of Formula III, $R^1$ is selected from the group consisting of hydrogen, halogen, lower alkyl, lower alkenyl, lower alkynyl, cycloalkyl, heterocycloalkyl, aryl, heteroaryl, —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH, —OR$^7$, —SR$^7$, —NR$^8$R$^7$, —C(O)R$^7$, —C(S)R$^7$, —C(O)OR$^7$—C(O)NR$^8$R$^7$, —C(S)NR$^8$R$^7$, —S(O)$_2$NR$^8$R$^7$, —NR$^8$C(O)R$^7$, —NR$^8$C(S)R$^7$, —NR$^8$S(O)$_2$R$^7$, —NR$^8$C(O)NH$_2$, —NR$^8$C(O)NR$^8$R$^7$, —NR$^8$C(S)NH$_2$, —NR$^8$C(S)NR$^8$R$^7$, —NR$^8$S(O)NH$_2$, —NR$^8$S(O)$_2$NR$^8$R$^7$, —S(O)R$^7$, and —S(O)$_2$R$^7$, wherein lower alkyl, lower alkenyl or lower alkynyl are optionally substituted with one or more substituents selected from the group consisting of fluoro, —OH, —NH$_2$, C(O)OH, —C(O)NH$_2$, —OR$^7$, —NR$^8$R$^7$, —C(O)OR$^7$, —C(O)NR$^8$R$^7$, cycloalkyl, heterocycloalkyl, aryl, and heteroaryl, wherein cycloalkyl, heterocycloalkyl, aryl, and heteroaryl as $R^1$ or as substituents of lower alkyl, lower alkenyl or lower alkynyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)R$^8$R$^9$, halogen, lower alkyl, fluoro substituted lower alkyl, and cycloalkylamino; and $R^6$ is heteroaryl optionally substituted with one or more substituents selected from the group consisting of halogen, lower alkyl, cycloalkyl, heterocycloalkyl, aryl, heteroaryl, —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^7$, —SR$^7$, —NR$^8$R$^7$, —C(O)R$^7$, —C(S)R$^7$, —C(O)OR$^7$, —C(O)NR$^8$R$^7$, —C(S)NR$^8$R$^7$, —S(O)$_2$NR$^8$R$^7$, —NR$^8$C(O)R$^7$, —NR$^8$C(S)R$^7$, —NR$^8$S(O)$_2$R$^7$, —NR$^8$C(O)NH$_2$, —NR$^8$C(O)NR$^8$R$^7$, —NR$^8$C(S)NH$_2$, —NR$^8$C(S)NR$^8$R$^7$, —NR$^8$S(O)$_2$NH$_2$, —NR$^8$S(O)$_2$NR$^8$R$^7$, —S(O)R$^7$, and S(O)$_2$R$^7$, wherein lower alkyl is optionally substituted with one or more substituents selected from the group consisting of fluoro, —OR$^7$, —NR$^8$R$^7$, cycloalkyl, heterocycloalkyl, aryl, and heteroaryl, wherein cycloalkyl, heterocycloalkyl, aryl, and heteroaryl as a substituent of $R^6$ or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino; wherein $R^7$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^7$ or as substituents of lower alkyl are optionally substituted with one or more substituents selected from the group consisting of —OH, —NH$_2$, —CN, —NO$_2$, —S(O)$_2$NH$_2$, —C(O)NH, —OR$^9$, —SR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino; $R^8$ at each occurrence is independently hydrogen or lower alkyl; and $R^9$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

In some embodiments of compounds of Formula III, $R^1$ is selected from the group consisting of hydrogen, —CN, —OR$^7$, —SR$^7$, —NR$^8$R$^7$, —NR$^8$C(O)R$^7$, —NR$^8$S(O)$_2$R$^7$, —C(O)NR$^8$R$^7$, —C(O)R$^7$, —S(O)$_2$NR$^8$R$^7$, —S(O)R$^7$, —S(O)$_2$R$^7$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^1$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NR$^8$R$^9$, —NR$^8$C(O)R$^7$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino; and $R^6$ is heteroaryl optionally substituted with one or more substituents selected from the group consisting of —CN, —OR$^7$, —SR$^7$, —NR$^8$R$^7$, —NR$^8$C(O)R$^7$, —NR$^8$S(O)$_2$R$^7$, —C(O)NR$^4$R$^7$, —C(O)R$^7$, —S(O)$_2$NR$^8$R$^7$, —S(O)R$^7$, —S(O)$_2$R$^7$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as a substituent of $R^6$ or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino; wherein $R^7$, $R^8$ and $R^9$ are as defined.

In some embodiments of compounds of Formula III, $R^1$ is hydrogen, —CN, —NR$^8$R$^7$, —OR$^7$, —S(O)$_2$R$^7$, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^8$R$^7$, —OR$^7$ and —S(O)$_2$R$^7$, and $R^6$ is heteroaryl optionally substituted with one or more of —CN, fluoro, chloro, lower alkyl, fluoro substituted lower alkyl, —NR$^8$R$^7$, —OR$^7$ or —S(O)$_2$R$^7$; wherein $R^7$ and $R^8$ are as defined.

In some embodiments of compounds of Formula III, $R^1$ is hydrogen, —CN, fluoro, chloro, lower alkyl, fluoro substituted lower alkyl, lower alkoxy, fluoro substituted lower alkoxy, lower alkoxy substituted $C_{2-6}$ alkoxy, aryl or heteroaryl, wherein aryl or heteroaryl are optionally substituted with one or more substituents selected from the group consisting of fluoro, chloro, lower alkyl, fluoro substituted lower alkyl, lower alkoxy, fluoro substituted lower alkoxy, mono-alkylamino, di-alkylamino, and cycloalkylamino, and $R^6$ is heteroaryl optionally substituted with one or more of —CN, fluoro, chloro, lower alkyl, fluoro substituted lower alkyl, lower alkoxy, fluoro substituted lower alkoxy, mono-alkylamino, di-alkylamino, or cycloalkylamino.

In one embodiment of compounds of Formula III, the compound is selected from the group consisting of:

Benzo[b]thiophene-3-sulfonic acid [3-(5-chloro-1H-pyrrolo[2,3-b]pyridine-3-carbonyl)-2,4-difluoro-phenyl]-amide (P-0001), 5-Methyl-2-trifluoromethyl-furan-3-sulfonic acid [3-(5-chloro-1H-pyrrolo[2,3-b]pyridine-3-carbonyl)-2,4-difluoro-phenyl]-amide (P-0002), 5-Oxazol-5-yl-thiophene-2-sulfonic acid [3-(5-chloro-1H-pyrrolo[2,3-b]pyridine-3-carbonyl)-2,4-difluoro-phenyl]-amide (P-0003), 2-Oxo-2H-chromene-6-sulfonic acid [3-(5-chloro-1H-pyrrolo[2,3-b]pyridine-3-carbonyl)-2,4-difluoro-phenyl]-amide (P-0005), 5-Isoxazol-5-yl-thiophene-2-sulfonic acid [3-(5-chloro-1H-pyrrolo[2,3-b]pyridine-3-carbonyl)-2,4-difluoro-phenyl]-amide (P-0006), Benzothiazole-6-sulfonic acid [3-(5-chloro-1H-pyrrolo[2,3-b]pyridine-3-carbonyl)-2,4-difluoro-phenyl]-amide (P-0009), 1-Methyl-3-trifluoromethyl-1H-pyrazole-4-sulfonic acid [3-(5-chloro-1H-pyrrolo[2,3-b]pyridine-3-carbonyl)-2,4-difluoro-phenyl]-amide (P-0010), Benzo[1,2,5]thiadiazoe-5-sulfonic acid [3-(5-chloro-1H-pyrrolo[2,3-b]pyridine-3-carbonyl)-2,4-difluoro-phenyl]-amide (P-0013), 5-Methyl-benzo[b]thiophene-2-sulfonic acid [3-(5-chloro-1H-pyrrolo[2,3-b]pyridine-3-carbonyl)-2,4-difluoro-phenyl]-amide (P-0017), 5-Methyl-thiophene-2-sulfonic acid [3-(5-chloro-1H-pyrrolo[2,3-b]pyridine-3-carbonyl)-2,4-difluoro-phenyl]-amide (P-0028), 1-Methyl-1H-pyrazole-3-sulfonic acid [3-(5-chloro-1H-pyrrolo[2,3-b]pyridine-3-carbonyl)-2,4-difluoro-phenyl]-amide (P-0029), Pyridine-2-sulfonic acid [2,4-difluoro-3-(5-methoxy-1H-pyrrolo[2,3-b]pyridine-3-carbonyl)-phenyl]-amide (P-0036) and all salts, prodrugs, tautomers, and isomers thereof.

In some embodiments of the above compounds, compounds are excluded where N (except where N is a heteroaryl ring atom), O, or S is bound to a carbon that is also bound to N (except where N is a heteroaryl ring atom), O, or S; or where N (except where N is a heteroaryl ring atom), O, C(S), C(O), or S(O)$_n$ (n is 0-2) is bound to an alkene carbon of an alkenyl group or bound to an alkyne carbon of an alkynyl group; accordingly, in some embodiments compounds which include linkages such as the following are excluded from the compounds provided: —NR—C$_2$—NR—, —O—CH$_2$—NR—, —S—CH$_2$—NR—, —NR—CH, —O—, —O—CH$_2$—O—, —S—CH$_2$—O—, —NR—CH, —S—, —O—CH$_2$—S—, —S—CH$_2$—S—, —NR—CH=CH—, —CH=CH—NR—, —NR—C≡C—, —C≡C—NR—, —O—CH=CH—, —CH=CH—O—, —O—C≡C—, —C≡C—O—, —S(O)$_{0-2}$—CH=CH—, —CH=CH—S(O)$_{0-2}$—, —S(O)$_{0-2}$—C≡C—, —C≡C—S(O)$_{0-2}$—, —C(O)—CH=CH—, —CH=CH—C(O)—, —C≡C—C(O)—, or —C(O)—C≡C—, —C(S)—CH=CH—, —CH=CH—C(S)—, —C≡C—C(S)—, or —C(S)—C≡C—.

In reference to compounds herein, unless clearly indicated to the contrary, specification of a compound or group of compounds includes pharmaceutically acceptable salts of such compound(s), prodrug(s), and all stereoisomers thereof. In reference to compositions, kits, methods of use, etc. of compounds of Formula I, Formula II, or Formula III described herein, it is understood (unless indicated otherwise) that a compound of Formula I includes all sub-embodiments thereof, a compound of Formula II includes all sub-embodiments thereof, and a compound of Formula III includes all sub-embodiments thereof.

In one aspect, methods are provided for treating a protein kinase mediated disease or condition in an animal subject, wherein the method involves administering to the subject an effective amount of one or more compounds of Formula I, Formula II, or Formula III. The terms "treat," "therapy," and like terms refer to the administration of material, e.g., one or more compound of Formula I, Formula II, or Formula III, in an amount effective to prevent, alleviate, or ameliorate one or more symptoms of a disease or condition, i.e., indication, and/or to prolong the survival of the subject being treated. The term "protein kinase mediated disease or condition" refers to a disease or condition in which the biological function of a protein kinase affects the development, course, and/or symptoms of the disease or condition, and/or in which modulation of the protein kinase alters the development, course, and or symptoms of the disease or condition. A protein kinase mediated disease or condition includes a disease or condition for which modulation provides a therapeutic benefit, e.g. wherein treatment with protein kinase inhibitors, including compounds described herein, provides a therapeutic benefit to the subject suffering from or at risk of the disease or condition. In one aspect, the method involves administering to the subject an effective amount of a compound of Formula I, Formula II, or Formula III in combination with one or more other therapies for the disease or condition.

In one aspect, methods are provided for treating a protein kinase mediated disease or condition in an animal subject, wherein the method involves administering to the subject an effective amount of any one or more compound of Formula I, Formula II, or Formula III.

In one aspect, the invention provides methods for treating a Raf protein kinase mediated disease or condition in an animal subject, wherein the method involves administering to the subject an effective amount of one or more compound of Formula I, Formula II, or Formula III. The terms "Raf protein kinase mediated disease or condition," "Raf mediated disease or condition," and the like refer to a disease or condition in which the biological function of a Raf kinase, including any mutations thereof, affects the development, course, and or symptoms of the disease or condition, and/or in which modulation of the Raf protein kinase alters the development, course, and/or symptoms of the disease or condition. The Raf protein kinase includes, but is not limited to, A-Raf, A-Raf mutations, B-Raf, mutations of B-Raf, c-Raf-1 and mutations of c-Raf-1. In some embodiments, the Raf protein kinase is B-Raf mutation V600E. In some embodiments, the Raf protein kinase is B-Raf mutation V600E/T529I. In some embodiments, the disease or condition is a cancer that is amenable to treatment by an inhibitor of the V600E mutant B-Raf. In some embodiments, the disease or condition is a cancer that is amenable to treatment by an inhibitor of the V600E/T5291 mutant B-Raf. The Raf protein kinase mediated disease or condition includes a disease or condition for which Raf inhibition provides a therapeutic benefit, e.g. wherein treatment with Raf inhibitors, including compounds described herein, provides a therapeutic benefit to the subject suffering from or at risk of the disease or condition. In one aspect, the method involves administering to the subject an effective amount of a compound of Formula I, Formula II, or Formula III in combination with one or more other therapies for the disease or condition. Similarly, the terms "A-Raf, B-Raf or c-Raf-1 protein kinase mediated disease or condition," "A-Raf, B-Raf or c-Raf-1 mediated disease or condition," and the like refer to a disease or condition in which the biological function of an A-Raf, B-Raf or c-Raf-1 kinase, respectively, including any mutations thereof, affects the development, course and/or symptoms of the disease or condition, and/or in which modulation of the A-Raf, B-Raf or c-Raf-1 protein kinase, respectively, alters the development, course, and/or symptoms of the disease or condition.

In some embodiments, a compound of Formula I, Formula II, or Formula III will have an $IC_{50}$ of less than 500 nm, less than 100 nM, less than 50 nM, less than 20 nM, less than 10 nM, less than 5 nM, or less than 1 in M as determined in a generally accepted kinase activity assay. In some embodiments, a compound of any of Formula I, Formula II, or Formula III will have an $IC_{50}$ of less than 500 nm, less than 100 nM, less than 50 nM, less than 20 mM, less than 10 nM, less than 5 n1M, or less than 1 in with respect to at least one kinase selected from the group consisting of Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4, Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, including any mutations thereof.

In some embodiments, a compound of Formula I, Formula II, or Formula III will have an $IC_{50}$ of less than 500 nm, less than 100 in, less than 50 nM, less than 20 nM, less than 10 nM, less than 5 nM, or less than 1 nM with respect to at least one kinase selected from the group consisting of Ab1, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3α, Gsk3β, HCK, Her2/Erbb2, Her41Erbb4, IGF1R, IKK beta, Irak4, Itk, Jak1, Jak2, Jak3, Jnk1, Jnk2, Jnk3, Kit, Lck, Lyn, MAP2K1, MAP2K2, MAP4K4, MAPKAPK2, Met, Mnk1, MLK1, p38, PDPK1, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70, including any mutations thereof.

In some embodiments, a compound of Formula I, Formula II, or Formula III will have an $IC_{50}$ of less than 500 nm, less than 100 in M, less than 50 nM, less than 20 nM, less than 10 nM, less than 5 nM, or less than 1 nM with respect to at least one kinase selected from the group consisting of Ab1, A-Raf, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, Lck, Lyn, MAP2K1, MAPKAP kinase 2, Met, p38, PDGFRB, Pim1, PKC theta, Pyk2, Ret, Src, Stk6, Yes, and Zap70, including any mutations thereof.

In some embodiments, a compound of Formula I, Formula II, or Formula III will have an $IC_{53}$ of less than 500 ml, less than 100 nM, less than 50 nM, less than 20 nM, less than 10 nM, less than 5 nM, or less than 1 nM with respect to at least one kinase selected from the group consisting of Ab1, A-Raf, B-Raf, Btk, c-Raf-1, EGFR, EphB2, Erk2, Fak, Fms, Irak4, Jnk1, Jnk2, Jnk3, Kit, Lck, Lyn, MAP2K1, MAPKAP kinase 2, Met, p38, Pim1, PKC theta, Pyk2, Src, Stk6, Yes, and Zap70, including any mutations thereof.

In some embodiments, a compound of Formula I, Formula II, or Formula III will have an $IC_{50}$ of less than 500 nm, less than 100 nM, less than 50 nM, less than 20 nM, less than 10 nM, less than 5 nM, or less than 1 nM with respect to at least one kinase selected from the group consisting of A-Raf, B-Raf, B-Raf V600F mutant, B-Raf V600E/T5291 mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, Kdr, Src and Ret, including any mutations thereof.

In some embodiments, a compound of Formula I, Formula II, or Formula III is an inhibitor of a Raf kinase and has an $IC_{50}$ of less than 500 nm, less than 100 nM, less than 50 nM, less than 203 nM, less than 10 nM, less than 5 nM, or less than 1 nM as determined in a generally accepted Raf kinase activity assay. In some embodiments, a compound of Formula I, Formula II, or Formula III will have an $IC_{50}$ of less than 500 nm, less than 100 nM, less than 50 nM, less than 20 nM, less than 10 nM, less than 5 nM, or less than 1 nM with respect to B-Raf, c-Raf-1, B-Raf V600E mutant, or B-Raf V600E/T5291 mutant. In some embodiments, a compound of Formula I, Formula II, or Formula III will selectively inhibit one Raf kinase relative to one or more other Raf kinases. In some embodiments, the compound of Formula I, Formula II, or Formula III will selectively inhibit a mutation of the Raf kinase relative to the wild type kinase, for example B-Raf V600E mutant relative to wild type B-Raf.

Further to any of the above mentioned embodiments, a compound will also inhibit the effects of a mutation of the kinase, including, but not limited to, a mutation that is related to a disease state, such as a cancer. For example, B-Raf V600E mutant is present in a high percentage of some cancers, such as melanoma, and compounds will inhibit the kinase activity of this mutant.

Further to any of the above embodiments, a compound may selectively inhibit one kinase relative to one or more other kinases, where preferably inhibition is selective with respect to any of the other kinases, whether a kinase discussed herein, or other kinases. In some embodiments, the compound may selectively inhibit the effects of a mutation of the kinase relative to the wild type kinase, for example B-Raf V600E mutant relative to wild type B-Raf. In some embodiments, the compound may selectively inhibit Fms relative to Kit. Selective inhibition of one kinase relative to another is such that the $IC_{50}$ for the one kinase may be at least about 2-fold, also 5-fold, also 10-fold, also 20-fold, also 50-fold, or at least about 100-fold less than the $IC_{50}$ for any of the other kinases as determined in a generally accepted kinase activity assay.

In another aspect, compositions are provided that include a therapeutically effective amount of one or more compound of Formula I, Formula II, or Formula III and at least one pharmaceutically acceptable carrier, excipient, and/or diluent, including combinations of any two or more compounds of Formula I, Formula II or Formula III. The composition can further include a plurality of different pharmacologically active compounds, which can include a plurality of compounds of Formula I, Formula II, or Formula III. In another aspect, the composition can include one or more compounds of Formula I, Formula II, or Formula III along with one or more compounds that are therapeutically effective for the same disease indication. In one aspect, the composition includes one or more compounds of Formula I, Formula II, or Formula III along with one or more compounds that are therapeutically effective for the same disease indication, wherein the compounds have a synergistic effect on the disease indication. In one aspect, the composition includes one or more compounds of Formula I, Formula II, or Formula III effective in treating a cancer and one or more other compounds that are effective in treating the cancer, further wherein the compounds are synergistically effective in treating the cancer.

In another aspect, methods are provided for modulating the activity of a protein kinase selected from the group consisting of Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3a, Gsk3p, HCK, Her2/Erbb2, Her4/Erbb4, IGF1R, IKK beta, Irak4, Itk, Jak1, Jak1, Jak3, Jnk1, Jnk2, Jnk3, Kdr, Kit, Lck, Lyn, MAP2K1, MAP2K2, MAP4K4, MAPKAPK2, Met, Mnk1, MLK1, p3S, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70 by contacting the protein kinase with an effective amount of one or more compound of Formula I, Formula II, or Formula III.

In another aspect, methods are provided for treating a protein kinase mediated disease or condition in an animal subject, wherein the method involves administering to the subject an effective amount of a composition including one or more compound of Formula I, Formula II, or Formula III.

In one aspect, methods are provided for treating a disease or condition mediated by a protein kinase selected from the group consisting of Ab1, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2 Ron, Src, Stk6, Syk, TEC, Tie2, TrkA, TrkB, Yes, and Zap70 by administering to the subject an effective amount of a composition including one or more compound of Formula I, Formula II, or Formula III.

In one aspect, the invention provides methods for treating a disease or condition mediated by a protein kinase selected from the group consisting of Ab1, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3α, Gsk3β, HCK, Her2/Erbb2, Her4/Erbb4, IGF1R, IKK beta, Irak4, Itk, Jak1, Jak1, Jak3, Jnk1, Jnk2, Jnk3, Kit, Lck, Lyn, MAP2K1, MAP2K2, MAP4K4, MAPKAPK2, Met, Mnk1, MLK1, p38, PDPK1, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70 by administering to the subject an effective amount of a composition including one or more compound of Formula I, Formula II, or Formula III.

In one aspect, the invention provides methods for treating a disease or condition mediated by a protein kinase selected from the group consisting of Ab1, A-Raf, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, Lck, Lyn, MAP2K1, MAPKAPK2, Met, p38, PDGFRB, Pim1, PKC theta, Pyk2, Ret, Src, Stk6, Yes, and Zap70 by administering to the subject an effective amount of a composition including one or more compound of Formula I, Formula II, or Formula III.

In one aspect, the invention provides methods for treating a disease or condition mediated by a protein kinase selected from the group consisting of Ab1, A-Raf, B-Raf, Btk, c-Raf-1, EGFR, EphB2, Erk2, Fak, Fms, Irak4, Jnk1, Jnk2, Jnk3, Kit, Lck, Lyn, MAP2K1, MAPKAPK2, Met, p38, Pim1, PKC theta, Pyk2, Src, Stk6, Yes, and Zap70 by administering to the subject an effective amount of a composition including one or more compound of Formula I, Formula II, or Formula III.

In one aspect, the invention provides methods for treating a disease or condition mediated by a protein kinase selected from the group consisting of A-Raf, B-Raf, B-Raf V600E mutant, B-Raf V600E/T529I mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, Kdr, Src and Ret by administering to the subject an effective amount of a composition including one or more compound of Formula I, Formula II, or Formula III.

In one aspect, the invention provides methods for treating a disease or condition mediated by A-Raf, B-Raf, c-Raf-1, B-Raf V600E mutant, or B-Raf V600E/T529I mutant by administering to the subject an effective amount of a composition including one or more compound of Formula I, Formula II or Formula III. In one aspect, the invention provides methods for treating a disease or condition mediated by A-Raf, B-Raf c-Raf-1, B-Raf V600E mutant, or B-Raf V600E/T5291 mutant by administering to the subject an effective amount of a composition including one or more compound of Formula I, Formula II, or Formula III in combination with one or more other suitable therapies for treating the disease. In one aspect, the invention provides methods for treating a cancer mediated by B-Raf V600E mutant or B-Raf V600E/T529I mutant by administering to the subject an effective amount of a composition including one or more compound of Formula I, Formula II, or Formula III in combination with one or more suitable anticancer therapies, such as one or more chemotherapeutic drugs.

In one aspect, the invention provides a method of treating a cancer by administering to the subject an effective amount of a composition including one or more compound of Formula I, Formula II, or Formula III, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one aspect, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or at particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

In a preferred embodiment, the invention provides a method of treating a cancer by administering to the subject an effective amount of a composition including one or more compound of Formula I, Formula II, or Formula III, in combination with one or more suitable chemotherapeutic agents. In one aspect, the one or more suitable chemotherapeutic agents is selected from an alkylating agent, including, but not limited to, adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; an antibiotic, including, but not limited to, bleomycin, dactinomycin, daunorubicin, doxorubicin, epirubicin, idarubicin, menogaril, mitomycin, mitoxantrone, neocarzinostatin, pentostatin, and plicamycin; an antimetabolite, including, but not limited to, azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; an immunotherapy, including, but not limited to, alemtuzumab, bevacizumab, cetuximab, galiximab, gemtuzumab, panitumumab, penuzumab, rituximab, tositumomab, trastuzumab, and 90 Y ibritumomab tiuxetan; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, paclitaxel and DHA-paclitaxel; a retinoid, including, but not limited to, alitretinoin, bexarotene, fenretinide, isotretinoin, and tretinoin; an alkaloid, including, but not limited to, etoposide, homoharringtonine, teniposide, vinblastine, vincristine, vindesine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, edotecarin, exatecan, irinotecan (also active metabolite SN-38 (7-ethyl-10-hydroxy-camptothecin)), rubitecan, topotecan, and 9-aminocamptothecin; a kinase inhibitor, including, but not limited to, erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), aminoglutethimide, asparaginase, bryostatin-1, cilengitide, E7389, ixabepilone, procarbazine, sulindac, temsirolimus, tipifarnib. Preferably, the method of treating a cancer involves administering to the subject an effective amount of a composition including one or more compound of Formula I, Formula II, or Formula III in combination with a chemotherapeutic agent selected from 5-fluorouracil, carboplatin, dacarbazine, gefitinib, oxaliplatin, paclitaxel, SN-38, temozolomide, vinblastine, bevacizumab, cetuximab, or erlotinib.

In another aspect, the invention provides a method of treating or prophylaxis of a disease or condition in a mammal, by administering to the mammal a therapeutically effective amount of one or more compound of Formula I, Formula II, or Formula III, a prodrug of such compound, or a pharmaceutically acceptable salt of such compound or prodrug. The compound can be alone or can be par of a composition. In another aspect, the invention provides a method of treating or prophylaxis of a disease or condition in a mammal, by administering to the mammal a therapeutically effective amount of one or more compound of Formula I, Formula II, or Formula III, a prodrug of such compound, or a pharmaceutically acceptable salt of such compound or prodrug in combination with one or more other suitable therapies for the disease or condition.

In a related aspect, the invention provides kits that include a composition as described herein. In some embodiments, the composition is packaged, e.g., in a vial, bottle, flask, which may be further packaged, e.g., within a box, envelope, or bag; the composition is approved by the U.S. Food and Drug Administration or similar regulatory agency for administration to a mammal, e.g., a human, the composition is approved for administration to a mammal, e.g., a human, for a protein kinase mediated disease or condition; the invention kit includes written instructions for use and/or other indication that the composition is suitable or approved for administration to a mammal, e.g., a human, for a protein kinase-mediated disease or condition, and the composition is packaged in unit dose or single dose form, e.g., single dose pills, capsules, or the like.

In aspects involving treatment or prophylaxis of a disease or condition with the compounds of Formula I, Formula II, or Formula III, the disease or condition is, for example without limitation neurologic diseases, including, but not limited to, cerebrovascular ischemia, multi-infarct dementia, head injury, spinal cord injury, Alzheimer's disease (AD), Parkinson's disease, amyotrophic lateral sclerosis, dementia, senile chorea, and Huntington's disease; neoplastic diseases and associated complications, including, but not limited to, chemotherapy-induced hypoxia, gastrointestinal stromal tumors (GISTs), prostate tumors, mast cell tumors (including canine mast cell tumors), acute myeloid myelofibrosis, leukemia, acute lymphocytic leukemia, chronic myeloid leukemia, chronic lymphocytic leukemia, multiple myeloma, melanoma, mastocytosis, gliomas, glioblastoma, astrocytoma, neuroblastoma, sarcomas (e.g. sarcomas of neuroectodermal origin, leiomyosarcoma), carcinomas (e.g. lung, breast, pancreatic, colon, hepatocellular, renal, female genital tract, squamous cell, carcinoma in situ), lymphoma (e.g. histiocytic lymphoma, non-Hodgkin's lymphoma), MEN2 syndromes, neurofibromatosis (including Schwann cell neoplasia), myelodysplastic syndrome, leukemia, tumor angiogenesis, cancers of the thyroid, liver, bone, skin, brain, central nervous system, pancreas, lung (e.g. small cell lung cancer, non small cell lung cancer), breast, colon, bladder, prostate, gastrointestinal tract, endometrium, fallopian tube, testes and ovary, and metastasis of tumors to other tissues; pain of neuropathic or inflammatory origin, including, but not limited to, acute pain, chronic pain, bone pain, cancer-related pain and migraine; cardiovascular diseases, including, but not limited to, heart failure, ischemic stroke, cardiac hypertrophy, thrombosis (e.g. thrombotic microangiopathy syndromes), atherosclerosis, reperfusion injury and ischemia (e.g. cerebrovascular ischemia, liver ischemia); inflammation including, but not limited to, age-related macular degeneration, rheumatoid arthritis, allergic rhinitis, inflammatory bowel disease (IBD), ulcerative colitis, Crohn's disease, systemic lupus erythematosis, Sjogren's Syndrome, Wegener's granulomatosis, Kawasaki's Disease, hemophagocytic syndrome (macrophage activation syndrome), multicentric reticulohistiocytosis, psoriasis, scleroderma, chronic thyroiditis, Grave's disease, myasthenia gravis, multiple sclerosis, osteoarthritis, endometriosis, scarring (e.g. dermal, tissue), vascular restenosis, fibrotic disorders, hypereosinophilia, CNS inflammation, pancreatitis, nephritis, atopic dermatitis, and hepatitis; immunodeficiency diseases, including, but not limited to, severe combined immunodeficiency (SCID), organ transplant rejection, and graft versus host disease; renal or prostatic diseases, including, but not limited to, diabetic nephropathy, polycystic kidney disease, nephrosclerosis, glomerulonephritis, interstitial nephritis, Lupus nephritis, prostate hyperplasia, chronic renal failure, tubular necrosis, diabetes-associated renal complications, and renal hypertrophy; metabolic diseases, including, but not limited to, type 1 diabetes, type 2 diabetes, metabolic syndrome, obesity, hepatic steatosis, insulin resistance, hyperglycemia, lipolysis and obesity, infection, including, but not limited to, *Helicobacter pylori*, Hepatitis and Influenza viruses, fever, and sepsis; pulmonary diseases, including, but not limited to, chronic obstructive pulmonary disease (COPD), acute respiratory distress syndrome (ARDS), asthma, allergy, bronchitis, emphysema, and pulmonary fibrosis; genetic developmental diseases, including, but not limited to, Noonan's syndrome, Crouzon syndrome, acrocephalo-syndactyly type I, Pfeiffer's syndrome, Jackson-Weiss syndrome, Costello syndrome, (faciocutaneoskeletal syndrome), LEOPARD syndrome, cardio-faciocutaneous syndrome (CFC) and neural crest syndrome abnormalities causing cardiovascular, skeletal, intestinal, skin, hair and endocrine diseases; disorders of bone structure, mineralization and bone reformation and resorption, including, but not limited to, osteoporosis, increased risk of fracture, Paget's disease, hypercalcemia, osteomyelitis, peri-prosthetic or wear-debris-mediated osteolysis, and metastatis of cancer to bone; Grave's disease; Hirschsprung's disease; lymphoedema; selective T-cell defect (STD); X-linked agammaglobulinemia; diabetic retinopathy; alopecia; erectile dysfunction; tuberous sclerosis, and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, camitine deficiency, carnitine palmatyl transferase deficiency, phosphoglycerate kinase deficiency, phosphoglycerate mutase deficiency, lactate dehydrogenase deficiency, and myoadenylate deaminase deficiency).

In aspects involving treatment or prophylaxis of a disease or condition with the compounds of Formula I, Formula II, or Formula III, the invention provides methods for treating an A-Raf-mediated, 13-Raf-mediated and/or c-Raf-1-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal A-Raf, B-Raf, and/or c-Raf-1 activity (e.g. kinase activity). Invention methods involve administering to the subject suffering from or at risk of an A-Raf-mediated, B-Raf-mediated and/or c-Raf-1-mediated disease or condition an effective amount of compound of Formula I, Formula II or Formula III. In one embodiment, the A-Raf-mediated, B-Raf-mediated, and or c-Raf-1-mediated disease is selected from the group consisting of neurologic diseases, including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute mycloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to *Helicobacter pylori*, Hepatitis and Influenza viruses, fever, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardiofaciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Maric-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

In a related aspect, compounds of Formula I, Formula II, or Formula III, can be used in the preparation of a medicament for the treatment of an A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute myeloid leukemia, myclodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases, including, but not limited to, heart failure, ischemic stroke, cardiac hypertrophy, thrombosis (e.g. thrombotic microangiopathy syndromes), atherosclerosis, and reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to, *Helicobacter pylori*, Hepatitis and Influenza viruses, fever, and sepsis; pulmonary diseases, including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardiofaciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic. Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenital paramyotonia congenital central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

The compounds of Formula I, Formula II, or Formula III with kinase activity $IC_{50}$ less than 10 μM as determined in a standard assay described herein can be used to treat protein kinase mediated diseases and conditions related to the following protein kinases, including any mutations thereof, for example without limitation:

Ab1, related to chronic myeloid leukemia (CML), acute lymphoblastic leukemia (ALL) and acute myelogenous leukemia (AML);

Akt1, related to gastric, prostate, colorectal, ovarian, pancreatic and breast cancer, glioblastoma and leukemia, as well as schizophrenia and bipolar disorders, and also use in combination with other chemotherapeutic drugs;

Akt2, related to hyperglycemia due to peripheral insulin resistance and nonsuppressible hepatic glucose production accompanied by inadequate compensatory hyperinsulinemia, also related to pancreatic, ovarian and breast cancer;

Akt3, related to melanoma, prostate and breast cancer;

ALK, related to non-Hodgkin lymphomas such as diffuse large B-cell lymphoma and anaplastic large cell lymphoma;

Alk5, related to pancreatic and biliary cancers, and cutaneous T-cell lymphoma;

A-Raf, related to neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myclodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf or c-Raf-1, related to neurologic diseases, including, but not limited to, as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to, *Helicobacter pylori*, Hepatitis and Influenza viruses, fever, and sepsis: pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases;

Brk, related to breast and colon cancer, and head and neck squamous cell carcinoma;

Btk, related to X-linked agammaglobulinemia, acute lymphocytic leukemia, autoimmune diseases such as multiple sclerosis, systemic lupus erythematosis, rheumatoid arthritis, and Graves' disease, immune suppression in organ transplant, and drug sensitivity of B-lineage cells;

Cdk2, related to prostate, breast, colorectal and ovarian cancer;

Cdk4, related to glioblastoma (e.g. glioblastoma multiforme), anaplastic astrocytoma, and breast cancer;

Cdk5, related to Alzheimer's disease, amyotrophic lateral sclerosis and Lewy body disease;

Cdk6, related to glioblastoma multiforme, non-Hodgkin's lymphoma, splenic marginal zone lymphoma, T-cell lymphoblastic lymphoma (T-LBL) and T-cell acute lymphoblastic leukemia (T-ALL);

CHK1, related to DNA damage repair, sensitizes cells to chemotherapeutic agents;

Csk, related to colon and pancreatic carcinomas and autoimmune pathology such as type I diabetes, rheumatoid arthritis and systemic lupus erythematosus;

EGFR, related to breast, colorectal, bladder, prostate and non small cell lung cancer, squamous cell carcinomas of the head and neck cancer, oral cavity, and esophagus, and glioblastoma multi forme;

EphA1, related to head and neck squamous cell carcinoma, hepatoma and lung cancer;

EphA2, related to aberrant short-range contact-mediated axonal guidance, bladder, breast, prostate, colon, skin, cervical, ovarian, pancreatic and lung cancers, and metastatic melanoma;

EphB2, related to angiogenesis disorder (e.g. ocular angiogenesis disease such as retinopathy), and cancer (e.g. glioblastoma, breast and liver cancer);

EphB4, related to colorectal cancer (CRC), head and neck squamous cell carcinoma, and tumours of the prostate, breast, endometrium, and bladder;

Erk2, related to aberrant proliferation, differentiation, transcription regulation and development, and may be useful in treating inflammation, for example inflammation associated with Lyme neuroborreliosis, and in treating cancers, such as gastric cancer;

Fak, related to colon and breast tumors, and is also related to esophageal squamous cell carcinoma, melanoma, anaplastic astrocytoma, glioblastoma, ductal carcinoma in situ, prostate and hepatocellular carcinoma, and tumor metastases, and may also provide synergistic effects when used with other chemotherapeutic drugs;

FGFR1, related to 8p11 myeloproliferative syndrome;

FGFR2, related to Crouzon Syndrome, Jackson-Weiss Syndrome, Apert Syndrome, craniosynostosis, Pfeiffer Syndrome, acrocephalo syndactyly type V, and Beare-Stevenson Cutis Gyrata Syndrome;

FGFR3, related to angiogenesis, wound healing, achondroplasia, Muenke craniosynostosis, Crouzon syndrome, acanthosis nigricans, thanatophoric dysplasia, bladder carcinomas, and multiple myeloma;

FGFR4, related to cancer of the breast, lung, colon, medullary thyroid, pancreas, ovary, prostate, endometrium, and fallopian tube, head and neck squamous cell carcinomas and leiomyosarcoma;

Flt1, related to non-small cell lung carcinoma, prostate carcinoma, and colorectal cancer;

Flt3, related to acute myeloid leukemia, myelodysplastic syndrome, acute lymphoblastic leukemia;

Flt4, related to primary lymphoedema;

Fms, related to immune disorders, including, but not limited to, rheumatoid arthritis, systemic lupus erythematosis (SLE), and transplant rejection; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type IT diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), prostate cancer, breast cancer, ovarian cancer, melanoma, glioblastoma multiforme, metastasis of tumors to other tissues, and other chronic myeloproliferative diseases such as myelofibrosis;

Frk, related to acute myeloid leukemia and type 1 diabetes;

Fyn, related to Alzheimer's disease, schizophrenia and prevention of metastases, e.g. in melanoma and squamous cell carcinoma;

GSK3 (Gsk3α and/or Gsk3β), related to CNS disorders such as Alzheimer's disease, Parkinson's disease, amyotrophic lateral sclerosis, diabetes type II, bipolar disorders, stroke, cancer, chronic inflammatory disease, leucopenia, schizophrenia, chronic pain, neuropathic pain, and traumatic head injury;

HCK, related to chronic myelogenous leukemia and acute lymphocytic leukemia;

Her2/Erbb2, related to prostate and breast cancer;

Her4/Erbb4, related to childhood medulloblastoma;

IGF1R, related to prostate cancer, hepatocellular carcinoma;

IKK beta, related to leukemia of T-cells, necrosis, insulin resistance, and malignant neoplasms;

Irak4, related to bacterial infections, immunodeficiency syndrome, Crohn's disease, ulcerative colitis, asthma, chronic bronchitis, cardio hypertrophy, and kidney hypertension;

Itk, related to allergic asthma;

Jak1, related to Hepatitis C virus infection;

Jak2, related to myeloproliferative disorders such as polyythaemia vera, myelofibrosis, essential thrombocythemia, myeloid metaplasia and leukemias, including acute lymphoblastic leukemia, chronic neutrophilic leukemia, juvenile myelomonocytic leukemia, CMML, Philadelphia chromosome-negative CML, megakaryocytic leukemia, and acute erythroid leukemia;

Jak3, related to X-linked severe combined immunodeficiency, myeloproliferative disorders, transplant rejection and autoimmune diseases such as rheumatoid arthritis, inflammatory bowel syndrome, Crohn's disease, systemic lupus erythematosis, ulcerative colitis, psoriasis and multiple sclerosis;

Jnk (Jnk1, Jnk2, Jnk3), related to metabolic diseases including type 1 diabetes, type 2 diabetes, metabolic syndrome, obesity, and hepatic steatosis; cardiovascular diseases such as atherosclerosis, ischemia (e.g. cerebrovascular ischemia, liver ischemia), reperfusion injury, cardiac hypertrophy; renal diseases such as chronic renal failure; neoplastic diseases and associated complications, including chemotherapy-induced hypoxia, prostate tumors, myeloid leukemia and cancers of the liver, bone, skin, brain, pancreas, lung breast, colon, prostate and ovary; transplant rejection; pain of neuropathic or inflammatory origin including acute and chronic pain; inflammatory and autoimmune diseases including age-related macular degeneration, rheumatoid arthritis, inflammatory bowel disease, ulcerative colitis, Crohn's disease, systemic lupus erythematosis, Sjogren's Syndrome, psoriasis, scleroderma, chronic thyroiditis, Grave's disease, myasthenia gravis, and multiple sclerosis, and inflammation in other organs including CNS inflammation, pancreatitis, nephritis, atopic dermatitis, and hepatitis; airway inflammatory diseases such as asthma, allergy, bronchitis, pulmonary fibrosis, chronic obstructive pulmonary disease; neurologic diseases such as stroke, cerebrovascular ischemia, neurodegenerative diseases such as Parkinson's disease, Alzheimer's disease, amyotrophic lateral sclerosis, dementia, senile chorea, head and spinal cord trauma, and Huntington's disease. More particularly, Jak1 is related to type I diabetes, type 2 diabetes, metabolic syndrome, obesity and hepatic steatosis, Jnk2 is related to atherosclerosis, and Jnk3 is related to inflammatory diseases including autoimmune diseases such as rheumatoid arthritis, inflammatory bowel syndrome, Crohn's disease, systemic lupus erythematosis, Sjogren's Syndrome, psoriasis and multiple sclerosis, airway inflammatory diseases such as asthma, allergy, pulmonary fibrosis, and chronic obstructive pulmonary disease, and inflammation in other organs, such as CNS inflammation, pancreatitis, nephritis, and hepatitis; neurologic diseases such as stroke, cerebrovascular ischemia, and neurodegenerative diseases such as Parkinson's disease, Alzheimer's disease, and Huntington's disease; and neoplastic diseases such as prostate tumors and myeloid leukemia;

Kdr, related to anti-angiogenesis for treating solid tumor growth (e.g. ovarian, lung, breast, pancreatic, prostate, colon, gastrointestinal stromal tumor, non small cell lung cancer, and epidermoid cancer), metastasis, psoriasis, rheumatoid arthritis, diabetic retinopathy and age related macular degeneration;

Kit, related to malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myclogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, and hypereosinophilia;

Lck, related to acute lymphoblastic leukemia, T-cell lymphoma, lymphopenia, renal carcinoma, colon carcinoma, severe combined immunodeficiency, multiple sclerosis, inflammatory bowel and type I diabetes;

Lyn, related to

MAP2K1, related to acute mycloid leukemia, breast, ovarian and liver cancer;

MAP2K2, related to cancer and inflammation;

MAP4K4, related to metabolic indications, including re-sensitizing fat and muscle cells to insulin, ameliorating the pathology in adipocytes, ameliorating the pathology in muscle cells, metabolic syndrome, and type II diabetes; a broad range of oncology indications, including blocking the migration, invasion and metastasis in many different tumor types; and T-cell mediated autoimmune diseases;

MAPKAPK2, cancer (e.g. prostate, breast), stroke, meningitis, and inflammatory disorders;

Met, related to kidney, breast, bladder, non-small-cell lung, colorectal, and bladder cancers, and hepatocellular carcinoma;

Mnk1, related to conditions associated with heat shock, nutrient deprivation, oxidative or osmotic stress, and infection of mammalian cells (e.g. with viruses such as adenovirus (Ad) or influenza virus), and autoimmune diseases;

MLK1, related to neurodegenerative diseases such as Alzheimer's disease and Parkinson's disease, and inflammatory disorders;

p38, related to acute coronary syndrome, stroke, atherosclerosis, and inflammatory autoimmune diseases such as rheumatoid arthritis, inflammatory bowel disease, and Crohn's disease;

PDGFR (PDGFRA, PDGFRB), related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis. More particularly, PDGFRA related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis, and PDGFRB related to idiopathic hypercosinophilic syndrome, chronic eosinophilic leukemia, juvenile myelomonocytic leukemia, and metastatic medulloblastoma;

PDPK1, related to cancer and diabetes;

Pim1, related to cancers such as hematopoietic (e.g. acute myeloid and acute lymphoid leukemias) and prostate cancers, and non-Hodgkin's lymphomas;

Pim2, related to lymphomas;

Pim3, related to hepatocellular carcinoma;

PKC alpha, related to pituitary tumors and prefrontal cortical dysfunction such as distractibility, impaired judgment, impulsivity, and thought disorder, also may be used to sensitize chemotherapy in breast, colon, and non small cell lung cancers;

PKC beta, related to diabetic retinopathy;

PKC-theta, related to insulin resistance, T-cell lymphoma;

Plk1, related to cancers (e.g. lymphoma of the thyroid, non-Hodgkin's lymphomas, colorectal cancers, leukemias and melanoma), also useful as sensitizer in chemotherapy;

Pyk2, related to inflammation (e.g. osteoporosis, polycystic kidney disease, rheumatoid arthritis and inflammatory bowel disease), CNS disease (e.g. Parkinson's disease and Alzheimer's disease), stroke and cancers (e.g. gliomas, breast cancer, and pancreatic cancer);

Ret, related to cancer of the thyroid, neuroblastoma, familial medullary thyroid carcinoma (FMTC), multiple endocrine neoplasia type IIA and IIB (MEN2A, MEN2B), and neurodegenerative disorders (e.g. Hirschsprung's disease, Parkinson's disease, Alzheimer's disease, and amyotrophic lateral sclerosis);

ROCK (ROCK-1, ROCK-2), related to cancers (e.g. ovarian cancer, hepatocellular carcinoma, pancreatic cancer), ocular disease (e.g. glaucoma), cardiac hypertrophy, improved renal perfusion, transplant rejection, and acute respiratory distress syndrome;

Ron, related to cancer and inflammation;

Src, related to cancer and osteoporosis;

Stk6, related to gastric, bladder, breast, lung, CNS, ovarian, kidney, colon, prostate, pancreas, and cervical cancers, melanoma, leukemia, and neuroblastoma;

Syk, related to lymphomas (e.g. mantle cell lymphoma);

TEC, related to sepsis, septic shock, inflammation, rheumatoid arthritis, Crohn's disease, irritable bowel disease (IBD), and ulcerative colitis;

Tie2 (TEK), related to cancer, arthritis (e.g. rheumatoid arthritis), and atherosclerosis;

TrkA, related to pain (e.g. chronic pain, neuropathic pain), cancer (e.g. prostate cancer, lung cancer, pancreatic cancer), allergic disorders (e.g. asthma), arthritis, diabetic retinopathy, macular degeneration and psoriasis;

TrkB, related to obesity, hyperphagia, developmental delays, cancer (e.g. prostate cancer, lung cancer, Wilms tumors, neuroblastoma, pancreatic cancer), various neuropathies (e.g. stroke, multiple sclerosis, transverse myelitis, and encephalitis), and diabetes.

Yes, related to various cancers including esophageal squamous cell carcinoma; and Zap70, related to AIDS, systemic lupus erythematosus, myasthenia gravis, atherosclerosis, rejection of transplanted organs or tissues, allograft rejection including acute and chronic allograft rejection, graft versus host disease, rheumatoid arthritis, psoriasis, systemic sclerosis, atopic dermatitis, eczematous dermatitis, alopecia, and inflammation of the nasal mucus membrane, including all forms of rhinitis.

Additional aspects and embodiments will be apparent from the following Detailed Description and from the claims.

DETAILED DESCRIPTION OF THE PREFERRED EMBODIMENTS

As used herein the following definitions apply unless clearly indicated otherwise:

"Halogen" refer to all halogens, that is, chloro (Cl), fluoro (F), bromo (Br), or iodo (I).

"Hydroxyl" or "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched alkyl group is attached at any available point to produce a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. A "substituted lower alkyl" denotes lower alkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^e$, —R$^f$, and —R$^g$. Furthermore, possible substitutions include subsets of these substitutions, such as are indicated herein, for example, in the description of compounds of Formula I, Formula II, or Formula III, attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety. "C$_{2-6}$ alkyl" denotes lower alkyl containing 2-6 carbon atoms. A "substituted C$_{2-6}$ alkyl" denotes optionally substituted lower alkyl containing 2-6 carbon atoms. A "substituted methyl" denotes methyl that is independently substituted, unless indicated otherwise, with 1, 2, or 3 substituents, wherein the substituents are selected as per optionally substituted lower alkyl.

"C$_{1-3}$ alkylene" refers to a divalent alkane-derived radical containing 1-3 carbon atoms, straight chain or branched, from which two hydrogen atoms are taken from the same carbon atom or from different carbon atoms. C$_{1-3}$ alkylene includes methylene —CH$_2$—, ethylene —CH$_2$CH$_2$—, propylene —CH$_2$CH—CH$_2$—, and isopropylene —CH(CH$_3$)CH$_2$— or —CH$_2$CH(CH$_3$)—. C$_{1-3}$ alkylene substituted with one or more substituents indicates C$_{1-3}$ alkylene that is independently substituted, with one or more, preferably 1, 2, 3, 4 or 5, also 1, 2, or 3 substituents as indicated, attached at any available atom to produce a stable compound.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. Examples of lower alkenyl groups include ethenyl, propenyl, isopropenyl, butenyl, and the like. A "substituted lower alkenyl" denotes lower alkenyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$OR$^o$, —OR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^d$, —R$^f$, and —R$^g$. Further, possible substitutions include subsets of these substitutions, such as are indicated herein, for example, in the description of compounds of Formula I, Formula II, or Formula III, attached at any available atom to produce a stable compound. For example "fluoro substituted lower alkenyl" denotes a lower alkenyl group substituted with one or more fluoro atoms, where preferably the lower alkenyl is substituted with 1, 2, 3, 4 or 5 fluoro atom s, also 1, 2, or 3 fluoro atoms. While it is understood that substitutions are attached at any available atom to produce a stable compound, substitution of alkenyl groups are such that —F, —C(O)—, —C(S)—, —C(NH)—, —S(O)—, —S(O)$_2$—, —O—, —S—, or N (except where N is a heteroaryl ring atom), are not bound to an alkene carbon thereof. Further, where alkenyl is a substituent of another moiety or an R group of a moiety such as —OR, —NHR, —C(O)R, and the like, substitution of the moiety is such that any —C(O)—, —C(S)—, —S(O)—, —S(O)$_2$—, —O—, —S—, or N thereof (except where N is a heteroaryl ring atom) are not bound to an alkene carbon of the alkenyl substituent or R group. Further, where alkenyl is a substituent of another moiety or an R group of a moiety such as —OR, —NHR, —C(O)NHR, and the like, substitution of the alkenyl R group is such that substitution of the alkenyl carbon bound to any O, S, or N of the moiety (except where N is a heteroaryl ring atom) excludes substituents that would result in any O, S, or N of the substituent (except where N is a heteroaryl ring atom) being bound to the alkenyl carbon bound to any 0, A, or N of the moiety. An "alkenyl carbon" refers to any carbon within an alkenyl group, whether saturated or part of the carbon to carbon double bond. An "alkene carbon" refers to a carbon within an alkenyl group that is part of a carbon to carbon double bond.

"Lower alkynyl" alone or in combination means a straight or branched hydrocarbon containing 2-6 carbon atoms (unless specifically defined) containing at least one, preferably one, carbon to carbon triple bond. Examples of alkynyl groups include ethynyl, propynyl, butynyl, and the like. A "substituted lower alkynyl" denotes lower alkynyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)

NHR°, —C(S)NHR°, —C(O)NR°R°, —C(S)NR°R°, —S(O)₂NHR°, —S(O)₂NR°R°, —C(NH)NHR°, —C(NH)NR^p R^c, —NHC(O)R°, —NHC(S)R°, —NR°C(O)R°, —NR°C(S)R°, —NR°S(O)₂R°, —NR°S(O)₂R°, —NHC(O)NHR°, —NHC(S)NHR°, —NR°C(O)NH₂, —NR°C(S)NH₂, —NR°C(O)NHR°, —NR°C(S)NHR°, —NHC(O)NR°R°, —NHC(S)NR°R°, —NR°C(O)NR°R°, —NR°C(S)NR°R°, —NHS(O)₂NHR°, —NR°S(O)₂NH₂, —NR°S(O)₂NHR°, —NHS(O)₂NR°R°, —NR°S(O)₂NR°R°, —NR°R°, —NR°R°, —R^d, —R^e, and —R^g. Further, possible substitutions include subsets of these substitutions, such as are indicated herein, for example, in the description of compounds of Formula I, Formula II, or Formula III, attached at any available atom to produce a stable compound. For example "fluoro substituted lower alkynyl" denotes a lower alkynyl group substituted with one or more fluoro atoms, where preferably the lower alkynyl is substituted with 1, 2, 3, 4 or 5 fluoro atoms, also 1, 2, or 3 fluoro atoms. While it is understood that substitutions are attached at any available atom to produce a stable compound, substitution of alkynyl groups are such that —F, —C(O)—, —C(S)—, —C(NH)—, —S(O)—, —S(O)₂—, —O—, —S—, or N (except where N is a heteroaryl ring atom) are not bound to an alkyne carbon thereof. Further, where alkynyl is a substituent of another moiety or an R group of a moiety such as —OR, —NHR, —C(O)R, and the like, substitution of the moiety is such that any —C(O)—, —C(S)—, —S(O)—, —S(O)₂—, —O—, —S—, or N thereof (except where N is a heteroaryl ring atom) are not bound to an alkyne carbon of the alkynyl substituent or R group. Further, where alkynyl is a substituent of another moiety or an R group of a moiety such as —OR, —NHR, —C(O)NHR, and the like, substitution of the alkynyl R group is such that substitution of the alkynyl carbon bound to any O, S, or N of the moiety (except where N is a heteroaryl ring atom) excludes substituents that would result in any O, S, or N of the substituent (except where N is a heteroaryl ring atom) being bound to the alkynyl carbon bound to any O, S, or N of the moiety. An "alkynyl carbon" refers to any carbon within an alkynyl group, whether saturated or part of the carbon to carbon triple bond. An "alkyne carbon" refers to a carbon within an alkynyl group that is part of a carbon to carbon triple bond.

"Cycloalkyl" refers to saturated or unsaturated, non-aromatic monocyclic, bicyclic or tricyclic carbon ring systems of 3-1S, also 3-8, more preferably 3-6, ring members per ring, such as cyclopropyl, cyclopentyl, cyclohexyl, adamantyl, and the like. A "substituted cycloalkyl" is a cycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH₂, —NO₂, —CN, —C(O)OH, —C(S)OH, —C(O)NH₂, —C(S)NH₂, —S(O)₂NH₂, —NHC(O)NH₂, —NHC(S)NH₂, —NHS(O)₂NH₂, —C(NH)NH₂, —OR°, —SR°, —OC(O)R°, —OC(S)R°, —C(O)R°, —C(S)R°, —C(O)OR°, —C(S)OR°, —S(O)R°, —S(O)₂R°, —C(O)NHR°, —C(S)NHR°, —C(O)NR°R°, —C(S)NR°R°, —S(O)₂NHR°, —S(O)₂NR°R°, —C(NH)NHR°, —C(NH)NR^p R^c, —NHC(O)R°, —NHC(S)R°, —NR°C(O)R°, —NR°C(S)R°, —NHS(O)₂R°, —NR°S(O)₂R°, —NHC(O)NHR°, —NHC(S)NHR°, —NR°C(O)NH₂, —NR°C(S)NH₂, —NR°C(O)NHR°, —NR°C(S)NHR°, —NHC(O)NR°R°, —NHC(S)NR°R°, —NR°C(O)NR°R°, —NR°C(S)NR°R°, —NHS(O)₂NHR°, —NR°S(O)₂NH₂, —NR°S(O)₂NHR°, —NHS(O)₂NR°R°, —NR°S(O)₂NR°R°, —NHR°, —NR°R°, —R^d, —R^e, —R^f; and —R^g.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. A "substituted heterocycloalkyl" is a heterocycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH₂, —NO₂, —CN, —C(O)OH, —C(S)OH, —C(O)NH₂, —C(S)NH₂, —S(O)₂NH₂, —NHC(O)N₂, —NHC(S)NH₂, —NHS(O)₂NH₂, —C(NH)NH₂, —OR°, —SR°, —OC(S) R°, —OC(S)R°, —C(O)R°, —C(S)R°, —C(O)OR°, —C(S)OR°, —S(O)R°, S(O)₂R°, —C(O)NHR°, —C(S)NHR°, —C(O)NR°R°, —C(S)NR°R°, —S(O)₂NHR°, —S(O)NR°R°, —C(NH)NHR°, —C(NH)NR^p R^c, —NHC(O)R°, —NHC(S)R°, —NR°C(O)R°, —NR°C(S)R°, —NHS(O)₂R°, —NR°S(O)₂R°, —NHC(O)NHR°, —NHC(S)NHR°, —NR°C(O)NH₂, —NR°C(S)NH₂, —NR°C(O)NHR°, —NR°C(S)NHR°, —NHC(O)NR°R°, —NHC(S)NR°R°, —NR°C(O)NR°R°, —NR°C(S)NR°R°, —NHS(O)₂NHR°, —NR°S(O)₂NH₂, —NR°S(O)₂R°, —NHS(O)₇NR°R°, —NR°S(O)₂NR°R°, —NHR°, —NR°R°, —R^d, —R^e, —R^f, and —R^g.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. "Arylene" is a divalent aryl. A "substituted aryl" is an aryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH₂, —NO₂, —CN, —C(O)OH, —C(S)OH, —C(O)N₂, —C(S)NH₂, —S(O)₂NH₂, —NHC(O)NH₂, —NHC(S)NH₂, —NHS(O)₂NH₂, —C(NH)NH₂, —OR°, —SR°, —OC(O)R°, —OC(S) R°, —C(O)R°, —C(S)R°, —C(O)OR°, —C(S)OR°, —S(O) R°, —S(O)₂R°, —C(O)NHR°, —C(S)NHR°, —C(O)NR°R°, —C(S)NR°R°, —S(O)₂NHR°, —S(O)₂NR°R°, —C(NH)NHR°, —C(NH)NR^p R^c, —NHC(O)R°, —NHC(S) R°, —NR°C(O)R°, —NR°C(S)R°, —NHS(O)₂R°, —NR°S (O)₂R°, —NHC(O)NHR°, —NHC(S)NHR°, —NR°C(O) NH₂, —NR°C(S)NH₂, —NR°C(O)NHR°, —NR°C(S)NHR°, —NHC(O)NR°R°, —NHC(S)NR°R°, —NR°C(O)NR°R°, —NR°C(S)NR°R°, —NHS(O)₂NHR°, —NR°S(O)₂NH, —NR°S(O)₂NHR°, —NHS(O)₂NR°R°, —NR°S(O)₂NR°R°, —NHR°, —NR°R°, —R^d, —R^e, —R^f, and —R^g. A "substituted arylene" is a divalent substituted aryl.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Nitrogen containing heteroaryl" refers to heteroaryl wherein any heteroatoms are N. "Heteroarylene" is a divalent heteroaryl. A "substituted heteroaryl" is a heteroaryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^d$, —R$^e$, —R$^f$, and —R$^g$. "Substituted heteroarylene" is a divalent substituted heteroaryl.

The variables R$^o$, R$^p$, R$^c$, R$^d$, R$^e$, R$^f$ and R$^g$ as used in the description of optional substituents for alkyl, alkenyl, alkynyl, cycloalkyl, heterocycloalkyl, aryl and heteroaryl are defined as follows:

each R$^o$, R$^p$, and R$^c$ are independently selected from the group consisting of R$^d$, R$^e$, R$^f$, and R$^g$, or R$^p$ and R$^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, —OR$^u$, —SR$^u$, —NHR$^u$, —NR$^u$R$^u$, —R$^x$, and —R$^y$;

each R$^d$ is independently lower alkyl, wherein lower alkyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$ NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NR$^k$, —NR$^k$C(S)NHR$^k$, —N C(O)NR$^k$R$^k$, —NC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^i$, and —R$^j$;

each R$^e$ is independently lower alkenyl, wherein lower alkenyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$ NH$_2$, —NHC(O)N$_2$, —NHC(S)NH$_2$, —NHS(O)$_2$ NH$_2$, —C(NH)NH$_2$, —OR$^k$, —SR$^k$, —OC(O)R$^k$, —OC(S)R$^k$, —C(O)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, NC(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$N$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, and —R$^j$;

each R$^f$ is independently lower alkynyl, wherein lower alkynyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$ NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, and —R$^j$;

each R$^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$ NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, R$^k$—CH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, NR$^k$C(O)NHR$^k$, NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, —R$^i$, and —R$^j$;

wherein R$^k$, R$^m$, and R$^n$ at each occurrence are independently selected from the group consisting of R$^h$, R$^i$, and R$^j$, or R$^m$ and R$^n$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each R$^h$ is independently lower alkyl optionally substituted with one or more, preferably 1, 2, 3, 4 or 5, also 1, 2, or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —C(NH)NR$^s$R$^t$, —NHC(O)R$^r$, —NHC(S)R$^r$, —NR$^r$C(O)R$^r$, —NR$^r$C(S)R$^r$, —NHS(O)$_2$R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NHR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NHR$^r$, —NH S(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, —NR$^r$R$^r$, —R$^i$, and —R$^j$;

wherein each R$^i$ is independently selected from the group consisting of lower alkenyl and lower alkynyl, wherein lower alkenyl or lower alkynyl are optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)N$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —C(NH)NR$^r$R$^t$, —NHC(O)R$^r$, —NHC(S)R$^r$, —NR$^r$C(O)R$^r$, —NR$^r$C(S)R$^r$, —NHS(O)$_2$R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NHR$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, —NR$^r$R$^r$, and —R$^j$;

wherein each R$^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3 or 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^t$, —S(O)$_2$NHR$^r$, —S(O)$_2$NR$^r$R$^r$, —C(NH)NHR$^r$, —C(NH)NR$^s$R$^t$, —NHC(O)R$^r$, —NHC(S)R$^r$, —NR$^r$C(O)R$^r$, —NR$^r$C(S)R$^r$, —NHS(O)$_2$R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, NR$^r$R$^r$, cycloalkylamino, and —R$^x$;

wherein each R$^r$, R$^s$, and R$^t$ at each occurrence are independently selected from the group consisting of lower alkyl, C$_{3-6}$ alkenyl, C$_{3-6}$ alkynyl, cycloalkyl, heterocycloalkyl, aryl and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the lower alkyl carbon bound to any O, S, or N, of —OR$^r$, —SR$^r$, —C(O)OR$^r$, —C(S)OR$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —NR$^r$C(O)R$^r$, —NR$^r$C(S)R$^r$, —NR$^r$S(O)$_2$R$^r$, —NHC(O)NHR$^r$, NHC(S)NHR$^r$, —NR$^r$C(O)NH$_2$, NR$^r$C(S)NH$_2$, —NR$^r$C(O)NHR$^r$, —NR$^r$C(S)NHR$^r$, —NHC(O)NR$^r$R$^r$, NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, NR$^r$S(O)$_2$NR$^r$R$^r$, —NHR$^r$, or NR$^r$R$^r$ is selected from the group consisting of fluoro and —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided, however, that any substitution of the C$_{3-6}$ alkenyl or C$_{3-6}$ alkynyl carbon bound to any O, S, or N, of —OR$^r$, —SR$^r$, —C(O)OR$^r$, —C(S)OR$^r$, —C(O)NHR$^r$, —C(S)NR$^r$, —C(O)NR$^r$R$^r$, C(S)NR$^r$R$^r$S(O)$_2$NHR$^r$, —S(O)$_2$NR$^r$R$^r$, —C(NH)NHR$^r$, —NR$^r$C(O)R$^r$, —NR$^r$C(S)R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NHC(S)NHR$^r$, —NHC(O)NR$^r$R$^r$, —NH C(S)NR$^r$R$^r$, —NR$^r$C(O)NR$^r$, —NR$^r$C(S)NR$^r$R$^r$, —NHS(O)$_2$NHR$^r$, —NR$^r$S(O)$_2$NH$_2$, —NR$^r$S(O)$_2$NR$^r$R$^r$, —NHS(O)$_2$NR$^r$R$^r$, —NR$^r$S(O)$_2$NR$^r$R$^r$, —NHR$^r$, or NR$^r$R$^r$ is selected from the group consisting of fluoro, lower alkyl, fluoro substituted lower alkyl, and —R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or R$^s$ and R$^t$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each R$^u$ is independently selected from the group consisting of lower alkyl, C$_{3-6}$ alkenyl, C$_{3-6}$ alkynyl, cycloalkyl, heterocycloalkyl, aryl, and heteroaryl, wherein lower alkyl is optionally substituted with one or more, preferably 1, 2, 3, 4 or 5, also 1, 2, or 3 substituents selected from the group consisting of —$R^y$, fluoro, —OH, —$NH_2$, lower alkoxy, fluoro substituted lower alkoxy, lower alkylthio, fluoro substituted lower alkylthio, mono-alkylamino, di-alkylamino, and cycloalkylamino, provided, however, that any substitution of the lower alkyl carbon bound to the O of —$OR^u$, S of —$SR^u$, or N of —$NHR^u$ is fluoro or —$R^y$, and wherein $C_{3-6}$ alkenyl or $C_{3-6}$ alkynyl are optionally substituted with one or more, preferably 1, 2, 3, 4 or 5, also 1, 2, or 3 substituents selected from the group consisting of —$R^y$, fluoro, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided, however, that any substitution of the $C_{3-6}$ alkenyl or $C_{3-6}$ alkynyl carbon bound to the O of —$OR^u$, S of —$SR^u$, or N of —$NHR^u$ is fluoro, lower alkyl fluoro substituted lower alkyl, or —$R^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —$NH_2$, —$NO_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each $R^x$ is selected from the group consisting of lower alkyl, lower alkenyl and lower alkynyl, wherein lower alkyl is optionally substituted with one or more, preferably 1, 2, 3, 4 or 5, also 1, 2, or 3 substituents selected from the group consisting of —$R^y$, fluoro, —OH, —$NH_2$, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, preferably 1, 2, 3, 4 or 5, also 1, 2, or 3 substituents selected from the group consisting of —$R^y$, fluoro, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each $R^y$ is selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —$NH_2$, —$NO_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted $C_{2-6}$ alkyl, optionally substituted lower alkenyl, or optionally substituted lower alkynyl are optionally substituted with one or more, also 1, 2 or 3 groups or substituents selected from the group consisting of fluoro, —$NO_2$, —CN, —$OR^{1a}$, —$SR^{1a}$, —$NR^{1a}R^{1a}$, —$OC(O)R^{1a}$, —$OC(S)R^{1a}$, —$C(O)R^{1a}$, —$C(S)R^{1a}$, —$C(O)OR^{1a}$, —$C(S)OR^{1a}$, —$C(O)NR^{1a}R^{1a}$, —$C(S)NR^{1a}R^{1a}$, —$S(O)_2NR^{1a}R^{1a}$, —$C(NH)NR^{1a}R^{1a}$, —$NR^{1a}C(O)R^{1a}$, —$NR^{1a}C(S)R^{1a}$, —$NR^{1a}S(O)_2R^{1a}$, —$NR^{1a}C(O)NR^{1a}R^{1a}$, —$NR^{1a}C(S)NR^{1a}R^{1a}$, —$NR^{1a}S(O)_2NR^{1a}R^{1a}$, —$S(O)R^{1a}$, —$S(O)_2R^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —$NO_2$, —CN, —$OR^{1a}$, —$SR^{1a}$, —$NR^{1a}R^{1a}$, —$OC(O)R^{1a}$, —$OC(S)R^{1a}$, —$C(O)R^{1a}$, —$C(S)R^{1a}$, —$C(O)OR^{1a}$, —$C(S)OR^{1a}$, —$C(O)NR^{1a}R^{1a}$, —$C(S)NR^{1a}R^{1a}$, —$S(O)_2NR^{1a}R^{1a}$, —$C(NH)NR^{1a}R^{1a}$, —$NR^{1a}C(O)R^{13}$, —$NR^{1a}C(S)R^{1a}$, —$NR^{1a}S(O)_2R^{1a}$, —$NR^{1a}C(O)NR^{1a}R^{1a}$, —$NR^{1a}C(S)NR^{1a}R^{1a}$, —$NR^{1a}S(O)_2NR^{1a}R^{1a}$, —$S(O)R^{1a}$, —$S(O)_2R^{1a}$, —$R^{1b}$, and lower alkyl optionally substituted with one or more, also 1, 2 or 3 groups or substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino, and —$R^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 groups or substituents selected from the group consisting of halogen, —$NO_2$, —CN, —$OR^{12}$, —$SR^{1a}$, —$NR^{1a}R^{1a}$, —$OC(O)R^{1a}$, —$OC(S)R^{1a}$, —$C(O)R^{1a}$, —$C(S)R^{1a}$, —$C(O)OR^{1a}$, —$C(S)OR^{1a}$, —$C(O)NR^{1a}R^{1a}$, —$C(S)NR^{1a}R^{1a}$, —$S(O)_2NR^{1a}R^{1a}$, —$C(NH)NR^{1a}R^{1a}$, —$NR^{1a}C(O)R^{1a}$, —$NR^{1a}C(S)R^{1a}$, —$NR^{1a}S(O)_2R^{1a}$, —$NR^{1a}C(O)NR^{1a}R^{1a}$, —$NR^{1a}C(S)NR^{1a}R^{1a}$, —$NR^{1a}S(O)_2NR^{1a}R^{1a}$, —$S(O)R^{1a}$, —$S(O)_2R^{1a}$, —$R^{1b}$, and lower alkyl optionally substituted with one or more, also 1, 2 or 3 groups or substituents selected from the group consisting of fluoro, —OH, —$N_2$, lower alkoxy, fluoro substituted lower alkoxy, lower alkylthio, fluoro substituted lower alkylthio, mono-alkylamino, di-alkylamino, and —$R^{1b}$, wherein $R^{1a}$ is selected from the group consisting of hydrogen, provided, however, that hydrogen is not bound to any of C(S), C(O), S(O), or $S(O)_2$ of —$OC(O)R^{1a}$, —$OC(S)R^{1a}$, —$C(O)R^{1a}$, —$C(S)R^{1a}$, —$NR^{1a}C(O)R^{1a}$, —$NR^{1a}C(S)R^{1a}$, —$NR^{1a}S(O)_2R^{1a}$, —$S(O)R^{1a}$, or —$S(O)_2R^{1a}$, —$R^{1b}$, and lower alkyl optionally substituted with one or more, also 1, 2 or 3 groups or substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino, and —$R^{1b}$, provided, however, that any substitution of the alkyl carbon bound to O, S, or N of —$OR^{1a}$, —$SR^{1a}$, —$NR^{1a}R^{1a}$, —$C(O)OR^{1a}$, —$C(S)OR^{1a}$, —$C(O)NR^{1a}R^{1a}$, —$C(S)NR^{1a}R^{1a}$, —$S(O)_2NR^{1a}R^{1a}$, —$C(NH)NR^{1a}R^{1a}$, —$NR^{1a}C(O)R^{1a}$, —$NR^{1a}C(S)R^{1a}$, —$NR^{1a}S(O)_2R^{1a}$, —$NR^{1a}C(O)NR^{1a}R^{1a}$, —$NR^{1a}C(S)NR^{1a}R^{1a}$, or —$NR^{1a}S(O)_2NR^{1a}R^{1a}$, is fluoro or —$R^{1b}$, and wherein —$R^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —$NH_2$, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted $C_{2-6}$ alkyl, optionally substituted lower alkenyl, or optionally substituted lower alkynyl are optionally substituted with one or more, also 1, 2 or 3 groups or substituents selected from the group consisting of fluoro, —CN, —OR$^{1a}$, —SR$^{1a}$, —NR$^{1a}$R$^{1a}$, —C(O)R$^{1a}$, —C(S)R$^{1a}$, —C(O)OR$^{1a}$, —C(O)NR$^{1a}$R$^{1a}$, —C(S)NR$^{1a}$R$^{1a}$, —S(O)$_2$NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, —S(O)$_2$R$^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OR$^{1a}$, —SR$^{1a}$, —NR$^{1a}$R$^{1a}$, —C(O)R$^{1a}$, —C(S)R$^{1a}$, —C(O)OR$^{1a}$, —C(O)NR$^{1a}$R$^{1a}$, —C(S)NR$^{1a}$R$^{1a}$, —S(O)$_2$NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 groups or substituents selected from the group consisting of halogen, —CN, —OR$^{1a}$, —SR$^{1a}$, —NR$^{1a}$R$^{1a}$, —C(O)R$^{1a}$, —C(S)R$^{1a}$, —C(O)OR$^{1a}$, —C(O)NR$^{1a}$R$^{1a}$, —C(S)NR$^{1a}$R$^{1a}$, —S(O)$_2$NR$^{1a}$, R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, wherein R$^{1a}$ is selected from the group consisting of hydrogen, provided, however, that hydrogen is not bound to any of C(S), C(O), S(O), or S(O)$_2$ of —C(O)R$^{1a}$, —C(S)R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, or —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, provided, however, that any substitution of the alkyl carbon bound to O, S, or N of —R$^{1a}$, —SR$^{1a}$, —NR$^{1a}$R$^{1a}$, —C(O)OR$^{1a}$, —C(O)NR$^{1a}$R$^{1a}$, —C(S)NR$^{1a}$R$^{1a}$, —S(O)$_2$NR$^{1a}$R$^{1a}$, —NR$^{1a}$C(O)R$^{1a}$, —NR$^{1a}$C(S)R$^{1a}$, or —NR$^{1a}$S(O)$_2$R$^{1a}$, is fluoro or —R$^{1b}$, and wherein —R$^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

"Lower alkoxy" denotes the group —OR$^z$, where R$^z$ is lower alkyl. "Substituted lower alkoxy" denotes lower alkoxy in which R$^z$ is lower alkyl substituted with one or more substituents as indicated herein, for example, in the description of compounds of Formula I, Formula II, or Formula III, including descriptions of substituted cycloalkyl, cycloheteroalkyl, aryl and heteroaryl, attached at any available atom to produce a stable compound. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Lower alkylthio" denotes the group —SR$^{aa}$, where R$^{aa}$ is lower alkyl. "Substituted lower alkylthio" denotes lower alkylthio in which R$^{aa}$ is lower alkyl substituted with one or more substituents as indicated herein, for example, in the description of compounds of Formula I, Formula II, or Formula III, including descriptions of substituted cycloalkyl, cycloheteroalkyl, aryl and heteroaryl, attached at any available atom to produce a stable compound. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. While it is understood that substitutions on alkylthio are attached at any available atom to produce a stable compound, substitution of alkylthio is such that O, S, or N (except where N is a heteroaryl ring atom), are not bound to the alkyl carbon bound to the alkylthio S. Further, where alkylthio is described as a substituent of another moiety, the alkylthio sulfur is not bound to a carbon atom that is bound to an O, S, or N of the other moiety (except where N is a heteroaryl ring atom), or to an alkene or alkyne carbon of the other moiety.

"Amino" or "amine" denotes the group —N$_2$. "Mono-alkylamino" denotes the group —NHR$^{bb}$ where R$^{bb}$ is lower alkyl. "Di-alkylamino" denotes the group NR$^{bb}$R$^{cc}$, where R$^{bb}$ and R$^{cc}$ are independently lower alkyl. "Cycloalkylamino" denotes the group —NR$^{dd}$R$^{ee}$, where R$^{dd}$ and R$^{ee}$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. While it is understood that when mono-alkylamino, di-alkylamino, or cycloalkylamino are substituents on other moieties that are attached at any available atom to produce a stable compound, the nitrogen of mono-alkylamino, di-alkylamino, or cycloalkylamino as substituents is not bound to a carbon atom that is bound to an O, S, or N of the other moiety.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated, In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

As used herein, the terms "ligand" and "modulator" are used equivalently to refer to a compound that changes (i.e., increases or decreases) the activity of a target biomolecule, e.g., an enzyme such as a kinase. Generally a ligand or modulator will be a small molecule, where "small molecule refers to a compound with a molecular weight of 1500 daltons or less, or preferably 1000 daltons or less, 800 daltons or less, or 600 daltons or less. Thus, an "improved ligand" is one that possesses better pharmacological and/or pharmacokinetic properties than a reference compound, where "better" can be defined by one skilled in the relevant art for a particular biological system or therapeutic use.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

As used herein in connection with compounds of the invention, the term "synthesizing" and like terms means chemical synthesis from one or more precursor materials.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein in connection with amino acid or nucleic acid sequence, the term "isolate" indicates that the sequence is separated from at least a portion of the amino acid and/or nucleic acid sequences with which it would normally be associated.

in connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

The present invention concerns compounds of Formula I, and all sub-generic formulae, compounds of Formula II and all sub-generic formulae, and compounds of Formula III and all sub-generic formulae that are modulators of protein kinases, for example without limitation, the compounds are modulators of at least one of the kinases selected from the group consisting of Ab1, Akt1, Akt2, Akt3, ALK, Alk5, B-Raf. Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, 1Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, and the use of such compounds in the treatment of diseases or conditions.

Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Description of specific target protein kinases contemplated by the present invention may be found, for example, in U.S. patent application Ser. No. 11/473,347 (PCT publication WO2007002433), the disclosure of which is hereby incorporated by reference in its entirety, in addition to the following:

Exemplary Diseases Associated with Raf Kinases

A-Raf: Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RB3D (i.e., Ras binding domain) and phorbol-ester/DAG-type zinc finger domain and is involved in the transduction of mitogenic signals from the cell membrane to the nucleus. A-Raf inhibitors may be useful in treating neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myclodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf: Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine, threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS->Raf->MEK->ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAF inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat. Genet. 2006, 38(3):294-6).

c-Raf-1: Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to the mitochondria by BCL2 (i.e., oncogene B-cell leukemia 2) which is a regulator of apoptotic cell death Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. C-Raf-1 is also implicated as an important mediator of tumor angiogenesis (Hood, J. D. et al., 2002, Science 296, 2404). C-Raf-1 inhibitors may also be useful for the treatment of acute myeloid leukemia and myelodysplastic syndromes (Crump, Curr Pharm Des 2002, 8(25):2243-8). Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2):139-42).

B-Raf and/or C-Raf inhibitors may be useful in treating A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute mycloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases, including, but not limited to, heart failure, ischemic stroke, cardiac hypertrophy, thrombosis (e.g. thrombotic microangiopathy syndromes), atherosclerosis, and reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to, *Helicobacter pylori*, Hepatitis and influenza viruses, fever, and sepsis; pulmonary diseases, including, but not limited to, chronic obstructive pulmonary disease (COPD) and acute respiratory distress syndrome (ARDS); genetic developmental diseases, including, but not limited to, Noonan's syndrome, Costello syndrome, (facio-cutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases.

Exemplary Diseases Associated with c-Kit.

The compounds described herein are useful for treating disorders related to c-kit e.g., diseases related to unregulated kinase signal transduction, including cell proliferative disorders, fibrotic disorders and metabolic disorders, among others. As described in more detail below and in Lipson et al., U.S. 20040002534 (U.S. application Ser. No. 10/600,868, filed Jun. 23, 2003) which is incorporated herein by reference in its entirety, cell proliferative disorders which can be treated by the present invention include cancers, and mast cell proliferative disorders.

The presence of c-kit has also been associated with a number of different types of cancers. In addition, the association between abnormalities in c-kit and disease are not restricted to cancer. As such, c-kit has been associated with malignancies, including, but not limited to, mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including, but not limited to, asthma, rheumatoid arthritis, allergic rhinitis, multiple sclerosis, inflammatory bowel syndrome, transplant rejection, and hypereosinophilia.

Exemplary Diseases Associated with c-fms

The presence of c-fms has been associated with a number of different types of diseases. As such, c-fms has been associated with immune disorders, including rheumatoid arthritis, systemic lupus erythematosis (SLE), and transplant rejection; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic mycloid leukemia (CML), prostate cancer, breast cancer, ovarian cancer, melanoma, glioblastoma multiforme, metastasis of tumors to other tissues, and other chronic myeloproliferative diseases such as myelofibrosis.

Exemplary Diseases Associated with TrkA and TrkB

TrkA: Target kinase TrkA (i.e., neurotrophic tyrosine kinase, receptor, type 1) is a 140 kDa tyrosine kinase encoded by chromosome 1q21-q22 (symbol: NTRK1). TrkA inhibitors may be useful in treating pain (e.g. chronic pain, neuropathic pain), cancer (e.g. prostate cancer, lung cancer, myeloid leukemia, pancreatic cancer), allergic disorders (e.g. asthma), arthritis, diabetic retinopathy, macular degeneration and psoriasis.

TrkA is a plasma member receptor composed of an extracellular domain (responsible for high affinity binding to nerve growth factor, NGF), a transmembrane segment and an intracellular protein tyrosine kinase domain (responsible to transmit the NGF signal to initiate and coordinate neuronal responses). NGF binding induces TrkA clustering on the membrane and activates the kinase. The kinase initiates a cascade of protein phosphorylation events through multiple pathways including SHC/Ras/MAPK, PI3K and PLCg1. A TrkA kinase inhibitor would not prevent NGF/TrkA binding, but could prevent down-stream signal transduction.

Nerve Growth Factor (NGF) is produced by a number of tissues and inflammatory cells during tissue injury and host immune response. It initiates and maintains hypersensitivity to incoming stimulus (hyperalgesia) and the perception of non-noxious stimuli (allodynia). Through its high-affinity receptor TrkA, NGF increases the excitation state of sensory neurons leading to the central nervous system (peripheral sensitization), and increases transmitter release from the dorsal spinal cord (central sensitization). In clinical trials, a single NGF subcutaneous injection generated local hyperalgesia persisting up to 7 weeks. At doses above 0.1 microgram/kg, NGF caused muscle pain that varied from mild to moderate, primarily in the bulbar and truncal musculature. Intravenous NGF produced earlier and more pronounced systemic effects (Petty et al, 1994, Ann Neurol. 36: 244-6). Conversely, TrkA kinase inhibitors could be used to treat diseases of enhanced states of nociception.

In Complete Freund's Adjuvant (CFA)-induced hind-paw inflammation, spinal nerve ligation and streptozoticin-induced neuropathic pain models, a single intraperitoneal injection of anti-NGF reversed established tactile allodynia from day 3 to day 7 following treatment. In the mouse CCI model, anti-NGF reversed tactile allodynia when administered 2 weeks after surgery. Repeated administration of this antibody to CCI mice for 3 weeks produced a sustained reversal of tactile allodynia (Wild et al, 2007, J. Pharmacol. Exp. Ther. 322:282-287).

Prostate tumors that have metastasized to bone frequently induce bone pain which can be difficult to fully control as it seems to be driven simultaneously by inflammatory, neuropathic, and tumorigenic mechanisms. Anti-NGF produced a significant reduction in both early and late stage hone cancer pain related behaviors. This therapy did not influence tumor-induced bone remodeling, osteoblast proliferation, osteoclastogenesis, tumor growth, or markers of sensory or sympathetic innervation in the skin or bone. All nerve fibers that innervate the bone express TrkA and p75, and these are the receptors through which NGF sensitizes and/or activates nociceptors (Halvorson et al, 2005, Cancer Res. 65:9426-35).

In patients with mild asthma due to exposure to cat allergen, NGF expression was strongly induced in epithelial cells, fibroblasts, blood vessels, and a few infiltrating cells. TrkA mRNA and protein levels in bronchial biopsies were increased significantly after allergen exposure in infiltrating mast cells before the onset of symptoms (Kassel et al, 2001, Clin Exp Allergy 31:1432-40).

The late phase reaction in asthma following allergen provocation is dominated by an influx of activated eosinophils into the bronchial lumen, which correlates with the release of cosinophilic products into the airways to increase disease severity. The viability and activation of cosinophils from patients with mild asthma were significantly enhanced after NGF stimulation. Addition of neutralizing anti-NGF antibodies ex vivo abrogated the effects (Nassentein et al, 2003, J Exp Med 198:455-467). TrkA kinase inhibitors could decrease this paracrine loop between the respiratory tract and infiltrating mast cells as well as endobronchial cosinophils, and thus be useful for the treatment of asthma and other allergic disorders.

TrkB: Target kinase TrkB (i.e., neurotrophic tyrosine kinase, receptor, type 2) is a 145 kDa tyrosine kinase encoded by chromosome 9q22.1 (symbol: NTRK2). TrkB inhibitors may be useful in treating various cancers and their metastases (e.g. prostate cancer, lung cancer, Wilms tumors, neuroblastoma, and pancreatic cancer), and various neuropathies (e.g. stroke, multiple sclerosis, transverse myelitis, and encephalitis).

In clinical trials with recombinant BDNF, paresthesia was developed at the site of subcutaneous injection (Coulie et al, 2000, Gastroenterology 119:41-50). Intrathecal infusion of BDNF in humans also induced paresthesia and warmth as side effects (Ochs et al, 2000, Amyotroph Lateral Scler Other Motor Neuron Disord. 1:201-6). Chronic paresthesia is often a symptom of an underlying neurological disease or traumatic nerve damage. Paresthesia can be caused by disorders affecting the central nervous system, such as stroke and transient ischemic attacks (mini-strokes), multiple sclerosis, transverse myelitis, and encephalitis. Since BDNF binds to TrkB specifically with high affinity these neuropath effects are mediated through TrkB signaling. Thus Trkb kinase inhibitors could be used to treat certain patients with neuropathy.

BDNF is known to act at the synapses between primary sensory and spinal dorsal horn neurons to affect pain transmission during inflammation. The primary afferent is the only source of BDNF in the spinal cord, and it is up-regulated in the dorsal root ganglion (DRG) by peripheral NGF a few days after inflammation, and is transported and released into the superficial dorsal horn in an activity-dependent manner. TrkB expression in the dorsal horn also increases for a few days after inflammation. These findings suggest that BDNF may act during the restricted period in the early phase of inflammation. Through TrkB, BDNF activates two distinct channels: (1) transient receptor potential canonicals (TRPC3), which produces a slow response by opening of a non-selective cation channel; and (2) Na+ channel, which mediates a rapid depolarization in the hippocampus. These channels have been strongly associated with inflammatory pain. Anti-BDNF significantly increased the withdrawal threshold in CFA-treated rats, a model of inflammatory pain. Since the swelling at the site of CFA injection was not affected by antiserum, the residual component might be due to peripheral sensitization (Matayoshi et al, 2005, J. Physiol. 569:685-95).

In patients with neuroblastomas, co-expression of TrkB and BDNF, co-expression of TrkB with N-Myc amplification, and expression of truncated TrkB are found to be associated with poorer clinical outcome (Nakagawara et al, 1994, Mol Cell Biol. 14:759-767). Co-expression of TrkB with its ligand BDNF could generate a positive feedback loop through autocrine and paracrine loops. Also TrkB truncations found in these tumors generate activated forms of the intracellular protein tyrosine kinase. The constitutively active TrkB signals through multiple pathways to promote cancer initiation, progression and metastasis. These truncated TrkB kinases were also found in hepatocellular carcinoma (Yang et al, 2005, Cancer. Res 65:219-225). Thus TrkB inhibitors could be used to treat a sub-population of cancer patients with an activated TrkB pathway.

In patients with pancreatic cancer, TrkB expression is correlated with perineural invasion, positive retroperitoneal margin, and shorter latency to development of liver metastasis (Selabas et al, 2005, Clin. Cancer. Res VI 1:440-449). Mechanistically, TrkB activates the PI3K pathway to suppress anoikis (apoptosis resulting from loss of cell-matrix interactions) which is one of the physiological barriers to metastasis. TrkB kinase inhibition could break down resistance to anoikis of metastasizing tumors (Douma et al, 2004, Nature 430: 1034-9). Therefore, TrkB inhibitors could have utility in a broad range of tumor types.

Exemplary Diseases Associated with MAPK4K

MAP4K4: Target kinase MAP4K4 (i.e., Mitogen-activated protein kinase kinase 4, aka Hematopoietic progenitor kinase/Germinal center kinase-like Kinase) is a 130 kDa serine/threonine kinase encoded by chromosome 2q11.2-q12 (symbol: MAP4K4) and is also known as HGK. It is a member of the human STE20/mitogen-activated protein kinase kinase kinase kinase (MAP4K) family of serine/threonine kinases and is the human ortholog of mouse NtK (Nck-interacting kinase). The N-terminus of the mature HGK protein has a catalytic kinase domain that shares 47% and 48% amino acid sequence identity to the catalytic domain of Hematopoietic progenitor kinase 1 (HPK1) and Germinal center kinase (GCK), respectively. Yao et al. (J. Biol. Chem. 274: 2118-2125, 1999) identified 2 HGK isoforms, one of which has no proline-rich domains, and another, longer variant that contains such domains and appears to be expressed in brain only. Northern blot analysis revealed expression of 3 HGK transcripts of approximately 4.6, 6.5, and 8.5 kb in heart, brain, skeletal muscle, pancreas, placenta, liver, lung, and kidney. By Western blot analysis with a polyclonal antibody, Yao et al. (J. Biol. Chem. 274: 2118-2125, 1999) found that the 130-kD protein is expressed in multiple cell lines.

Expression of HGK in transfected cell lines resulted in strong JNK activation and, in turn, c-jun transcriptional activity (Yao et al. J. Biol. Chem. 274: 2118-2125, 1999). HGK-induced JNK activation was inhibited by dominant-negative MAP2K4, MAP2K7, and TAK1 mutants. TNF-alpha also stimulated HGK kinase activity. HGK was identified as a putative effect of Rap2 to activate JNK (Machida et al. J, Biol. Chem. 279: 15711-15714, 2004). This link establishes HGK as a potential target for a range of metabolic indications, since the JNK pathway clearly antagonizes insulin signaling. An HGK inhibitor could re-sensitize fat and muscle cells to insulin.

HGK is found to be broadly expressed in human tumor cells and can modulate cellular transformation, invasion, and adhesion (Wright et al. Mol. Cell. Biol. 23: 2068-2082, 2003). Wright et al showed HGK to be highly expressed in most tumor cell lines relative to normal tissue. An active role for this kinase in transformation was suggested by an inhibition of H-Ras (V12)-induced focus formation by expression of inactive, dominant-negative mutants of HGK in both fibroblast and epithelial cell lines. Expression of an inactive mutant of HGK also inhibited the anchorage-independent growth of cells yet had no effect on proliferation in monolayer culture. Expression of HGK mutants modulated integrin receptor expression and had a striking effect on hepatocyte growth factor-stimulated epithelial cell invasion. Together, these results suggest an important role for HGK in cell transformation and invasiveness. More recently, a small interfering RNA screen for modulators of tumor cell motility identifies MAP4K4 as a promigratory kinase (Collins et al. Proc. Natl. Acad. Sci. USA, 103: 3775-3780, 2006). Collins et al. showed that the knockdown of the HGK transcript inhibited the migration of multiple carcinoma cell lines, indicating a broad role in cell motility, and potently suppressed the invasion of SKOV-3 cells in vitro. The effect of HGK on cellular migration was found to be mediated through JNK kinase, independent of AP1 activation and downstream transcription. Accordingly, small molecule inhibition of c-Jun N-terminal kinase suppressed SKOV-3 cell migration, underscoring the potential therapeutic utility of mitogen-activated protein kinase pathway inhibition in cancer progression (Collins et al. Proc. Natl. Acad. Sci. USA, 103: 3775-3780, 2006). These studies strongly support HGK as a target in a broad range of oncology indications. In particular, an HGK inhibitor could have utility in blocking the migration, invasion and metastasis in many different tumor types.

Activation of T-cells by antigens initiates a complex series of signal-transduction events that are critical for immune responses Mack et al. (Immunol. Lett, 96, 129-145, 2005) developed a genetic screen to survey the functional roles of kinases in antigen mediated T-cell activation and identified 19 protein kinases that were previously implicated in T-cell signaling processes and 12 kinases that were not previously linked to T-cell activation, including HGK. siRNA studies showed a role for HGK in antigen mediated T-cell responses in Jurkat and primary T-cells. In addition, by analyzing multiple promoter elements using reporter assays, Mack et al.

have shown that MAP4K4 is implicated in the activation of the TNF-alpha promoter. Therefore, inhibition of HGK could have broad therapeutic utility for T-cell-mediated autoimmune diseases.

Insulin-regulated glucose transporter GLUT4 is a key modulator of whole body glucose homeostasis, and its selective loss in adipose tissue or skeletal muscle causes insulin resistance and diabetes. Using an RNA interference-based screen, Tang et al. (Proc Natl Acad Sci USA. 103:2087-2092, 2006) found 4 negative regulators of insulin-responsive glucose transport in mouse adipocytes: Pctk1, Pftk1, Ikbka (CHUK), and HGK. HGK suppressed expression of adipogenic transcription factors, C/EBPA, C/EBPB, and PPARG, and it suppressed surface expression of GLUT4 (SLC2A4), resulting in attenuated membrane hexose transport activity. RNA interference-mediated depletion of HGK early in differentiation enhanced adipogenesis and triglyceride deposition; in fully differentiated adipocytes, loss of HGK upregulated GLUT4 expression. Conversely, conditions that inhibited adipogenesis, such as TNF-alpha treatment or PPARG depletion, markedly upregulated HGK. Tang et al. (Proc Natl Acad Sci USA. 103:2087-2092, 2006) concluded that MAP4K4-dependent signaling inhibited PPARG-responsive gene expression, adipogenesis, and insulin-stimulated glucose transport. Furthermore, TNF-alpha signaling to down-regulate GLUT4 is impaired in the absence of HGK, indicating that HGK expression is required for optimal TNF-alpha action. This study further supports HGK as a target in metabolic disease, and suggests a role for HGK inhibition in ameliorating the pathology in adipocytes.

In a separate study (Bouzakri and Zierath J. Biol. Chem. 282:7783-7789, 2007), using small interfering RNA (siRNA) to suppress the expression of HGK protein 85% in primary human skeletal muscle cells, TNF-alpha-induced insulin resistance on glucose uptake was completely prevented. HGK silencing inhibited TNF-alpha-induced negative signaling inputs by preventing excessive JNK and FE-1/2 phosphorylation, as well as IRS-1 serine phosphorylation. These results highlight the HGK/JNK/ERK/IRS module in the negative regulation of insulin signaling to glucose transport in response to TNF-alpha. Depletion of HGK also prevented TNF-alpha-induced insulin resistance on AKT and the AKT substrate 160 (AS160), providing evidence that appropriate insulin signaling inputs for glucose metabolism were rescued. The authors suggested that strategies to inhibit HGK may be efficacious in the prevention of TNF-alpha-induced inhibitory signals that cause skeletal muscle insulin resistance on glucose metabolism in humans. Moreover, in myotubes from insulin-resistant type II diabetic patients, siRNA against HGK restored insulin action on glucose uptake to levels observed in healthy subjects. This study further supports HGK as a target in metabolic diseases such as type II diabetes, and suggests a role for HGK inhibition in ameliorating the pathology in muscle cells.

HGK inhibitors may be useful in treating metabolic indications, including re-sensitizing fat and muscle cells to insulin, ameliorating the pathology in adipocytes, ameliorating the pathology in muscle cells, metabolic syndrome and type II diabetes; a broad range of oncology indications, including blocking the migration, invasion and metastasis in many different tumor types; and T-cell mediated autoimmune diseases.

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry Reactions, Mechanisms and Structure*, New York, McGraw Hill. Thus, the techniques useful to synthesize a potential modulator of kinase function are readily available to those skilled in the art of organic chemical synthesis.

Regarding the synthetic examples described herein, solvents include polar and non-polar solvents known to those of skill in the art, including polar aprotic and polar protic solvents. Polar solvents include, without limitation, protic solvents such as methanol, ethanol, isopropyl alcohol, t-butanol, n-butanol, acetic acid, formic acid or water, or aprotic solvents such as tetrahydrofuran (THF), acetonitrile, dioxane, methylene chloride, dimethylsulfoxide (DMSO), acetone, N,N-dimethylformamide (DMF), N,N-dimethylacetamide (DMA), ethyl acetate. 1,2-dimethoxyethane, 1,2-dichloroethane, chloroform, 1,2-dichloroethane, or pyridine. Polar solvents include a mixture of water with any of the above, or a mixture of any two or more of the above. Apolar solvents include, without limitation, toluene, benzene, chlorobenzene, xylenes and hexanes.

Regarding the synthetic examples described herein, reducing agent includes, without limitation, a reducing agent such as catalytic reducing agents using hydrogen and transition metal catalysts such as palladium, platinum, rhodium, etc. (e.g. Pt/acetic acid/$H_2$); a mixture of trifluoroacetic acid and triethylsilane, borane tetrahydrofuran complex, diborane, borane dimethylsulfide complex, and a combination of sodium borohydride and boron trifluoride; metals such as reduced iron, zinc powder, magnesium etc.; metal hydrogen complex compounds such as alkali metal borohydrides (for example, potassium borohydride, sodium borohydride, lithium borohydride, zinc borohydride, sodium triacetoxyborohydride, etc.), aluminum lithium hydride, etc.; metal hydrides such as sodium hydride, etc.; organic tin compounds (triphenyltin hydride, etc.); and metal salts such as nickel compounds, zinc compounds, tin compounds (for example tin(II) chloride), and samarium iodide/pivalic acid/hexamethylphorphoric triamide.

Regarding the synthetic examples described herein, oxidizing agent includes, without limitation, an oxidizing agent such as Dess-Martin reagent, TEMPO (2,2,6,6-tetramethylpiperidine-N-oxide), DDQ (2,3-Dichloro-5,6-dicyano-1,4-benzoquinone), PDC (pyridinium dichromate), PCC (pyridinium chlorochromate), Pyridine.SO3, Chromium trioxide, p-nitroperbenzoic acid, magnesium monoperoxyphthalate, sodium periodate, potassium periodate, hydrogen peroxide, urea peroxide, alkali metal bromates, cumene hydroperoxide, tert-butyl peroxide, peracids such as performic acid, peracetic acid, pertrifluoroacetic acid, perbenzoic acid, m-chloroperbenzoic acid, o-carboxyperbenzoic acid and the like; sodium metaperiodate, bichromic acid; bichromates such as sodium bichromate, potassium bichromate; permanganic acid: permanganates such as potassium permanganate, sodium permanganate; and lead salts such as lead tetraacetate.

Regarding the synthetic examples described herein, a nitrogen protecting group is a chemical group covalently bound to a nitrogen atom of a compound that is used to protect the nitrogen from reaction during a synthetic step. The nitrogen protecting group may be added to a compound and removed in a subsequent step by methods known to those of skill in the art. Nitrogen protecting groups include, without limitation, carbamates, amides, N-sulfonyl derivatives, groups of formula —C(O)OR, wherein R is, for example, methyl, ethyl, t-butyl, benzyl, phenylethyl, $CH_2$=$CHCH_2$—, and the like, groups of the formula —C(O)R', wherein R' is, for example, methyl, phenyl, trifluoromethyl, and the like, groups of the formula —$SO_2$R", wherein R" is, for example, tolyl, phenyl, trifluoromethyl. 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like. Other suitable nitrogen protecting groups may be found in texts such as T. W. Greene & P. G. M. Wuts, *Protective Groups in Organic Synthesis*, John Wiley & Sons, 1991.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, such as (a) Isomers, Prodrugs, and Active Metabolites (b) Tautomers, Stereoisomers, Regioisomers, and Solvated Forms (c) Prodrugs and Metabolites (d) Pharmaceutically acceptable salts and (e) Polymorphic forms, are described, for example, in U.S. patent application Ser. No. 11/473,347 (see also, PCT publication WO2007002433), the disclosure of which is hereby incorporated by reference in its entirety.

Administration

The methods and compounds will typically be used in therapy for human subjects. However, they may also be used to treat similar or identical indications in other animal subjects. In this context, the terms "subject," "animal subject," and the like refer to human and non-human vertebrates, e.g. mammals, such as non-human primates, sports and commercial animals, e.g., equines, bovines, porcines, ovines, rodents, and pets, e.g., canines and felines. A description of possible methods and routes of administration may be found, for example, in U.S. patent application Ser. No. 11/473,347 (see also, PCT publication WO2007002433), the disclosure of which is hereby incorporated by reference in its entirety.

EXAMPLES

Examples related to the present invention are described below. In most cases, alternative techniques can be used. The examples are intended to be illustrative and are not limiting or restrictive to the scope of the invention. In some examples, the mass spectrometry result indicated for a compound may have more than one value due to the isotope distribution of an atom in the molecule, such as a compound having a bromo or chloro substituent.

Unless specifically indicated otherwise, the Formula enumeration and R group enumeration used in the following examples is not related to such enumeration in other sections of this application. The reagents and solvents used in these examples can be readily substituted with appropriate alternatives as are known in the art and isolation of products is readily achieved by methods known in the art, including, but not limited to, extraction, crystallization, and chromatographic methods. In addition to the following Examples, exemplary methods for synthesis of compounds of the present invention may be found in U.S. patent application Ser. No. 11/473,347 (see also, PCT publication WO2007002433), the disclosure of which is hereby incorporated by reference in its entirety. The 1H-pyrrolo[2,3-b]pyridine core of compounds described in the examples may also be referred to as 7-azaindole in the examples.

Example 1

Synthesis of Compounds of Formula X

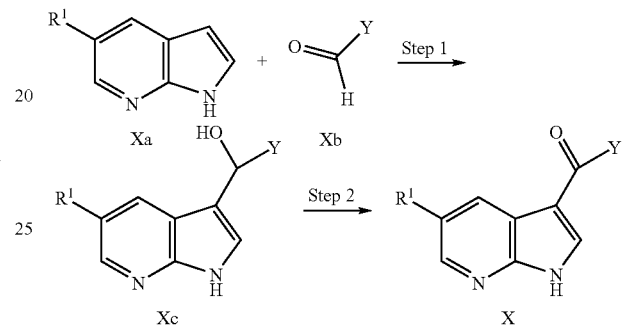

Step 1—Preparation of Compounds of Formula Xc and Xd

To a compound of Formula Xa ($R^1$ is as defined) and a compound of Formula Xb (Y is consistent with compounds of Formula I, Formula II, or Formula III, e.g. Y is:

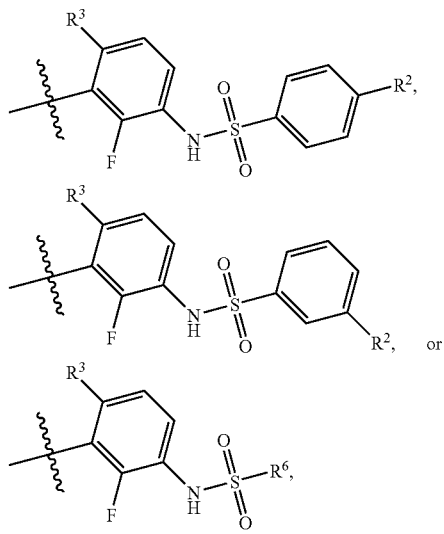

where $R^2$ and $R^3$ are as defined, and $R^6$ is as defined, where

indicates the attachment point to the carbonyl carbon) is added an appropriate solvent (e.g. methanol) followed by an appropriate base (e.g. potassium hydroxide, sodium methoxide). The reaction is typically allowed to stir at room temperature overnight. Isolation by conventional means (e.g. extraction, washing and filtering) affords a mixture containing compound of Formula Xc, which may be isolated by silica gel chromatography if desired.

Step 2—Preparation of Compounds of Formula X

To a compound of Formula Xc in an appropriate solvent (e.g. tetrahydrofuran) is added an oxidizing agent (e.g. Dess-Martin periodane, TEMPO, DDQ). Typically, the reaction is allowed to stir at room temperature for 20 minutes. Isolation by conventional means (e.g. extraction and silica gel column chromatography) affords compounds of Formula X.

Example 2

Synthesis of Compounds of Formula X

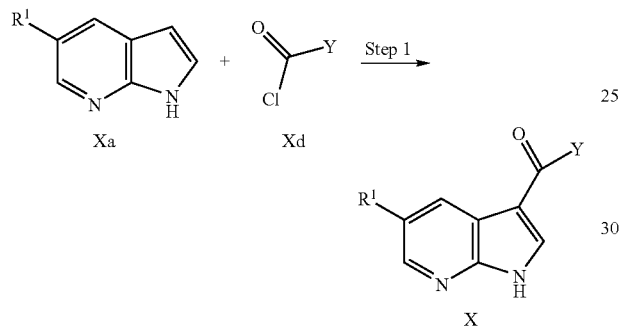

Step-1—Synthesis of Compound of Formula X

Compound of Formula X is synthesized by reacting a compound of Formula Xa (see Example 1) with a compound of Formula Xd (Y is as defined in Example 1), e.g. benzoyl chloride, in the presence of a Lewis acid (e.g. aluminum trichloride) in an inert solvent (e.g. dichloromethane) under an inert atmosphere (e.g. argon) at room temperature or with heating up to reflux for 1-18 hours. The desired compound X is isolated by extraction and silica gel column chromatography, Example 3

Synthesis of Compounds of Formula X

Step-1—Synthesis of Compound Xe

Compound of Formula Xc can be synthesized by reacting a compound of Formula Xa (see Example 1) with hexamethyltetramine and acetic acid in water with heating to reflux for two hours. After cooling, the desired compound precipitates and may be collected by filtration.

Step-2—Synthesis of Compound of Formula Xf

Compound of Formula Xf, where P is a nitrogen protecting group, is synthesized by reacting a compound Xe with an appropriate reagent to introduce a protecting group (e.g. tri-isopropylsilylchloride) and a base (e.g. sodium hydride) in a solvent (e.g. tetrahydrofuran) typically at room temperature for 3-12 hours. The desired compound is isolated by conventional means (e.g. extraction).

Step-3—Synthesis of Compound of Formula Xh

Compound of Formula Xh is synthesized by reacting a compound of Formula Xf in a solvent (e.g. tetrahydrofuran) with an organolithium reagent (e.g. phenyl lithium) in a solvent (e.g. tetrahydrofuran) under an inert atmosphere, cooled to −78° C. An appropriate organolithium reagent can also be prepared by reacting compounds of Formula Xg, where $Y^1$ is or —R⁶

indicates attachment point to the sulfone), where $R^2$, $R^1$ and $R^6$ are as defined in Example 1, with an organolithium reagent (e.g. butyllithium) in a solvent (e.g. tetrahydrofuran) under an inert atmosphere, cooled to −78° C. The reaction is typically allowed to warm to room temperature and stirred for 30 minutes. The desired compound is isolated by conventional means (e.g. extraction).

Step-4—Synthesis f an Intermediate of Compound of Formula X

An intermediate of compound of Formula X is synthesized by reacting a compound of Formula Xh with an appropriate reagent to remove the protecting group, P, (e.g. tetra-n-butyl ammonium fluoride) in an appropriate solvent (e.g. tetrahydrofuran). The final product is isolated by standard procedures (e.g. extraction).

Step-5—Synthesis of Compound of Formula X

Compound of Formula X is synthesized by reacting the intermediate from Step 4 with an oxidizing agent (e.g. Dess-Martin periodane, TEMPO) in an aprotic solvent (e.g. tetrahydrofuran) typically at room temperature for 20 minutes. The desired compound is isolated by conventional means (e.g. extraction and silica gel chromatography).

Example 4

Synthesis of phenyl-(1H-pyrrolo[2,3-b]pyridine-5-yl)-amine 4

Phenyl-(-1H-pyrrolo[2,3-b]pyridine-5-yl)-amine 1 was synthesized in three steps from 5-bromo-7-azaindole 1 as shown in Scheme 1.

Scheme 1

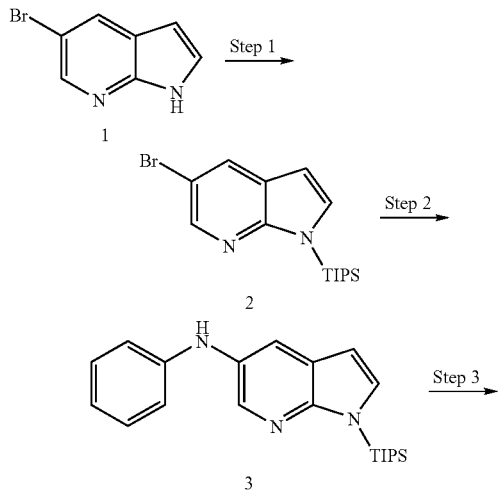

-continued

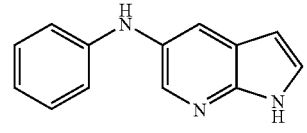

Step 1—Preparation of 5-bromo-1-triisopropylsitaoyl-1H-pyrrolo[2,3-b]pyridine (2)

To 5-bromo-7-azaindole (1, 1.5 g, 7.6 mmol) in N,N-dimethylformamide (20 mL) were added sodium hydride (60% in mineral oil, 0.27 g, 11.0 mmol) and trriisopropylsilyl chloride (2.6 mL, 12.0 mmol), under an atmosphere of nitrogen. The reaction was stirred for 2 hours at room temperature. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to give the compound (2, 1.6 g, 59%). MS (ESI)[M+H⁺]⁺=352.3.

Step 2—Preparation of 5-phenyl-(1-triisopropylsilanyl-1H-pyrrolo[2,3-b]pyridine-5-yl)-amine (3)

To 5-bromo-1-triisopropylsilanyl-1H-pyrrolo[2,3-b]pyridine (2, 0.10 g, 0.3 mmol) in toluene (5 mL) were added aniline (0.04 mL, 0.42 mmol), sodium tert-butoxide (0.15 g, 1.56 mmol), tris(dibenzyllideneacetone)dipalladium(0) (9.2 mg, 0.01 mmol) and (S)-(−)-2,2-bis(diphenylphosphino)-1, 1'-binaphthyl (6.3 mg, 0.01 mmol). The reaction was heated to 160° C. for 10 minutes in a CEM Discover microwave instrument. The reaction was concentrated and purified by silica gel column chromatography eluting with 3% ethyl acetate in hexane to give the compound (3, 40 mg, 40%). MS (ESI)[M+H⁺]⁺=366.6.

Step 3—Preparation of phenyl-(-1H-pyrrolo[2,3-b]pyridine-5-yl)-amine (4)

To 5-phenyl-(1-triisopropylsilanyl-1H-pyrrolo[2,3-b]pyridine-5-yl)-amine (3, 0.14 g, mmol) in tetrahydrofuran (3.0 mL) was added tetra-n-butylammonium fluoride (0.197 g, 0.76 mmol). The reaction was stirred for 1 hour at room temperature. The reaction was concentrated and purified by silica gel column chromatography eluting with 3% ethyl acetate in hexane to give the compound (4, 60 mg, 76%). MS (ESI)[M+H⁺]⁺=210.3.

Example 5

Synthesis of 5-chloro-1H-pyrrolo[2,3-b]pyridine 6

5-Chloro-1H-pyrrolo[2,3-b]pyridine 6 was synthesized in two steps from 5-bromo-1-triisopropylsilyl-7-azaindole 2 as shown in Scheme 2.

Scheme 2

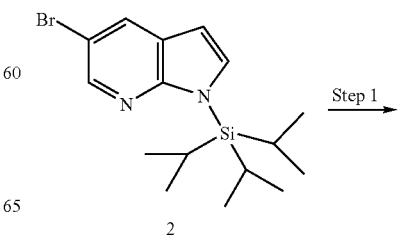

-continued

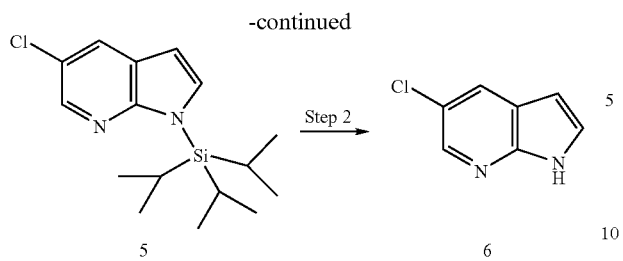

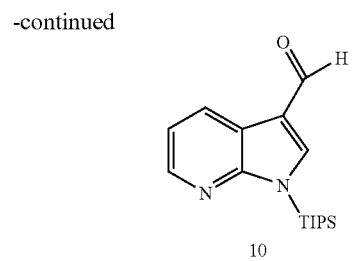

Step 1—Preparation 5-chloro-1-triisopropylsilanyl-1H-pyrrolo[2,3-b]pyridine (5)

To 5-bromo-1-triisopropylsilyl-7-azaindole (2, 1.60 g, 4.53 mmol, prepared as described in Example 4) in tetrahydrofuran (50.0 mL), under an atmosphere of nitrogen at −78° C., was added tert-butyllithium (1.70 M in hexane, 6.12 mL). The reaction was stirred for 1 hour, followed by addition of hexachloroethane (1.29 g, 5.43 mmol). The reaction was stirred for 3 hours, poured into water, and extracted with ethyl acetate. The organic layer was dried over anhydrous sodium sulfate and filtered. The filtrate was concentrated to give the crude compound (5, 1.60 g). MS (ESI)[M+H$^+$]$^+$=309.3.

Step 2—Preparation 5-chloro-1H-pyrrolo[2,3-b]pyridine (6)

To 5-chloro-1-triisopropylsilanyl-1H-pyrrolo[2,3-b]pyridine (5, 1.40 g, 4.53 mmol) in tetrahydrofuran (15 mL) was added tetra-n-butylammonium fluoride (1.42 g, 5.43 mmol). The reaction mixture was stirred at room temperature for 10 minutes. The reaction mixture was concentrated and isolated by silica gel column chromatography eluting with 30% ethyl acetate in hexane to give the compound (6, 0.40 g. 58% over 2 steps). MS (ESI)[M−H$^+$]$^-$=153.1.

5-Fluoro-1H-pyrrolo[2,3-b]pyridine 7

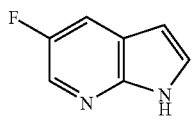

was prepared using the protocol of Scheme 2, substituting hexachloroethane with N-fluoro-N-(phenylsulfonyl)-benzenesulfonamide in Step 1. MS (ESI) [M+H$^+$]$^+$=137.1.

Example 6

Synthesis of 1-triisopropylsilanyl-1H-pyrrolo[2,3-b]pyridine-3-carbaldehyde 10

1-Triisopropylsilanyl-1H-pyrrolo[2,3-b]pyridine-3-carbaldehyde 10 was synthesized in two steps from 7-azaindole 8 as described in Scheme 3.

Scheme 3

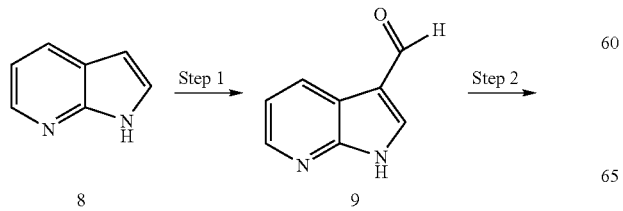

Step 1—Preparation of 1H-pyrrolo[2,3-b]pyridine-3-carbaldehyde (9)

To 1H-Pyrrolo[2,3-b]pyridine (8, 16.0 g, 135 mmol) in water (110 mL), were added hexamethylenetetramine (26.0 g, 185 mmol), and acetic acid (55.0 mL, 967 mmol). The reaction was refluxed for 12 hours. Water (329 mL) was added and the reaction was cooled to room temperature. The reaction was filtrated and washed with water to give the compound (9, 15.0 g, 76%). MS(ESI)[M+H$^+$]$^+$=147.

Step 2—Preparation of 1-triisopropylsilanyl-1H-pyrrolo[2,3-h]pyridine-3-carbaldehyde (10)

To 1H-Pyrrolo[2,3-b]pyridine-3-carbaldehyde (9, 4.05 g, 27.71 mmol) in tetrahydrofuran (30.0 mL) were added sodium hydride (60% in mineral oil, 1.5 g, 38 mmol) and triisopropylsilyl chloride (8.0 mL, 38 mmol) under an atmosphere of nitrogen. The reaction was stirred for 2 hours at room temperature. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to give the compound (10, 3.0 g, 36%). MS (ESI)[M+H$^+$]$^+$=303.

Example 7

Synthesis of 5-isopropyl-1H-pyrrolo[2,3-b]pyridine 13

5-Isopropyl-1H-pyrrolo[2,3-b]pyridine 13 was synthesized in three steps from 5-bromo-1-triisopropylsilanyl-1,1-pyrrolo[2,3-b]pyridine 2 as described in Scheme 4.

Scheme 4

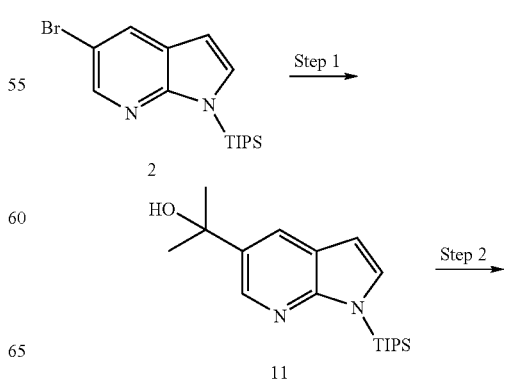

-continued

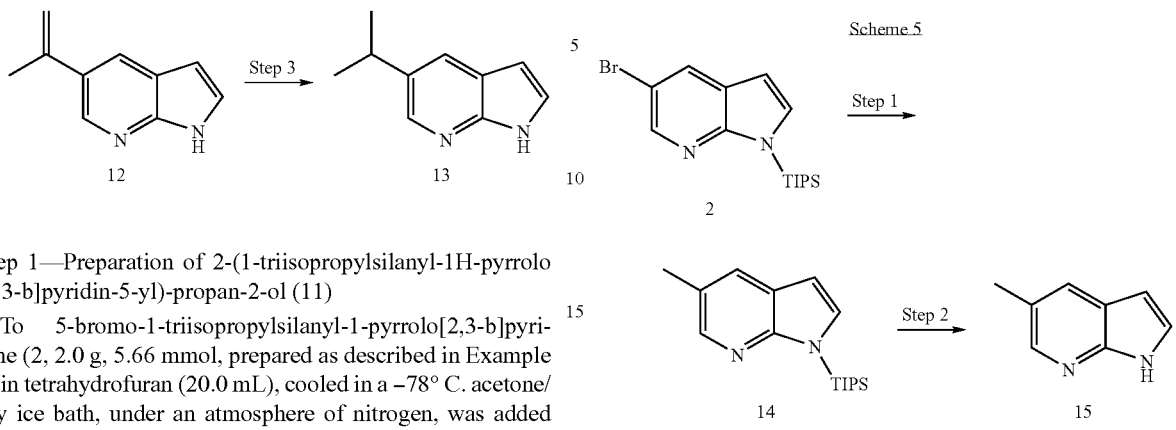

Step 1—Preparation of 2-(1-triisopropylsilanyl-1H-pyrrolo[2,3-b]pyridin-5-yl)-propan-2-ol (11)

To 5-bromo-1-triisopropylsilanyl-1-pyrrolo[2,3-b]pyridine (2, 2.0 g, 5.66 mmol, prepared as described in Example 1) in tetrahydrofuran (20.0 mL), cooled in a −78° C. acetone/dry ice bath, under an atmosphere of nitrogen, was added tert-butyllithium (1.7 M in tetrahydrofuran, 7.3 mL, 12 mmol) dropwise. After 20 minutes, acetone (0.830 mL, 11 mmol) was added dropwise to the reaction. The reaction was stirred for 30 minutes at −78° C. and then allowed to reach room temperature. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to give the compound (11, 1.30 g, 69%). MS(ESI)[M+H$^+$]$^+$=333.

Step 2—Preparation of 5-isopropenyl-1H-pyrrolo[2,3-b]pyridine (12)

To 2-(1-triisopropylsilanyl-1H-pyrrolo[2,3-b]pyridin-5-yl)-propan-2-ol (11, 0.500 g, 1.5 mmol) in acetonitrile (10.0 mL) were added triethylsilane (1.00 mL, 6.3 mmol) and trifluoroacetic acid (0.50 mL, 6.5 mmol) under an atmosphere of nitrogen. The reaction was refluxed for 3 hours, then cooled down to room temperature. The reaction was poured into water and extracted with ethyl acetate. The organic layer was washed with brine, dried over anhydrous sodium sulfate and filtered. The filtrate was concentrated and purified by silica gel column chromatography eluting with 50% ethyl acetate in hexane to give the compound (12, 0.200 g, 84%). MS(ESI)[M+H$^+$]$^+$=159.

Step 3—Preparation of 5-isopropyl-1H-pyrrolo[2,3-b]pyridine (13)

To 5-isopropenyl-1H-pyrrolo[2,3-b]pyridine (12, 0.080 g, 0.501 mmol) in tetrahydrofuran (5.0 mL) was added 20% palladium hydroxide on carbon (5.0 mg). The reaction was stirred under hydrogen at 40 psi for 30 minutes. The reaction mixture was filtered and concentrated to give the compound (13, 0.078 g, 96%). MS (ESI)[M+H$^+$]$^+$=161.

Example 8

Synthesis of 5-methyl-1H-pyrrolo[2,3-b]pyridine 15

5-Methyl-1H-pyrrolo[2,3-b]pyridine 15 was synthesized in two steps from 5-bromo-1-triisopropylsilanyl-1H-pyrrolo[2,3-b]pyridine 2 as described in Scheme 5.

Step 1—Preparation of 5-methyl-1-triisopropylsilanyl-1H-pyrrolo[2,3-b]pyridine (14)

To PdCl$_2$(dppf) (0.04 g, 0.05 mmol) in toluene (10.0 mL) under an atmosphere of nitrogen were added 5-bromo-1-triisopropylsilanyl-1H-pyrrolo[2,3-b]pyridine (2, 0.3 g, 0.8 mmol, prepared as described in Example 1, 1.0 mL in toluene) and methylmagnesium bromide (1.0 M in tetrahydrofuran, 3.0 mL, 3.0 mmol). The reaction was stirred 90° C. for 2 hours and then allowed to reach to room temperature. The reaction was poured into citric acid (0.1 M in water) and extracted with ethyl acetate. The organic layer was washed with brine, dried over anhydrous sodium sulfate and filtered. The filtrate was concentrated and purified by silica gel column chromatography eluting with 50% ethyl acetate in hexane to give the compound (14, 0.16 g, 60.0%). MS (ESI)[M+H$^+$]$^+$=289.4.

Step 2—Preparation of 5-methyl-1H-pyrrolo[2,3-b]pyridine (15)

To 5-Methyl-1-triisopropylsilanyl-1H-pyrrolo[2,3-b]pyridine (14, 0.160 g, 0.55 mmol) in tetrahydrofuran (3.0 mL) was added tetra-n-butylammonium fluoride (0.145 g, 0.55 mmol). The reaction was stirred for 1 hour at room temperature. The reaction was poured into water and extracted with ethyl acetate. The organic layer was washed with brine, dried over anhydrous sodium sulfate and filtered. The filtrate was concentrated and purified by silica gel column chromatography eluting with 3% methanol in dichloromethane to provide light yellow solid (15, 0.07 g, 95%). MS (ESI)[M+H$^+$]$^+$=133.2.

5-Methyl-1-pyrrolo[2,3-b]pyridine 16

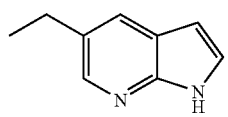

was prepared following the protocol of Scheme 5, substituting methylmagnesium bromide with ethylmagnesium bromide in Step 1.

Example 9

Synthesis of 5-methoxy-1H-pyrrolo[2,3-b]pyridine 17 and related compounds

5-Methoxy-1H-pyrrolo[2,3-b]pyridine 17 was synthesized in one step from 5-bromo-1H-pyrrolo[2,3-b]pyridine 1 as described in Scheme 6.

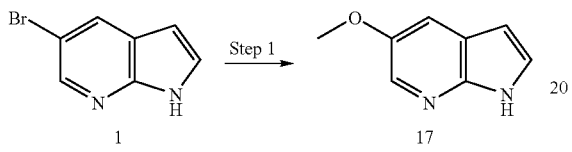

Step 1—Preparation of 5-methoxy-1H-pyrrolo[2,3-b]pyridine (17)

To 5-bromo-7-azaindole (1, 500.0 mg, 2.53 mmol) in N,N-dimethylformamide (8 mL) were added copper(I) iodide (966 mg, 5.08 mmol) and sodium methoxide in methanol (3 M, 5 mL). The reaction was stirred overnight at 120° C. under an atmosphere of Argon. The reaction was poured into water, and extracted with ethyl acetate. The organic layer was dried over anhydrous sodium sulfate, filtered. The filtrate was concentrated and purified with silica gel column chromatograph eluting with 20% ethyl acetate in hexane to give white solid (17, 140 mg, 28%). MS (ESI)[M+H$^+$]$^+$=149.1. In an alternative method, 2.3 g (11.7 mmol) 5-bromo-7-azaindole (1, 2.3 g, 11.7 mmol) was dissolved in 75 mL N,N-dimethylformamide and 50 mL methanol (50 mL), adding sodium methoxide (32 g, 0.6 mol) and copper-(1) bromide (3.2 g, 22.4 mmol) at room temperature. The reaction was stirred for three hours at 100° C. under an atmosphere of argon. The mixture was diluted with ethyl acetate and poured into a solution of ammonium chloride:ammonium hydroxide (4:1). The organic layer was extracted with ammonium chloride:ammonium hydroxide (4:1), washed with brine, dried over anhydrous sodium sulfate, filtered and concentrated. The desired compound was isolated by silica gel column chromatography eluting with 30% to 70% ethyl acetate in hexanes to give a yellow solid (17, 0.27 g, 15.6%). MS (ESI) [M+H$^+$]$^+$=149.2.

5-Ethoxy-1H-pyrrolo[2,3-b]pyridine 18

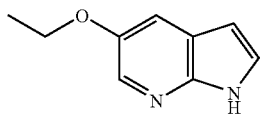

was prepared using the protocol of Scheme 6, substituting methanol with ethanol and sodium methoxide with sodium ethoxide.

5-(2-Methoxy-ethoxy)-1H-pyrrolo[2,3-b]pyridine 19

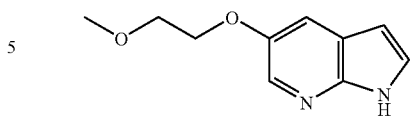

was prepared using the protocol of Scheme 6, substituting methanol with 2-methoxy-ethanol and sodium methoxide with sodium 2-methoxy-ethoxide (prepared from 2-methoxy-ethanol and sodium hydride). MS (ESI) [M+H$^+$]$^+$=193.3.

Diethyl-[2-(1H-pyrrolo[2,3-b]pyridin-5-yloxy)-ethyl]-amine 20

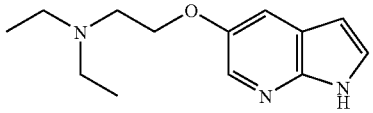

was prepared using the protocol of Scheme 6, substituting methanol with 2-diethylamino-ethanol and sodium methoxide with sodium 2-diethylamino-ethoxide (prepared from 2 2-diethylamino-ethanol and sodium hydride). MS (ESI) [M+H$^+$]$^+$=234.5.

Example 10

Synthesis of 5-pyridin-3-yl-1H-pyrrolo[2,3-b]pyridine 22

5-Pyridin-3-yl-1H-4-pyrrolo[2,3-b]pyridine 22 was synthesized in one step from 5-bromo-1H-pyrrolo[2,3-b]pyridine 1 as described in Scheme 7

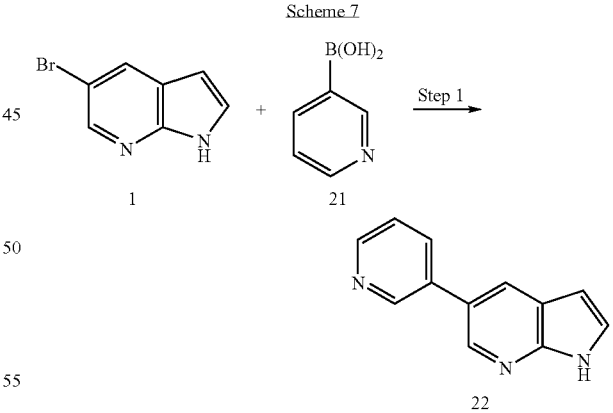

Step 1—Preparation of 5-pyridin-3-yl-1H-pyrrolo[1,3-b]pyridine (22)

To 5-bromo-7-azaindole (1, 1.00 g, 5.08 mmol) in water (13.0 mL) and acetonitrile (36 mL) were added pyridine-3-boronic acid (21, 1.0 g, 8.1 mmol), potassium carbonate (1.79 g, 0.0130 mol) and Tetrakis(triphenylphosphine)palladium (0) (50.0 mg, 0.043 mmol) under an atmosphere of nitrogen. The reaction mixture was heated to 170° C. overnight. The reaction mixture was poured into water and extracted with ethyl acetate. The organic layer was washed with brine, dried over sodium sulfate, and concentrated. The residue was purified with silica gel column chromatography eluting with 25% ethyl acetate in hexane to provide a light yellow solid (22, 820 mg, 82%). MS (ESI)[M+H$^+$]$^+$=196.1.

Additional compounds were prepared following the protocol of Scheme 7, either by substituting pyridine-3-boronic acid with an appropriate boronic acid or by substituting the 5-bromo-7-azaindole with 5-(4,4,5,5-Tetramethyl-[1,3,2]dioxaborolan-2-yl)-1H-pyrrolo[2,3-b]pyridine and reacting with a suitable aryl or heteroaryl halide (i.e. coupling with the boronic acid ester on the azaindole, and the halide on the group to be coupled to the 5-position of the azaindole). The following compounds were prepared by this procedure:

5-(4-Chloro-phenyl)-1H-pyrrolo[2,3-b]pyridine (23),
5-(4-Fluoro-phenyl)-1H-pyrrolo[2,3-b]pyridine (24),
5-Phenyl-1H-pyrrolo[2,3-b]pyridine (25),
5-(6-Methoxy-pyridin-3-yl)-1-pyrrolo[2,3-b]pyridine (26),
5-(2-Methoxy-pyrimidin-5-yl)-1H-pyrrolo[2,3-b]pyridine (27),
5-Pyridin-4-yl-1H-pyrrolo[2,3-b]pyridine (28),
4-(1H-pyrrolo[2,3-b]pyridin-5-yl)-benzenesulfonamide (29),
3-(1H-pyrrolo[2,3-b]pyridin-5-yl)-benzenesulfonamide (30),
5-Pyrimidin-5-yl-1H-pyrrolo[2,3-b]pyridine (31),
5-(3-Methanesulfonyl-phenyl)-1H-pyrrolo[2,3-b]pyridine (32),
3-(1H-Pyrrolo[2,3-b]pyridin-5-yl)-benzamide (33),
5-(5-Methyl-1H-imidazol-2-yl)-1H-pyrrolo[2,3-b]pyridine (34),
5-(1-Methyl-1H-imidazol-2-yl)-1H-pyrrolo[2,3-b]pyridine (35), and
5-(1,5-Dimethyl-1H-imidazol-2-yl)-1H-pyrrolo[2,3-b]pyridine (59).

The following table indicates either 5-bromo-7-azaindole or 5-(4,4,5,5-Tetramethyl-[1,3,2]dioxaborolan-2-yl)-1H-pyrrolo[2,3-b]pyridine starting material (column 1) and the appropriate reagent to be coupled to the 5 position of the azaindole (column 2) to afford the resulting compound (column 3), with the observed mass given in column 4.

| Starting azaindole | Reagent coupled to 5 position | Compound | MS(ESI) [M + H$^+$]$^+$ observed |
|---|---|---|---|
| 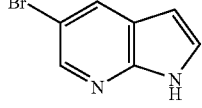 | 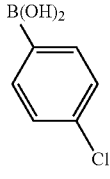 | 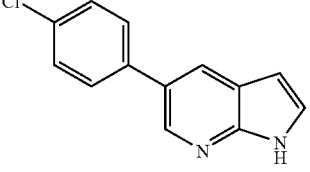 | 229.1 |
| 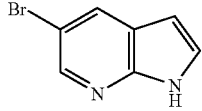 | 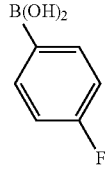 | 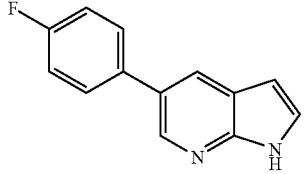 | 213.1 |
| 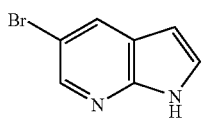 | 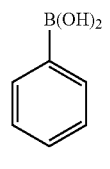 | 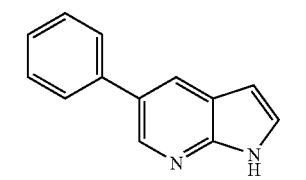 | 195.2 |
| 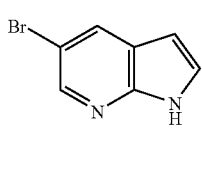 | 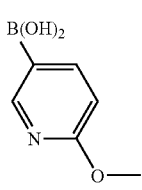 | 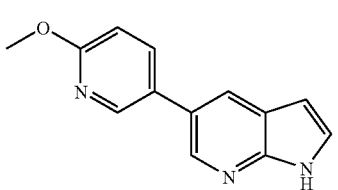 | 226.2 |
| 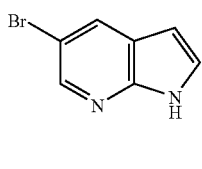 | 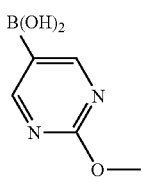 | 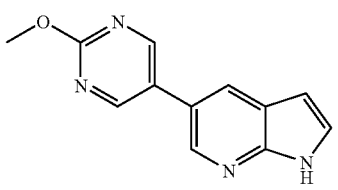 | 227.2 |

-continued

| Starting azaindole | Reagent coupled to 5 position | Compound | MS(ESI) [M + H+]+ observed |
|---|---|---|---|
| 7-azaindole-5-boronic acid pinacol ester | 4-iodopyridine | 5-(pyridin-4-yl)-7-azaindole | 196.2 |
| 7-azaindole-5-boronic acid pinacol ester | 4-bromobenzenesulfonamide | 4-(7-azaindol-5-yl)benzenesulfonamide | 274.1 |
| 7-azaindole-5-boronic acid pinacol ester | 3-bromobenzenesulfonamide | 3-(7-azaindol-5-yl)benzenesulfonamide | 274.1 |
| 7-azaindole-5-boronic acid pinacol ester | 5-bromopyrimidine | 5-(pyrimidin-5-yl)-7-azaindole | 197.2 |
| 5-bromo-7-azaindole | 3-(methylsulfonyl)phenylboronic acid | 5-(3-(methylsulfonyl)phenyl)-7-azaindole | 273.1 |
| 5-bromo-7-azaindole | 3-carbamoylphenylboronic acid | 3-(7-azaindol-5-yl)benzamide | 238.2 |
| 7-azaindole-5-boronic acid pinacol ester | 2-bromo-4-methylimidazole | 5-(4-methyl-1H-imidazol-2-yl)-7-azaindole | 199.2 |
| 7-azaindole-5-boronic acid pinacol ester | 2-bromo-1-methylimidazole | 5-(1-methyl-1H-imidazol-2-yl)-7-azaindole | 199.2 |

-continued

| Starting azaindole | Reagent coupled to 5 position | Compound | MS(ESI) [M + H+]+ observed |
|---|---|---|---|
| 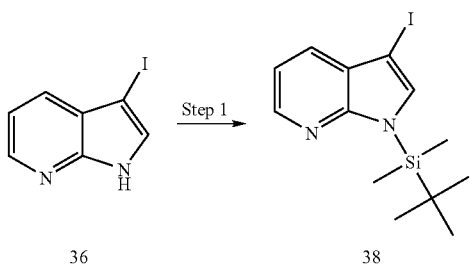 | | | 213.2 |

Example 11

Synthesis of 3-Iodo-1-triisopropylsilanyl-1-pyrrolo[2,3-b]pyridine 37

3-Iodo-1-triisopropylsilanyl-1H-pyrrolo[2,3-b]pyridine 37 was synthesized in one step from 3-Iodo-1H-pyrrolo[2,3-b]pyridine 36 as shown in Scheme 8.

Scheme 8

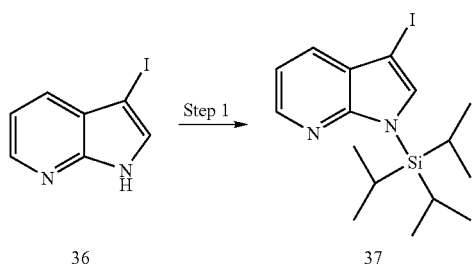

Step 1—Preparation of 3-Iodo-1-triisopropylsilanyl-1H-pyrrolo[1,3-b]pyridine (37)

3-Iodo-1H-pyrrolo[2,3-b]pyridine 36 (2.00 g, 8.20 mmol) was dissolved in N,N-dimethylformamide (50 mL). Sodium hydride (60% dispersion in mineral oil, 390 mg, 9.8 mmol) was added. After 20 minutes, triisopropylsilyl chloride (1.74 mL, 8.20 mmol) was added dropwise. After 1.5 hours, the reaction was poured into water and extracted with ethyl acetate, washed with saturated sodium bicarbonate and brine. The organic portions were dried over anhydrous sodium sulfate and concentrated. Purification by silica gel chromatography, 0-25% gradient ethyl acetate hexane gave compound 37 as a white solid (3.224 g, 98.2%). $^1$H-NMR was consistent with the desired compound.

Example 12

Synthesis of 1-(tert-Butyl-dimethyl-silanyl)-3-iodo-1H-pyrrolo[2,3-b]pyridine 38

1-(tert-Butyl-dimethyl-silanyl)-3-iodo-1H-pyrrolo[2,3-b]pyridine 38 was synthesized in one step from 3-Iodo-1H-pyrrolo[2,3-b]pyridine 36 as shown in Scheme 9.

Scheme 9

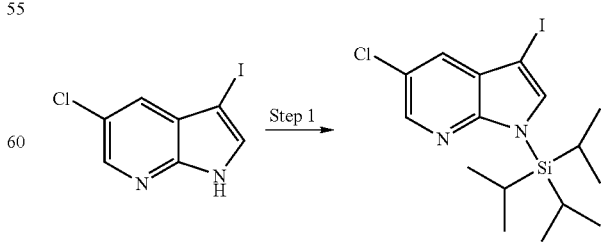

Step 1—Preparation of 1-(tert-Butyl-dimethyl-silanyl)-3-iodo-1H-pyrrolo[2,3-b]pyridine (38)

3-Iodo-1H-pyrrolo[2,3-b]pyridine 36 (1.11 g, 4.6 mmol) was dissolved in tetrahydrofuran (120 mL). Sodium hydride (60% dispersion in mineral oil, 0.13 g, 5.5 mmol) was added, followed by tert-butyldimethylsilyl chloride (0.85 g, 5.5 mmol). The reaction was stirred at room temperature overnight. The reaction was poured into water and extracted with ethyl acetate. The organic portion was washed with brine, dried over anhydrous sodium sulfate and filtered. The filtrate was concentrated and purified with silica gel column chromatography eluting with 30% ethyl acetate in hexane to give the compound as a white solid (38, 100 mg, 15%).

Example 13

Synthesis of 5-chloro-3-iodo-1-triisopropylsilanyl-1H-pyrrolo[2,3-b]pyridine 40

5-Chloro-3-iodo-1-triisopropylsilanyl-1H-pyrrolo[2,3-b]pyridine 40 was synthesized in one step from 5-Chloro-3-iodo-1H-pyrrolo[2,3-b]pyridine 39 as shown in Scheme 10.

Scheme 10

Step 1 Preparation of 5-Chloro-3-iodo-1-triisopropylsilanyl-1H-pyrrolo[2,3-b]pyridine (40)

5-Chloro-3-iodo-1H-pyrrolo[2,3-b]pyridine (39, 31.2 g, 0.112 mmol) was dissolved in N-methylpyrolidinone (800 mL) and NaH (60% dispersion, 4.93 g, 0.123 mol) was added at room temperature. The resulting mixture was stirred for 30 minutes. To this mixture was then added triisopropylsilylchloride (24.0 mL, 0.112 mol) and the resulting mixture was stirred for 2 hours. The reaction was quenched with water and extracted with ethyl acetate three times, washed by brine, dried, filtered, and concentrated in vacuo. The residue was subjected to silica gel flash chromatography (eluted by heptane to 5% ethyl acetate/heptane) to afford the desired compound (43 g, 88%) as a pale-yellow solid.

Example 14

Synthesis of 5-[4-(2-methoxyethoxy)-phenyl]-1H-pyrrolo[2,3-b]pyridine 44

5-[4-(2-Methoxyethoxy)-phenyl]-1H-pyrrolo[2,3-b]pyridine 44 was synthesized in two steps from 4-bromophenol 41 as shown in Scheme 11.

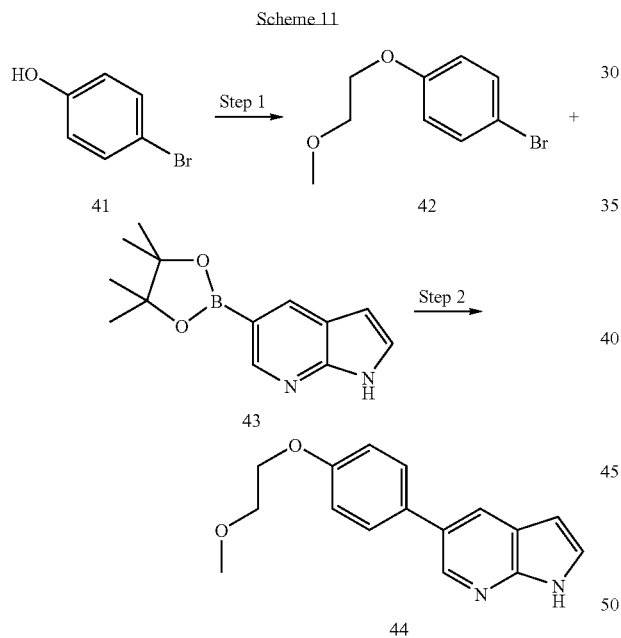

Step 1—Preparation 1-Bromo-4-(2-methoxy-ethoxy)-benzene (42)

To a solution of 4-bromophenol (41, 5.0 g, 28.9 mmol) in dimethylformamide (15 mL) were added potassium carbonate (4.40 g, 31.8 mmol) and 1-bromo-2-methoxyethane (5.00 g, 36.0 mmol) under an atmosphere of nitrogen. The reaction mixture was stirred at ambient temperature overnight and concentrated under reduced pressure. The residue was slurried in ethyl acetate (50 mL) and filtered. The filtrate was washed with saturated sodium bicarbonate solution, dried over magnesium sulfate and filtered. Silica gel column chromatography (0-10% ethyl acetate in hexanes) gave the desired compound as a colorless oil (42, 3.2 g, 48%).

Step 2—Preparation of 5-[4-(2-Methoxy-ethoxy)-phenyl]-1H-pyrrolo[2,3-b]pyridine (44)

To a solution of 5-(4,4,5,5,-tetramethyl-[1,3,2]dioxaborolan-2-yl)-1H-pyrrolo[2,3-b]pyridine (43, 1.1 g, 4.3 mmol) in tetrahydrofuran (40 mL) was added 1-bromo-4-(2-methoxyethoxy)-benzene (42, 1.50 g, 6.49 mmol) and tetrakis(triphenylphosphine)palladium (0) (0.25 g, 0.21 mmol). The reaction mixture was stirred with potassium carbonate solution (10 mL, 1.04M) and warmed to reflux overnight. The biphasic reaction mixture was diluted with ethyl acetate (50 mL) and saturated sodium carbonate solution (20 mL). The organic layer was separated, washed with brine, dried over magnesium sulfate and purified by silica gel column chromatography (50-100 ethyl acetate in hexanes) to give the desired compound as a colorless solid (44, 782 mg, 67%). MS (ESI) $[M+H^+]^+=267.4$.

Example 15

Synthesis of 5-(1-methyl-1H-pyrazol-4-yl)-1H-pyrrolo[2,3-b]pyridine 46

5-(1-Methyl-1H-pyrazol-4-yl)-1H-pyrrolo[2,3-b]pyridine 46 was synthesized in one step from 5-bromo-1H-pyrrolo[2,3-b]pyridine 1 as shown in Scheme 12.

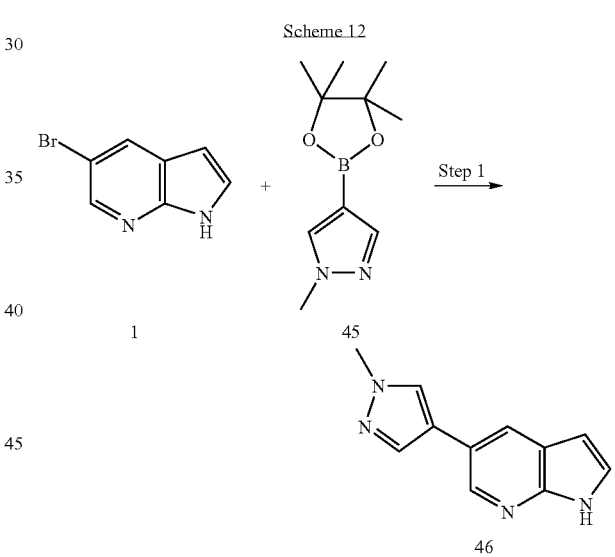

Step 1—Preparation of 5-(1-Methyl-1H-pyrazol-4-yl)-1H-pyrrolo[2,3-b]pyridine (46)

To 5-bromo-7-azaindole (1, 1.04 g, 5.28 mmol) in 1.00 M potassium carbonate in water (15.8 mL) and tetrahydrofuran (50.0 mL) were added 1-methyl-4-(4,4,5,5-tetramethyl-[1,3,2]dioxaborolan-2-yl)-1H-pyrazole (45, 1.65 g, 7.92 mmol), Tetrakis(triphenylphosphine)-palladium(0) (0.305 mg, 0.26 mmol) and tetra-n-butylammonium iodide (0.20 g, 0.53 mmol). The reaction mixture was stirred at 70° C. overnight. The reaction mixture was poured into water and the organic layer was washed with brine, dried over sodium sulfate, and concentrated. The residue was purified with silica gel column chromatography eluting with 25% ethyl acetate in hexane to provide a light yellow solid (46, 670 mg, 64.0%). MS (ESI) $[M+H^+]^+=199.4$.

Example 16

Preparation of propane-2-sulfonic acid [2,4-difluoro-3-(5-pyridin-3-yl-1H-pyrrolo[2,3-b]pyridine-3-carbonyl)-phenyl]-amide 51

Propane-2-sulfonic acid [2,4-difluoro-3-(5-pyridin-3-yl-1H-pyrrolo[2,3-b]pyridine-3-carbonyl)-phenyl]-amide 51 was synthesized in four steps from 2,4-difluorophenylamine 47 as shown in Scheme 13.

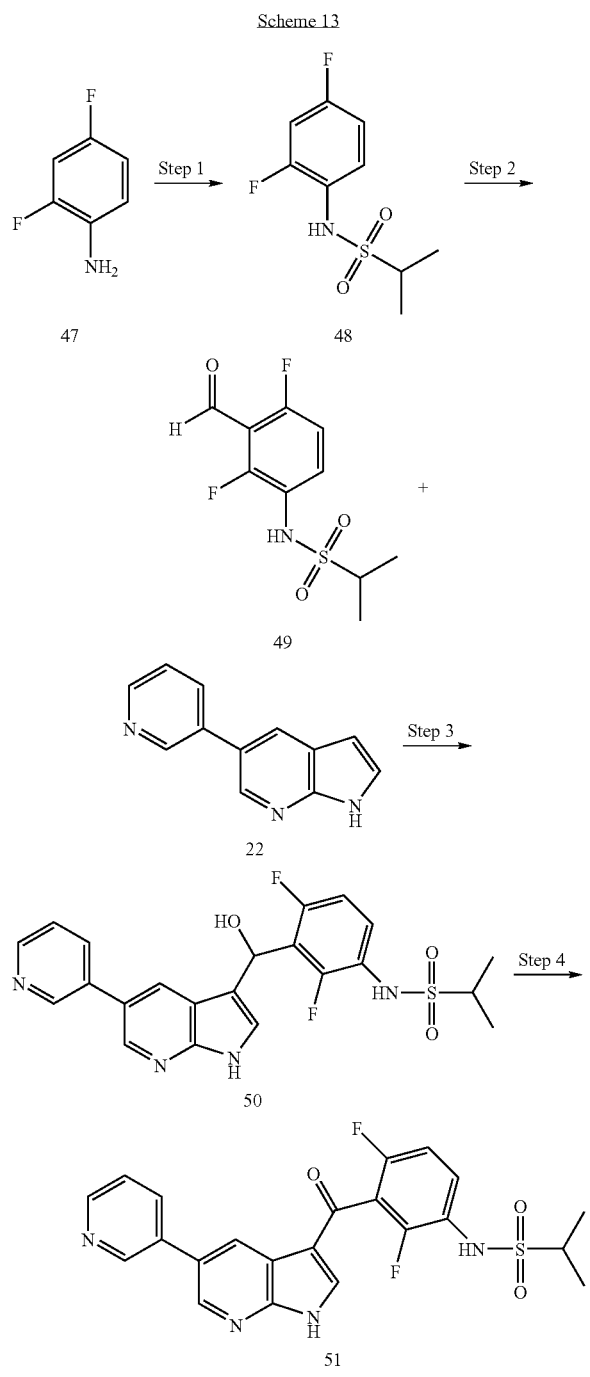

Step 1—Preparation of propane-2-sulfonic acid (2,4-difluoro-phenyl)-amide (48)

To 2,4-difluoro-phenylamine (47, 4.0 mL, 40.0 mmol) in dichloromethane (50 mL) were added pyridine (3.37 mL, 42.3 mmol), propane-2-sulfonyl chloride (6.00 g, 42.3 mmol) and dimethylaminopyridine (0.20 g, 1.64 mmol) under an atmosphere of nitrogen. The reaction was stirred at 45° C. overnight. The reaction was poured into water and extracted with ethyl acetate. The organic layer was washed with brine, dried over anhydrous sodium sulfate and filtered. The filtrate was concentrated and purified by silica gel column chromatography 3% methanol in methylene chloride to give a white solid (48, 8.0 g, 85%). MS (ESI) $[M-H^+]^+=234.0$.

Step 2-Preparation of propane-2-sulfonic acid (2,4-difluoro-3-formyl-phenyl)-amide (49)

To propane-2-sulfonic acid (2,4-difluoro-phenyl)-amide (48, 2.35 g, 9.95 mmol) in tetrahydrofuran (70 mL) under an atmosphere of nitrogen cooled with a dry ice/acetone bath was added 1.60 M of n-butyllithium (1.60 M in hexane, 6.53 mL, 10.45 mmol). The reaction was stirred for 40 minutes, and then another portion of n-butyllithium (1.60 M in hexane, 6.84 mL, 10.94 mmol). The reaction was stirred for 1 hour and N,N-dimethylformamide (0.92 mL, 11.9 mmol) was added. The reaction was allowed to warm to room temperature overnight. The reaction was poured into water extracted with ethyl acetate. The organic layer was washed with brine, dried over anhydrous sodium sulfate and filtrated. The filtrate was concentrated and purified by silica gel column chromatography (dichloromethane/methanol 5%) to give the compound (49, 1.4 g, 53.4%). MS (ESI) $[M-H^+]^-=263.4$.

Step 3—Preparation of propane-2-sulfonic acid {2,4-difluoro-3-[hydroxy-(5-pyridin-3-yl-1H-pyrrolo[2,3-b]pyridin-3-yl)-methyl]-phenyl}-amide (50)

To propane-2-sulfonic acid (2,4-difluoro-3-formyl-phenyl)-amide (49, 220.0 mg, 0.83 mmol) in methanol (15 mL) was added 5-pyridin-3-yl-1H-1-pyrrolo[2,3-b]pyridine (22, 150.0 mg, 0.77 mmol, prepared as described in Example 10) and potassium hydroxide (537.0 mg, 9.6 mmol) under an atmosphere of nitrogen. The reaction was stirred at room temperature overnight. The reaction was poured into water and extracted with ethyl acetate. The organic layer was washed with brine, dried over sodium sulfate and filtrated. The filtrate was concentrated and purified by silica gel column chromatography eluting with 5% methanol in dichloromethane to give the compound (50, 160 mg, 45.3%). In this step, minor compound propane-2-sulfonic acid {2,4-difluoro-3-[methoxy-(5-pyridin-3-yl-1H-pyrrolo[2,3-b]pyridin-3-yl)-methyl]-phenyl}-amide was also formed and isolated. MS(ESI) $[M+H^+]^+=460.1$.

Step 4—Preparation of propane-2-sulfonic acid [2,4-difluoro-3-(5-pyridin-3-yl-1H-pyrrolo[2,3-b]pyridine-3-carbonyl)-phenyl]-amide (51)

To propane-2-sulfonic acid {2,4-difluoro-3-[hydroxy-(5-pyridin-3-yl-1H-pyrrolo[2,3-b]pyridin-3-yl)-methyl]-phenyl}-amide (50, 40.0 mg, 0.087 mmol) in tetrahydrofuran (10 mL) was added Dess-Martin periodane (48.0 mg, 0.11 mmol). The reaction was stirred at room temperature for 5 minutes. The reaction was poured into sodium thiosulfate and potassium carbonate solution and extracted with ethyl acetate. The organic layer was washed with brine, dried over anhydrous sodium sulfate and filtrated. The filtrate was concentrated and purified by silica gel column chromatography eluting with 5% methanol in methylene chloride to give the compound (51, 13.4 mg, 33.5%). MS (ESI) $[M+H^+]^+=458.1$.

N-{2,4-Difluoro-3-[5-(2-methoxy-ethoxy)-1H-pyrrolo[2,3-b]pyridine-3-carbonyl]-phenyl}-4-isopropyl-benzenesulfonamide P-0018

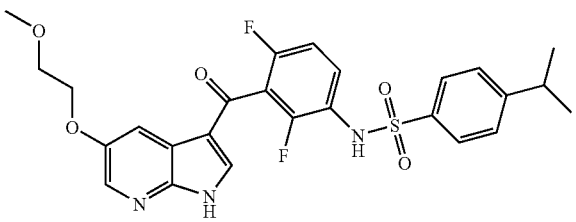

was prepared following the protocol of Scheme 13, substituting propane-2-sulfonyl chloride with 4-isopropyl-phenyl sulfonyl chloride in step 1 and 5-pyridin-3-yl-1H-pyrrolo[2,3-b]pyridine 22 with 5-(2-methoxy-ethoxy)-1H-pyrrolo[2,3-b]pyridine 19 (see Example 9) in step 3. MS (ESI) [M−H$^+$]$^−$=530.

N-{2,4-Difluoro-3-[5-(4-methyl-1H-imidazol-2-yl)-1H-pyrrolo[2,3-b]pyridine-3-carbonyl]-phenyl}-4-isopropyl-benzenesulfonamide P-0019

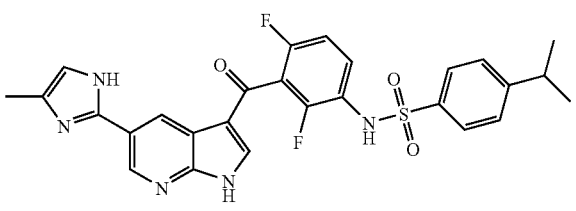

was prepared following the protocol of Scheme 13, substituting propane-2-sulfonyl chloride with 4-isopropyl-phenyl sulfonyl chloride in Step 1 and 5-pyridin-3-yl-1H-pyrrolo[2,3-b]pyridine 22 with 5-(5-methyl-1,4-imidazol-2-yl)-1H-pyrrolo[2,3-b]pyridine 34 (see Example 10) in step 3. MS (ESI) [M−H$^+$]$^−$=536.

N-{2,4-Difluoro-3-[5-(5-methyl-1H-pyrazol-4-yl)-1H-pyrrolo[2,3-b]pyridine-3-carbonyl]-phenyl}-4-isopropyl-benzenesulfonamide P-0022

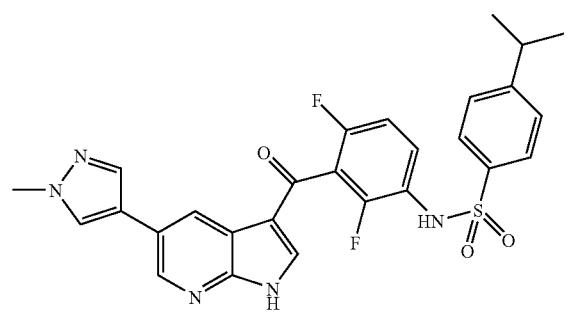

was prepared following the protocol of Scheme 13, substituting propane-2-sulfonyl chloride with 4-isopropyl-phenyl sulfonyl chloride in Step 1 and 5-pyridin-3-yl-1H-pyrrolo[2,3-b]pyridine 22 with 5-(1-methyl-1H-pyrazol-4-yl)-1H-pyrrolo[2,3-b]pyridine 46 (see Example 15) in step 3. MS (ESI) [M−H$^+$]$^−$=536.

N-{2,4-Difluoro-3-[5-(5-methyl-1H-imidazol-2-yl)-1H-pyrrolo[2,3-b]pyridine-3-carbonyl]-phenyl}-4-trifluoromethyl-benzenesulfonamide P-0025

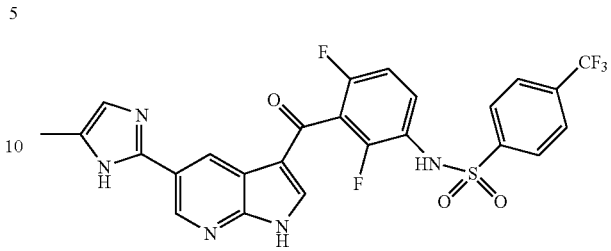

was prepared following the protocol of Scheme 13, substituting propane-2-sulfonyl chloride with 4-trifluoromethyl-phenyl sulfonyl chloride in Step 1 and 5-pyridin-3-yl-1H-pyrrolo[2,3-b]pyridine 22 with 5-(5-methyl-1H-imidazol-2-yl)-1H-pyrrolo[2,3-b]pyridine 34 (see Example 10). MS(ESI) [M−H$^+$]$^−$=562.

N-{2,4-Difluoro-3-[5-(1-methyl-T1H-imidazol-2-yl)-1H-pyrrolo[2,3-b]pyridine-3-carbonyl]-phenyl}-4-propyl-benzenesulfonamide P-0026

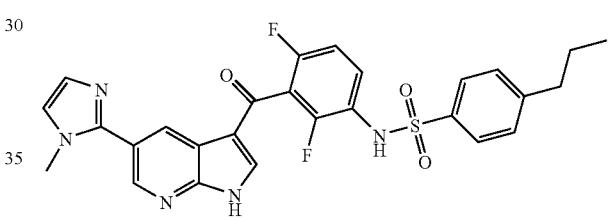

was prepared following the protocol of Scheme 13, substituting propane-2-sulfonyl chloride with propane sulfonyl chloride in Step 1 and 5-pyridin-3-yl-1H-pyrrolo[2,3-b]pyridine 22 with 5-(5-methyl-1H-imidazol-2-yl)-1H-pyrrolo[2,3-b]pyridine 35 (see Example 10) MS(ESI) [M−H$^+$]$^+$=536.2.

N-{3-[5-(1,5-Dimethyl-1H-imidazol-2-yl)-1H-pyrrolo[2,3-b]pyridine-3-carbonyl]-2,4-difluoro-phenyl}-4-propyl-benzenesulfonamide P-0027

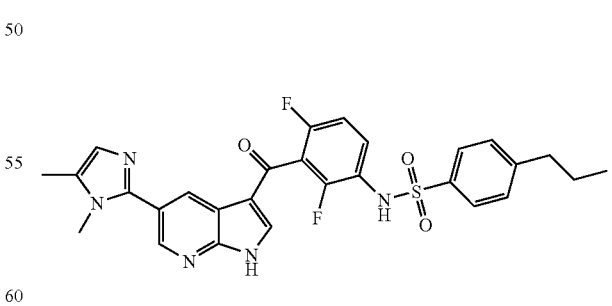

was prepared following the protocol of Scheme 13, substituting propane-2-sulfonyl chloride with propane sulfonyl chloride in Step 1 and 5-pyridin-3-yl-1H-pyrrolo[2,3-b]pyridine 22 with 5-(1,5-dimethyl-1H-imidazol-2-yl)-1H-pyrrolo[2,3-b]pyridine (59) (see Example 10). MS (ESI) [M−H$^+$]$^−$=550.1

Example 17

Synthesis of N-[3-(5-chloro-1H-pyrrolo[2,3-b]pyridine-3-carbonyl)-2,4-difluoro-phenyl]-3,5-difluorobenzenesulfonamide 58

Compound P-1841 was synthesized in six steps from 2,4-difluoroaniline 47 as shown in Scheme 14.

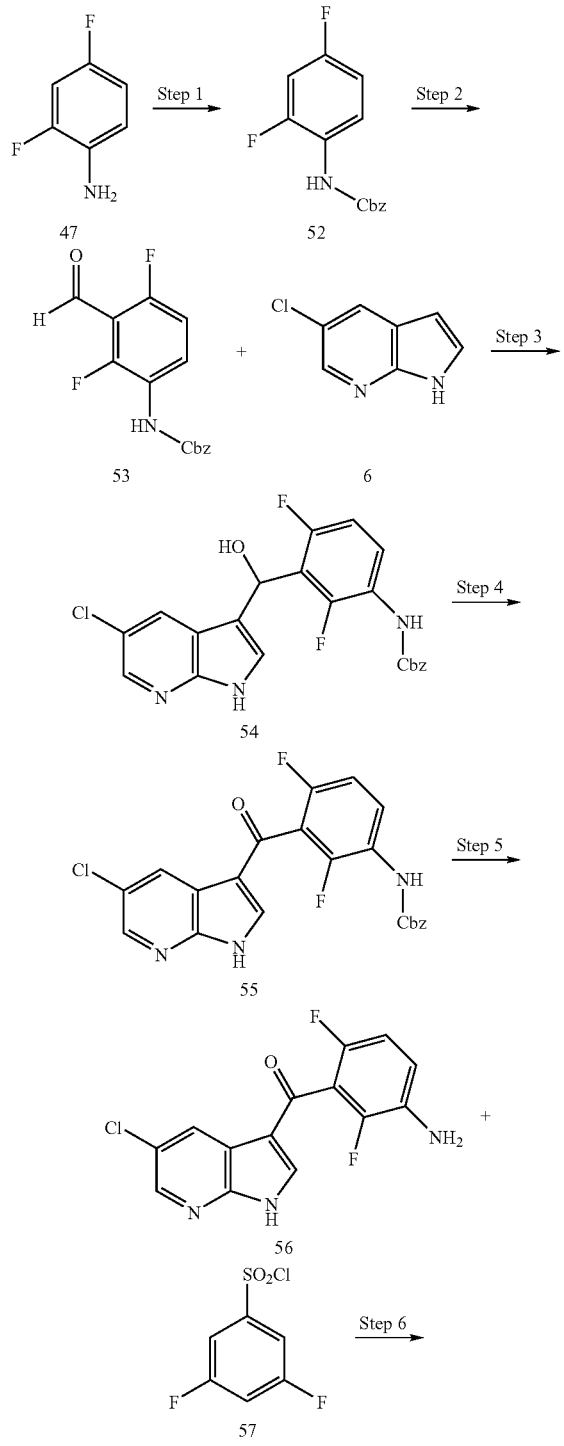

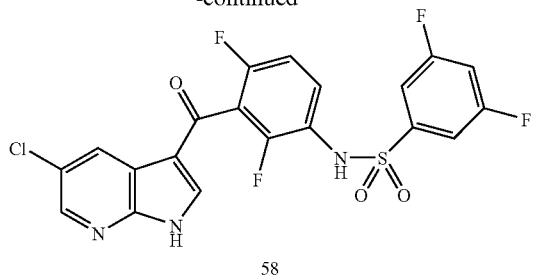

Step 1—Preparation of (2,4-difluoro-phenyl)-carbamic acid benzyl ester (52)

To 2,4-difluoroaniline (47, 7.0 mL, 0.070 mol) in 100 mL of dichloromethane was added pyridine (11 mL, 0.14 mol) and benzyl chloroformate (11.9 mL, 0.0834 mol). The reaction mixture was stirred at ambient temperature for 1.5 hours. The reaction mixture was concentrated under reduced pressure and the residue was partitioned between ethyl acetate and KHSO$_4$ solution. The organic layer was dried (MgSO$_4$), concentrated and crystallized from hexanes to give compound 52 (15.6 g, 85%).

Step 2—Preparation of (2,4-difluoro-3-formyl-phenyl)-carbamic acid benzyl ester (53)

Into a round bottom flask was added (2,4-difluoro-phenyl)-carbamic acid benzyl ester (52, 3.83 g, 14.5 mmol) in tetrahydrofuran (148 ml, 1.82 mol). The solution was chilled to 78° C. and n-butyllithium (1.60 M in hexane, 19.1 mL, 30.0 mmol) was added over 30 minutes followed by the addition of, N,N-dimethylformamide (1.12 mL, 14.5 mol). The reaction mixture was allowed to warm to ambient temperature and was stirred overnight. The reaction mixture was poured into water and extracted with ethyl acetate. The organic layer was washed with brine, dried over sodium sulfate, concentrated and crystallized from ether to give compound 53 (3.0 g, 71%).

Step 3—Preparation of {2,4-difluoro-3-[hydroxy-(1H-pyrrolo[2,3-b]pyridin-3-yl)-methyl]-phenyl}-carbamic acid benzyl ester (54)

Into a round bottom flask was added 5-chloro-1-pyrrolo[2,3-b]pyridine (6, 0.524 g, 3.43 mmol, prepared as described in Example 5) in methanol (5.00 mL, 0.123 mol). Potassium hydroxide (0.800 g, 14.2 mmol) and (2,4-difluoro-3-formyl-phenyl)-carbamic acid benzyl ester (53, 1.02 g, 3.5 mmol) were added and the reaction mixture was stirred overnight. The reaction mixture was poured into 1N HCl and extracted with ethyl acetate. The organic layer was washed with brine, dried over sodium sulfate, concentrated and crystallized from ethyl acetate to give compound 54 (710 mg, 46%). MS (ESI) [M+H$^+$]$^+$=444.

Step 4—Preparation of [2,4-difluoro-3-(1H-pyrrolo[2,3-b]pyridine-3-carbonyl)-phenyl]-carbamic acid benzyl ester (55)

Into a round bottom flask was added {2,4-difluoro-3-[hydroxy-(1H-pyrrolo[2,3-b]pyridin-3-yl)-methyl]-phenyl}-carbamic acid benzyl ester (54, 1.01 g, 2.28 mmol) in tetrahydrofuran (5.00 mL, 0.0616 mol). Dess-Martin periodinane (1.20 g, 2.89 mmol) was added in portions. The reaction mixture was stirred at ambient temperature for 10 minutes, then poured into water and extracted with ethyl acetate. The organic layer was washed with brine, dried over sodium sulfate, concentrated and purified by silica gel chromatography to give compound 55 (914 mg, 91%). MS (ESI) $[M+H^+]^+$=442.

Step 5—Preparation of (3-Amino-2,6-difluoro-phenyl)-(5-chloro-1H-pyrrolo[2, 3-b]pyridin-3-yl)-methanone (56)

[2,4-difluoro-3-(1H-pyrrolo[2,3-b]pyridine-3-carbonyl)-phenyl]-carbamic acid benzyl ester (55, 800 mg, 1.81 mmol) was added to 10 M NaOH (15.00 mL) and warmed to reflux overnight. The reaction mixture was diluted with 30 mL of water and was extracted with ethyl acetate to give compound 56 (450 mg, 81%).

Step 6—Preparation of N-[3-(5-chloro-1H-pyrrolo[2,3-b]pyridine-3-carbonyl)-2,4-difluoro-phenyl]-3,5-difluorobenzenesulfonamide (58)

Into a microwave reaction vessel were combined (3-amino-2,6-difluoro-phenyl)-(5-chloro-1H-pyrrolo[2,3-b]pyridin-3-yl)-methanone (56, 50 mg, 0.16 mmol), 3,5-difluorobenzenesulfonyl chloride (57, 103 mg, 0.49 mmol), pyridine (0.5 mL, 6.1820 mol) and tetrahydrofuran (3.0 mL). The reaction was warmed in the CEM microwave at 300 watts, 130° C. for 10 minutes. The reaction mixture was partitioned between ethyl acetate and brine. The organic layer was collected, dried over $Na_2SO_4$, filtered and concentrated. The compound (58) was isolated using column chromatography (silica, hexane:ethyl acetate 70:30) to obtain 36 mg (46%) compound. MS=482.0.

Additional compounds were prepared following the protocol of Scheme 14, optionally substituting 5-chloro-1H-pyrrolo[2,3-b]pyridine 6 with an appropriate azaindole (see Examples 5, 10 or 15) in Step 3 and/or 3,5-difluorobenzenesulfonyl chloride 57 with an appropriate sulfonyl chloride in Step 6. The following compounds were prepared by this procedure.

Benzo[b]thiophene-3-sulfonic acid [3-(5-chloro-1H-pyrrolo[2,3-b]pyridine-3-carbonyl)-2,4-difluoro-phenyl]-amide (P-0001), 5-Methyl-2-trifluoromethyl-furan-3-sulfonic acid [3-(5-chloro-1H-pyrrolo[2,3-b]pyridine-3-carbonyl)-2,4-difluoro-phenyl]-amide (P-0002), 5-Oxazol-5-yl-thiophene-2-sulfonic acid [3-(5-chloro-1H-pyrrolo[2,3-b]pyridine-3-carbonyl)-2,4-difluoro-phenyl]-amide (P-0003), 3-[3-(5-Chloro-1H-pyrrolo[2,3-b]pyridine-3-carbonyl)-2,4-difluoro-phenylsulfamoyl]-benzoic acid (P-0004), 2-Oxo-2H-chromene-6-sulfonic acid [3-(5-chloro-1H-pyrrolo[2,3-b]pyridine-3-carbonyl)-2,4-difluoro-phenyl]-amide (P-0005), 5-Isoxazol-5-yl-thiophene-2-sulfonic acid [3-(5-chloro-1H-pyrrolo[2,3-b]pyridine-3-carbonyl)-2,4-difluoro-phenyl]-amide (P-0006), 4-Butoxy-N-[3-(5-chloro-1H-pyrrolo[2,3-b]pyridine-3-carbonyl)-2,4-difluoro-phenyl]-benzenesulfonamide (P-0007), N-[3-(5-Chloro-1H-pyrrolo[2,3-b]pyridine-3-carbonyl)-2,4-difluoro-phenyl]-4-pyrazol-1-yl-benzenesulfonamide (P-0008)

Benzothiazole-6-sulfonic acid [3-(5-chloro-1H-pyrrolo[2,3-b]pyridine-3-carbonyl)-2,4-difluoro-phenyl]-amide (P-0009), 1-Methyl-3-trifluoromethyl-1H-pyrazole-4-sulfonic acid [3-(5-chloro-1H-pyrrolo[2,3-b]pyridine-3-carbonyl)-2,4-difluoro-phenyl]-amide (P-0010), N-[3-(5-Chloro-1H-pyrrolo[2,3-b]pyridine-3-carbonyl)-2,4-difluoro-phenyl]-4-isopropoxy-benzenesulfonamide (P-0011), Benzo[1,2,5]thiadiazoe-5-sulfonic acid [3-(5-chloro-1H-pyrrolo[2,3-b]pyridine-3-carbonyl)-2,4-difluoro-phenyl]-amide (P-00133), 4-tert-Butyl-N-[3-(5-chloro-1H-pyrrolo[2,3-b]pyridine-3-carbonyl)-2,4-difluoro-phenyl]-benzenesulfonamide (P-0014), N-[3-(5-Chloro-1H-pyrrolo[2,3-b]pyridine-3-carbonyl)-2,4-difluoro-phenyl]-4-propyl-benzenesulfonamide (P-0015), N-[3-(5-Chloro-1H-pyrrolo[2,3-b]pyridine-3-carbonyl)-2,4-difluoro-phenyl]-3-difluoromethoxy-benzenesulfonamide (P-0016), 5-Methyl-benzo[b]thiophene-2-sulfonic acid [3-(5-chloro-1H-pyrrolo[2,3-b]pyridine-3-carbonyl)-2,4-difluoro-phenyl]-amide (P-0017), 3-Difluoromethoxy-N-{2,4-difluoro-3-[5-(1-methyl-1H-pyrazol-4-yl)-1H-pyrrolo[2,3-b]pyridine-3-carbonyl]-phenyl}-benzenesulfonamide (P-0020), N-{2,4-Difluoro-3-[5-(1-methyl-1H-pyrazol-4-yl)-1H-pyrrolo[2,3-b]pyridine-3-carbonyl]-phenyl}-4-propyl-benzenesulfonamide (P-0021), N-{2,4-Difluoro-3-[5-(5-methyl-1H-imidazol-2-yl)-1H-pyrrolo[2,3-b]pyridine-3-carbonyl]-phenyl}-4-propyl-benzenesulfonamide (P-0023), and 3-Difluoromethoxy-N-{2,4-difluoro-3-[5-(5-methyl-1H-imidazol-2-yl)-1H-pyrrolo[2,3-b]pyridine-3-carbonyl]-phenyl}-benzenesulfonamide (P-0024), 5-Methyl-thiophene-2-sulfonic acid [3-(5-chloro-1H-pyrrolo[2,3-b]pyridine-3-carbonyl)-2,4-difluoro-phenyl]-amide (P-0028), 1-Methyl-1H-pyrazole-3-sulfonic acid [3-(5-chloro-1H-pyrrolo[2,3-b]pyridine-3-carbonyl)-2,4-difluoro-phenyl]-amide (P-0029), N-[2,4-Difluoro-3-(5-methyl-1H-pyrrolo[2,3-b]pyridine-3-carbonyl)-phenyl]-4-trifluoromethyl-benzenesulfonamide (P-0030), N-[3-(5-Cyano-1H-pyrrolo[2,3-b]pyridine-3-carbonyl)-2,4-difluoro-phenyl]-4-trifluoromethyl-benzenesulfonamide (P-0031), (E)-3-{3-[2,6-Difluoro-3-(4-trifluoromethyl-benzenesulfonylamino)-benzoyl]-1H-pyrrolo[2,3-b]pyridin-5-yl}-acrylic acid methyl ester (P-0032), and Pyridine-2-sulfonic acid [2,4-difluoro-3-(5-methoxy-1H-pyrrolo[2,3-b]pyridine-3-carbonyl)-phenyl]-amide (P-0036)

The following table indicates the azaindole used in step 3 (column 2) and the sulfonyl chloride used in step 6 (column 3) to afford the target compound (column 4). The compound number is provided in column 1, with the observed mass given in column 5.

| | Azaindole | Sulfonyl chloride |
|---|---|---|
| P-0001 | 5-chloro-7-azaindole | benzo[b]thiophene-3-sulfonyl chloride |
| P-0002 | 5-chloro-7-azaindole | 2-trifluoromethyl-5-methylfuran-3-sulfonyl chloride |
| P-0003 | 5-chloro-7-azaindole | 5-(oxazol-5-yl)thiophene-2-sulfonyl chloride |
| P-0004 | 5-chloro-7-azaindole | 3-(chlorosulfonyl)benzoic acid |
| P-0005 | 5-chloro-7-azaindole | 2-oxo-2H-chromene-6-sulfonyl chloride |
| P-0006 | 5-chloro-7-azaindole | 5-(isoxazol-5-yl)thiophene-2-sulfonyl chloride |
| P-0007 | 5-chloro-7-azaindole | 4-butoxybenzenesulfonyl chloride |

-continued
| | | |
|---|---|---|
| P-0008 | 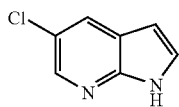 | 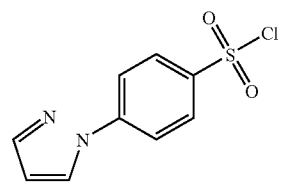 |
| P-0009 | 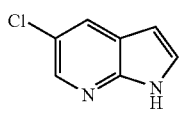 | 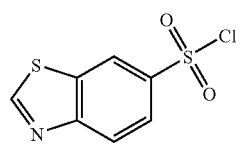 |
| P-0010 | 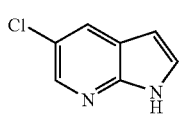 | 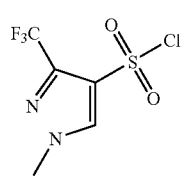 |
| P-0011 | 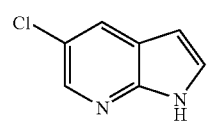 | 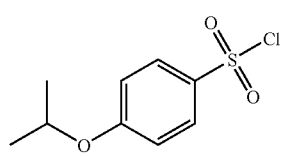 |
| P-0013 | 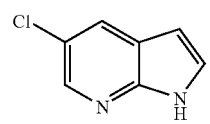 | 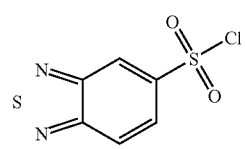 |
| P-0014 | 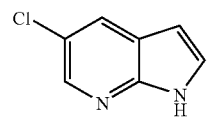 | 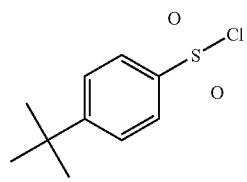 |
| P-0015 | 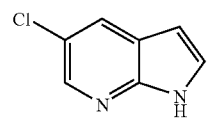 | 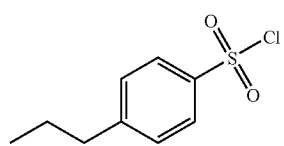 |
| P-0016 | 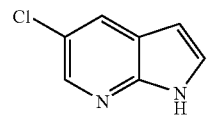 | 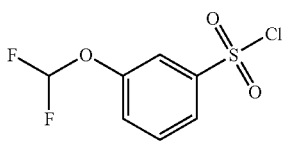 |
| P-0017 | 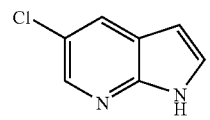 | 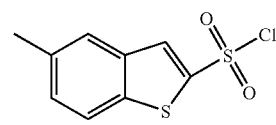 |

-continued
P-0020 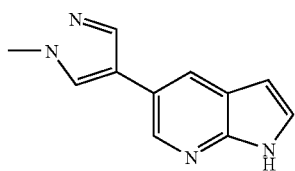 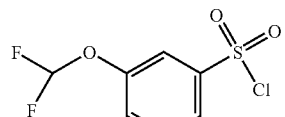
P-0021 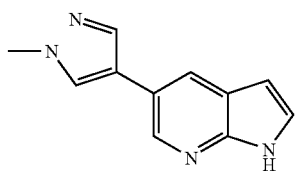 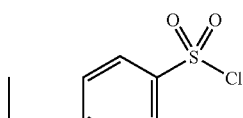
P-0023 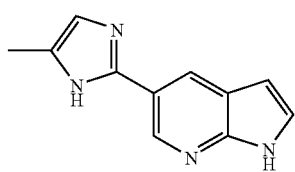 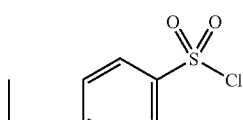
P-0024 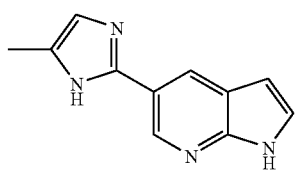 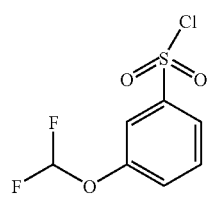
P-0028 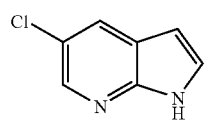 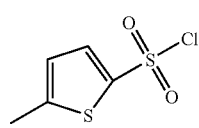
P-0029 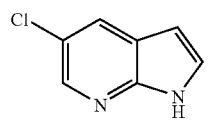 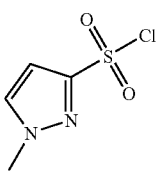
P-0030 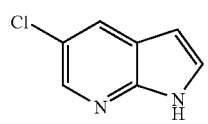 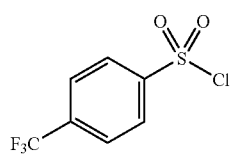
P-0031 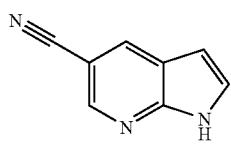 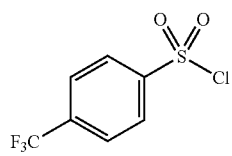
P-0032 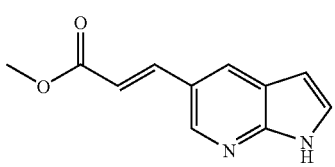 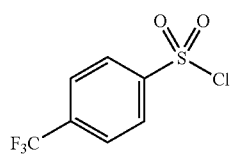

-continued
| | | | |
|---|---|---|---|
| P-0036 | 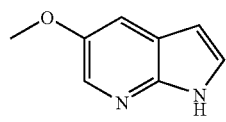 | | 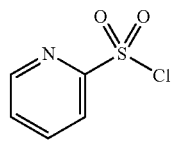 |
| Compound | MS(ESI) [M + H⁺]⁺ observed |
|---|---|
| P-0001 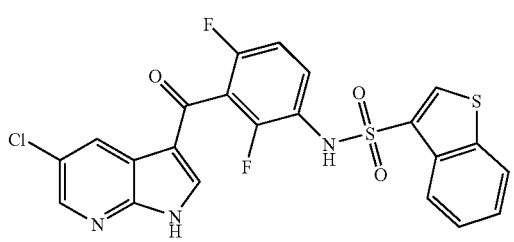 | 503.96 |
| P-0002 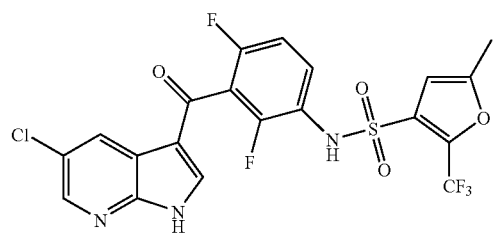 | |
| P-0003 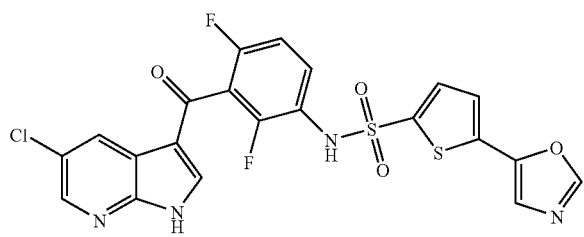 | 520.3 |
| P-0004 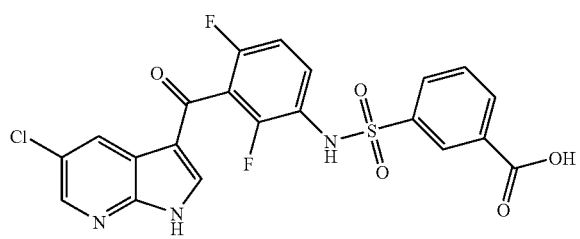 | 491.9 |
| P-0005 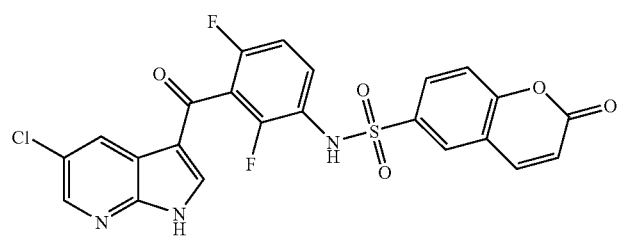 | 515.9 |

-continued
| | | |
|---|---|---|
| P-0006 | 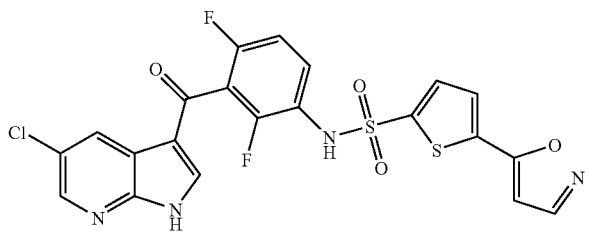 | 521.1 |
| P-0007 | 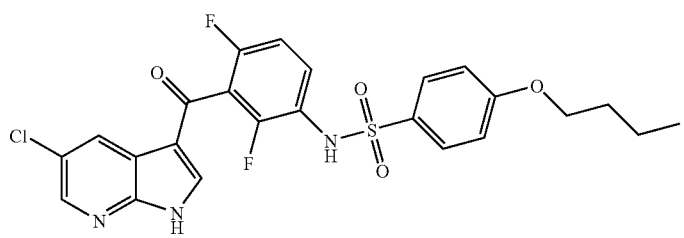 | 519.9 |
| P-0008 | 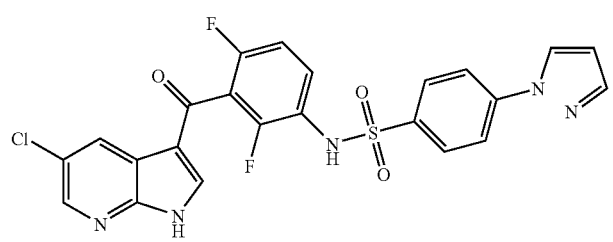 | 514.3 |
| P-0009 | 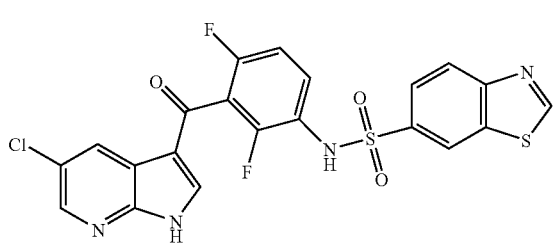 | 505.1 |
| P-0010 | 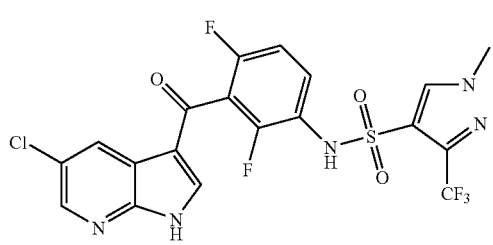 | 520.3 |
| P-0011 | 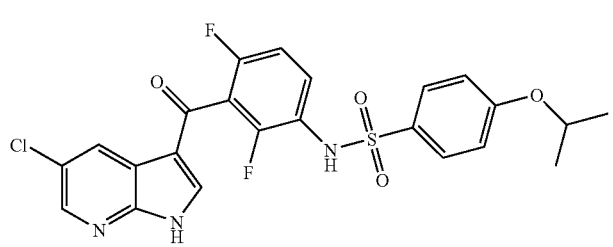 | 505.9 |

-continued
| | | |
|---|---|---|
| P-0013 | 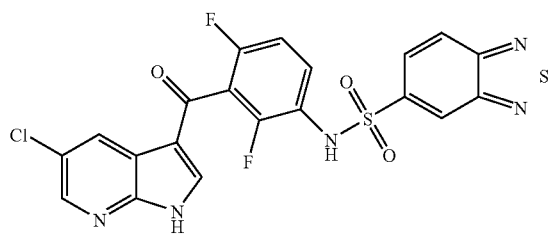 | 505.9 |
| P-0014 | 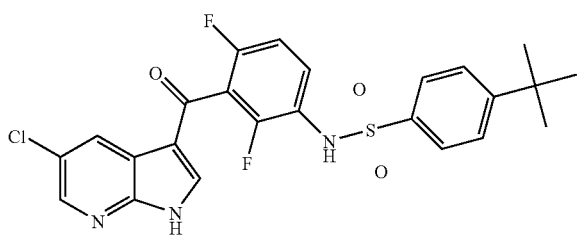 | 503.9 |
| P-0015 | 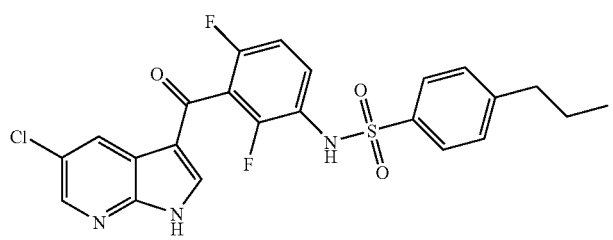 | 490.3 |
| P-0016 | 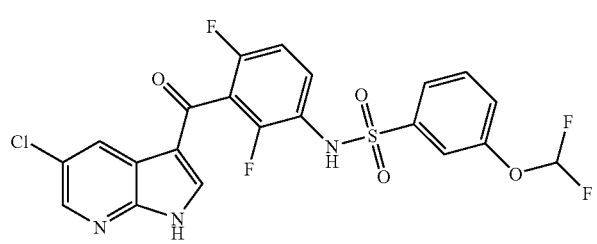 | 514.3 |
| P-0017 | 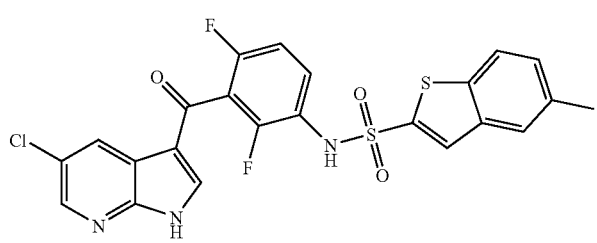 | 517.9 |
| P-0020 | 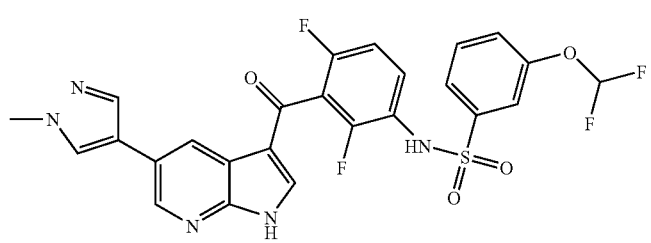 | 560 |

-continued
| | | |
|---|---|---|
| P-0021 | 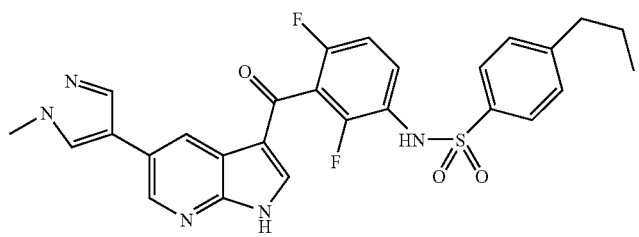 | 536 |
| P-0023 | 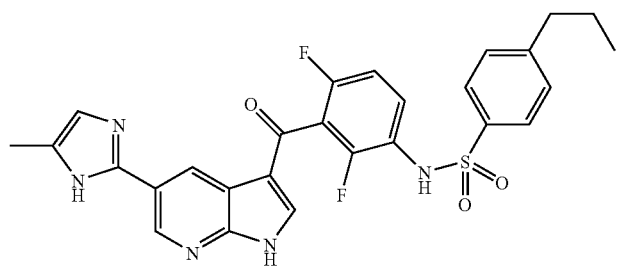 | 536 |
| P-0024 | 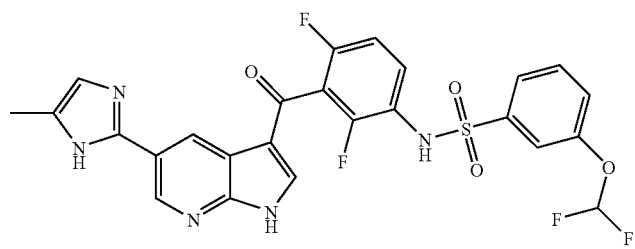 | 560 |
| P-0028 | 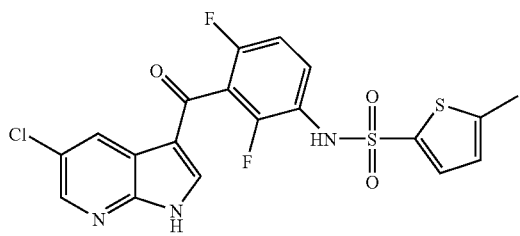 | 469 |
| P-0029 | 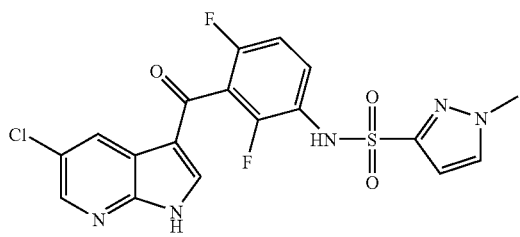 | 453 |
| P-0030 | 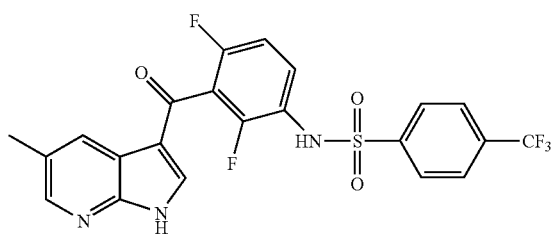 | 496 |

-continued

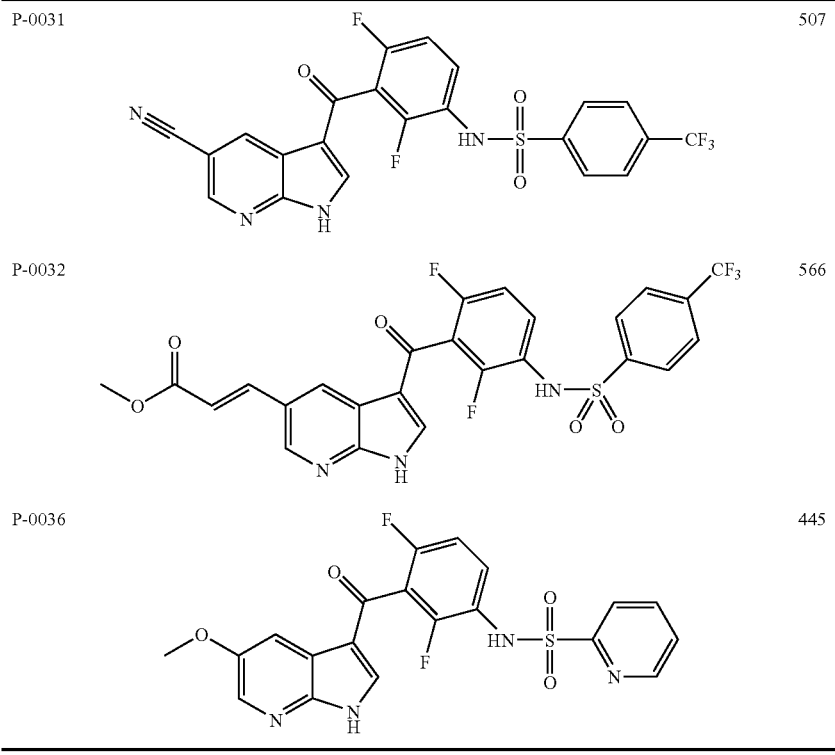

| | | |
|---|---|---|
| P-0031 | | 507 |
| P-0032 | | 566 |
| P-0036 | | 445 |

Example 18

Synthesis of 3-{3-[2,6-difluoro-3-(4-trifluoromethyl-benzenesulfonylamino)-benzoyl]-1H-pyrrolo[2,3-b]pyridin-5-yl}-N-ethyl-propionamide P-0035

3-{3-[2,6-Difluoro-3-(4-trifluoromethyl-benzenesulfonylamino)-benzoyl]-1H-pyrrolo[2,3-b]pyridin-5-yl}-N-ethyl-propionamide P-0035 was synthesized in three steps from (E)-3-{3-[2,6-Difluoro-3-(4-trifluoromethyl-benzenesulfonylamino)-benzoyl]-1H-pyrrolo[2,3-b]pyridin-5-yl}-acrylic acid methyl ester P-0032 as shown in Scheme 15.

Scheme 15

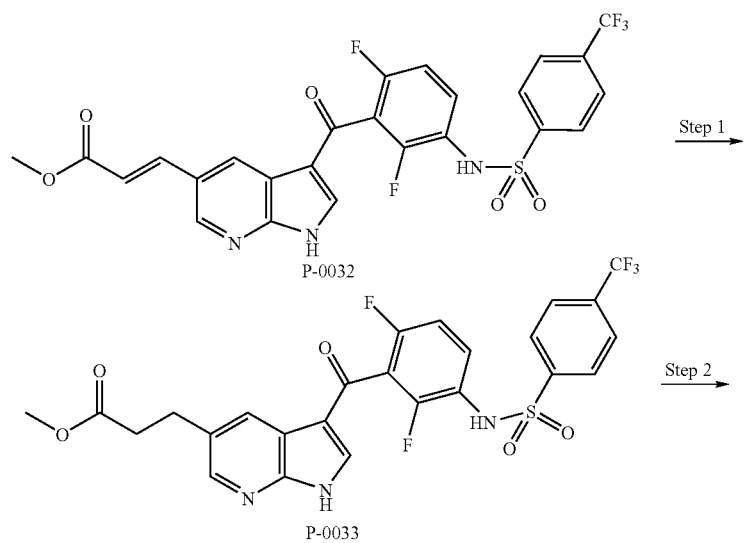

-continued

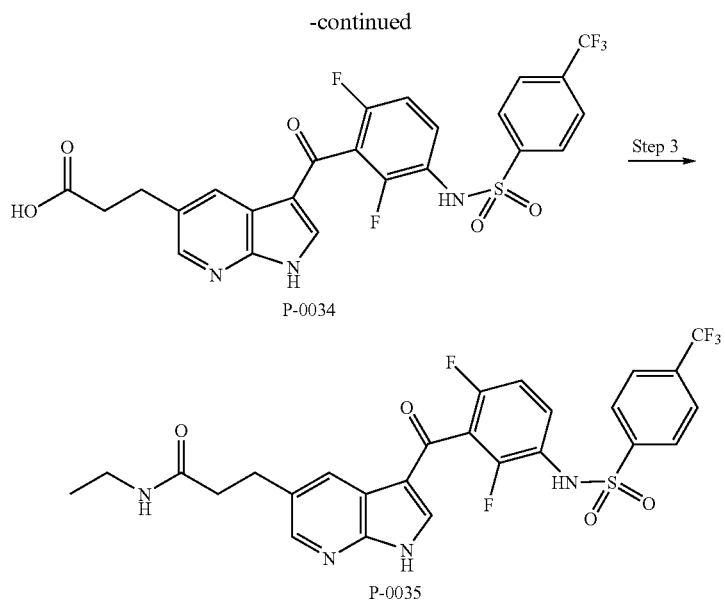

Step 1-Preparation of 3-{3-[2,6-difluoro-3-(4-trifluoromethyl-benzenesulfonylamino)-benzoyl]-1H-pyrrolo[2,3-b]pyridin-5-yl}-propionic acid methyl ester (P-0033)

To (E)-3-{3-[2,6-difluoro-3-(4-trifluoromethyl-bezenesulfonylamino)-benzoyl]-1H-pyrrolo[2,3-b]pyridin-5-yl}-acrylic acid methyl ester (P-0032, 229 mg, 0.41 mmol, prepared as described in Example 17) was added methanol (15 mL) and tetrahydrofuran (5 mL). The solution was degassed with nitrogen for 5 minutes, followed by the addition of Pd/C (10% weight, 30 mg). The reaction mixture was allowed to stir under an atmosphere of hydrogen at room temperature for 18 hrs. After removing Pd/C and volatiles, the residue was purified through a quick silica plug eluted with ethyl acetate. Solvent was removed to provide an off-white solid (P-0033, 222 mg, 96%). MS(ESI) [M+H+]+=568.3.

Step 2—Preparation of 3-{3-[2,6-difluoro-3-(4-trifluoromethyl-benzenesulfonylamino)-benzoyl]-1H-pyrrolo[2,3-b]pyridin-5-yl}-propionic acid (P-0034)

To 3-{3-[2,6-difluoro-3-(4-trifluoromethyl-benzenesulfonylamino)-benzoyl]-1H-pyrrolo[2,3-b]pyridin-5-yl}-propionic acid methyl ester (P-0033, 215 mg, 0.38 mmol) dissolved in tetrahydrofuran (30 mL) was added 1 N lithium hydroxide solution (15 mL). The mixture was heated at 50° C. for 2 hrs, then acidified to pH~1-2 with 6 N HCl and extracted with ethyl acetate. The organic layer was washed with water and brine dried over anhydrous magnesium sulfate, filtered and concentrated to provide an off-white solid (P-0034, 202 mg, 96%). MS(ESI) [M+H+]+=554.0.

Step 3—Preparation of 3-{3-[2,6-difluoro-3-(4-trifluoromethyl-benzenesulfonylamino)-benzoyl]-1H-pyrrolo[2,3-b]pyridin)-5-yl}-N-ethyl-propionamide (P-0035)

To 3-{3-[2,6-difluoro-3-(4-trifluoromethyl-benzenesulfonylamino)-benzoyl]-1H-pyrrolo[2,3-b]pyridin-5-yl}-propionic acid (P-0034, 42 mg, 0.076 mmol) dissolved in tetrahydrofuran (3 mL) was added a 2.0 M solution of ethylamine in tetrahydrofuran (110 µL, 0.23 mmol) and N-(3-dimethylaminopropyl)-N'-ethylcarbodiimide hydrochloride (29 mg, 0.15 mmol). The reaction mixture was stirred at room temperature for 16 hrs, then extracted with ethyl acetate and water. The organic layer was washed with water and brine, dried over anhydrous magnesium sulfate, filtered and concentrated. The desired compound was isolated by silica gel column chromatography (methanol/dichloromethane), with the eluting solvents removed via lyophilizing to provide a white fluffy solid (P-0035, 13 mg, 30%). MS(ESI) [M+H+]+=581.0.

Example 19

Kinase Activity Assays

Assays for the activity of kinases, including, but not limited to, B-Raf, B-Raf V600E, B-Raf V6000E/T5291 and c-Raf-1 are known in the art, for example as described in U.S. patent application Ser. No. 11/473,347 (see Iso, PCT publication WO2007002433), the disclosure of which is hereby incorporated by reference in its entirety.

Representative compounds screened by at least one of the methods described in U.S. patent application Ser. No. 11/473,347, or by similar methods, having $IC_{50}$ of less than 10 µM under the test conditions employed are shown in tables 1a (B-Raf), 1b (B-Raf V600E), 1c (B-Raf V600E/T529I), 1d (Btk), 1e (c-Raf-1), 1f (Flt1), 1g (Fms), 1h (Jnk1), 1i (Kdr), 1j (Kit), 1k (Src), 1l (TEC), 1m (p38), and 1n (HGK).

TABLE 1a

Representative compounds with activity toward kinase B-Raf with $IC_{50} \leq 10$ µM under the test conditions employed.

| | |
|---|---|
| B-Raf | P-0001, P-0002, P-0003, P-0005, P-0006, P-0007, P-0009, P-0011, P-0013, P-0014, P-0015, P-0016, P-0017, P-0018, P-0019, P-0020, P-0021, P-0022, P-0023, P-0024, P-0025, P-0026, P-0027, P-0028, P-0030, P-0031, P-0032, P-0033, P-0034, P-0035, P-0036 |

TABLE 1b

Representative compounds with activity toward kinase B-Raf V600E with $IC_{50} \leq 10$ μM under the test conditions employed.

B-Raf V600E: P-0001, P-0002, P-0003, P-0005, P-0006, P-0007, P-0009, P-0013, P-0014, P-0015, P-0016, P-0017, P-0019, P-0020, P-0021, P-0022, P-0023, P-0024, P-0025, P-0028, P-0029, P-0030, P-0031, P-0032, P-0033, P-0034, P-0035

TABLE 1c

Representative compounds with activity toward kinase B-Raf V600E/T529I with $IC_{50} \leq 10$ μM under the test conditions employed.

B-Raf V600E T529I: P-0003, P-0005, P-0006

TABLE 1d

Representative compounds with activity toward kinase Btk with $IC_{50} \leq 10$ μM under the test conditions employed.

Btk: P-0013, P-0020, P-0021, P-0022, P-0023, P-0024

TABLE 1e

Representative compounds with activity toward kinase c-Raf-1 with $IC_{50} \leq 10$ μM under the test conditions employed.

c-Raf-1: P-0001, P-0002, P-0003, P-0005, P-0006, P-0007, P-0008, P-0009, P-0011, P-0013, P-0014, P-0015, P-0016, P-0017, P-0018, P-0019, P-0020, P-0021, P-0022, P-0023, P-0025, P-0030, P-0031

TABLE 1f

Representative compounds with activity toward kinase Flt1 with $IC_{50} \leq 10$ μM under the test conditions employed.

Flt1: P-0016, P-0020, P-0025, P-0026, P-0031

TABLE 1g

Representative compounds with activity toward kinase Fms with $IC_{50} \leq 10$ μM under the test conditions employed.

Fms: P-0001, P-0002, P-0003, P-0005, P-0006, P-0009, P-0010, P-0011, P-0013, P-0014, P-0015, P-0016, P-0020, P-0021, P-0022, P-0023, P-0024, P-0027, P-0028, P-0035

TABLE 1h

Representative compounds with activity toward kinase Jnk1 with $IC_{50} \leq 10$ μM under the test conditions employed.

Jnk1: P-0019, P-0020, P-0025

TABLE 1i

Representative compounds with activity toward kinase Kdr with $IC_{50} \leq 10$ μM under the test conditions employed.

Kdr: P-0001, P-0002, P-0003, P-0004, P-0005, P-0008, P-0010, P-0011, P-0013, P-0014, P-0016, P-0018, P-0019, P-0020, P-0021, P-0022, P-0023, P-0024, P-0025, P-0026, P-0027, P-0028, P-0029, P-0032, P-0034

TABLE 1j

Representative compounds with activity toward kinase Kit with $IC_{50} \leq 10$ μM under the test conditions employed.

Kit: P-0001, P-0002, P-0003, P-0005, P-0006, P-0007, P-0008, P-0009, P-0010, P-0011, P-0013, P-0014, P-0015, P-0016, P-0017, P-0018, P-0019, P-0020, P-0021, P-0022, P-0023, P-0024, P-0025, P-0026, P-0027, P-0028, P-0029, P-0032, P-0035

TABLE 1k

Representative compounds with activity toward kinase Src with $IC_{50} \leq 10$ μM under the test conditions employed.

Src: P-0002, P-0003, P-0004, P-0005, P-0006, P-0008, P-0009, P-0010, P-0011, P-0013, P-0015, P-0016, P-0017, P-0018, P-0019, P-0020, P-0021, P-0022, P-0023, P-0024, P-0025, P-0026, P-0028, P-0029, P-0031, P-0036

TABLE 1l

Representative compounds with activity toward kinase TEC with $IC_{50} \leq 10$ μM under the test conditions employed.

TEC: P-0016

TABLE 1m

Representative compounds with activity toward kinase p38 with $IC_{50} \leq 10$ μM under the test conditions employed.

P38: P-0020, P-0028, P-0029

TABLE 1n

Representative compounds with activity toward kinase HGK with $IC_{50} \leq 10$ μM under the test conditions employed.

HGK: P-0020

Example 19

Efficacy of Compounds in Combination with Standard-of-Care Chemotherapeutic Agents in Four Human Cancer Cell Lines Compounds of the invention, such as compounds of Formula I, Formula II, or Formula III, in combination with a standard chemotherapeutic agent, such as 5-fluorouracil, carboplatin, dacarbazine, gefitinib, oxaliplatin, paclitaxel, SN-38, temozolomide, or vinblastine, can be assessed for their effectiveness in killing human tumor cells. Human tumor cell lines, such as A-375 (malignant melanoma), SK-MFL-2 (malignant melanoma, skin metastasis), COLO 205

(colorectal adenocarcinoma, ascites metastasis) or SW-620 (colorectal adenocarcinoma, lymph node metastasis) can be treated with a compound of Formula I, Formula II, or Formula III alone, or in combination with one of the above-mentioned chemotherapeutic agents.

Tumor cells are grown as a monolayer at 37° C. in a humidified atmosphere (5% $CO_2$, 95% air). Cells are grown in a suitable culture medium, e.g. RPMI 1640 (Ref BE12-702F, Cambrex, Verviers, Belgium) containing 2 mM L-glutamine and supplemented with 10% fetal bovine serum (Ref DE14-801E, Cambrex). For experimental use, the tumor cells are detached from the culture flask by a 5-minute treatment with trypsin-versene (Ref 02-007E, Cambrex), diluted in Hanks' medium without calcium or magnesium (Ref BE10-543F, Cambrex). Trypsin treatment is neutralized by culture medium addition. The cells are counted in a hemocytometer and their viability assessed by 0.25% trypan blue exclusion.

The cell lines are checked for mycoplasma contamination with the Mycotect assay kit (Ref 15672-017, Invitrogen, Cergy-Pontoise, France) in accordance with the manufacturer's instructions. The mycoplasma test is assayed from the culture supernatants of the cell lines and compared to negative and positive controls.

The tumor cells (10,000 per well) are plated in 96-well flat-bottom microtitration plates (Ref 055260, Nunc, Dutscher, Brumath, France) and incubated at 37° C. for 24 hours before treatment in 100 µl of drug-free culture medium supplemented with 10% FBS. In order to assess the $IC_{50}$ of each compound to be used for each cell line, the tumor cells are incubated in a 200 µl final volume of RPMI 1640 supplemented with 10% FBS and containing either a compound of Formula I, Formula II, or Formula III, or one of 5-fluorouracil, carboplatin, dacarbazine, gefitinib, oxaliplatin, paclitaxel, SN-38, temozolomide, or vinblastine. The compounds are tested in a suitable concentration range, such as $10^{-8}$ to $10^{-3}$ M for a compound of Formula I, Formula II, or Formula III, 5-fluorouracil, dacarbazine or gefitinib, $10^{-9}$ to $10^{-4}$ M for carboplatin, oxaliplatin, or temozolomide, $10^{-11}$ to $10^{-6}$ M for paclitaxel or SN-38, and $10^{-15}$ to $10^{-10}$ M for vinblastine. Compounds of Formula I, Formula II, or Formula III are dissolved in DMSO and diluted with culture medium to the desired concentrations. 5-fluorouracil (50 mg/ml, Dakota Pharm, LePlessis Robinson, France), carboplatin (10 mg/ml, Aguettant, Lyon, France), and paclitaxel (6 mg/ml, Bristol-Myers Squibb SpA, Rueil Malmaison, France), are diluted with culture medium to the desired concentrations. Dacarbazine (Sigma, Saint Quentin Fallavier, France) and vinblastine (Lilly France S. A., Saint Cloud, France) are dissolved in NaCl 0.9% and diluted with culture medium to the desired concentrations. Gefitinib is dissolved in a mixed solution of RPMI 1640 and DMSO and diluted with culture medium to the desired concentrations (maximum final DMSO of 0.1% v/v). SN-38 (LKT Laboratories, Inc., St. Paul, Minn.) is dissolved in DMSO and diluted with culture medium to the desired concentrations (maximum final DMSO of 0.1% v/v). Temozolomide (LKT Laboratories, Inc., St. Paul, Minn.) is dissolved in water for injection and diluted with culture medium to the desired concentrations. Cells are incubated for 96 hours in the presence of test substances at 37° C. under 5% $CO_2$. At the end of treatments, the cytotoxic activity is evaluated by an MTT assay.

For the MTT assay, at the end of the cells treatment, 20 µl of a 5 mg/ml solution 0.22 µm filtered tetrazolium reagent (MTT, Ref M2128, Sigma) in Phosphate Buffered Saline (PBS, Ref BE17-517Q, Cambrex), is added in each well. Culture plates are incubated for 2 h at 37° C. The resulting supernatant is removed and formazan crystals dissolved with 200 µl of DMSO per well. Absorbency (OD) is measured at 570 nm in each well using VICTOR³™ 1420 multilabeled counter (Wallac, PerkinElmer, Courtaboeuf, France).

The $IC_{50}$ for each compound on each cell line is determined from the OD measurements of each sample. The dose response inhibition of cell proliferation is expressed as:

IC=(OD of drug exposed cells/OD of drug free wells)×100.

The mean of multiple measurements for each concentration is plotted vs. the drug concentration. The dose-response curves are plotted using XLFit 3 (IDBS, United Kingdom). The $IC_{50}$ (drug concentration to obtain 50% inhibition of cell proliferation) determination values are calculated using the XLFit 3 from semi-log curves. The $IC_{50}$ value determined for each compound in each cell line is used to determine the concentration of a compound of Formula I, Formula II, or Formula III, and of the standard chemotherapeutic to be used in combination.

The cells are treated with a combination of five concentrations of a compound of Formula I, Formula II, or Formula III and five concentrations of one of 5-fluorouracil, carboplatin, dacarbazine, gefitinib, oxaliplatin, paclitaxel, SN-38, temozolomide, or vi blastine, based on the $IC_{50}$ results. The compounds and cells are treated per the $IC_{50}$ determination described above and assayed by the MT assay.

The results are assessed to determine whether the combination is synergistic or antagonistic. The compound interactions are calculated by multiple drug effect analysis and are performed by the median equation principle according to the methodology described by Chou and Talalay (Adv. Enzyme Regul. 1984, 22: 27-55).

The combination index (CI) will be calculated by the Chou et al. equation (Adv. Enzyme Regul. 1984, 22: 27-55; Encyclopaedia of human biology, Academic Press, 1991, 2: 371-9; Synergism and Antagonism in Chemotherapy, Academic Press, 1991, 61-102) which takes into account both the potency ($D_m$ or $IC_{50}$) and the shape of the dose-effect curve (the m value). The general equation for the CI of the two compounds is given by:

$$CI = \frac{(D)_1}{(D_x)_1} + \frac{(D)_2}{(D_x)_2} + \frac{(D)_1(D)_2}{(D_x)_1(D_x)_2}$$

where:

$(D_x)_1$ and $(D_x)_2$ in the denominators are the doses (or concentrations) for compound I and compound 2 alone which demonstrate x % of inhibition, whereas $(D)_1$ and $(D)_2$ in the numerators are doses of both compounds (1 and 2) in combination that also inhibit x % (iso-effective). CI<1, =1, and >1 indicate synergism, additive effect and antagonism, respectively.

The $(D_x)_1$ and $(D_x)_2$ can be calculated from the median-effect equation of Chou et al. (J. Natl. Cancer Inst. 1994, 86: 1517-24):

$$D_x = D_m \left( \frac{f_a}{(1-f_a)} \right)^{1/m}$$

where:
D$_m$ is the median-effect dose that is obtained from the anti-log of x-intercept of the median-effect plot, x=log(D) versus y=log {f$_a$/(1−f$_a$)}, or D$_m$=10$^{-(y\text{-}intercept)/m}$; and in is the slope of the median-effect plot and f$_a$ is the fraction of cells affected by the treatment.

Each CI will be calculated with CalcuSyn software (Biosoft, UK) from the mean affected fraction at each drug ratio concentration.

Additional examples of certain methods contemplated by the present invention may be found in the following applications: U.S. Patent Publ. No. 2006/058339, application Ser. No. 11/154,287; U.S. Patent Publ. No. 2006/058340, application Ser. No. 11/154,988; U.S. Prov. App. No. 60/682,076, filed May 17, 2005; U.S. Prov. App. No. 60/682,058, filed May 17, 2005; U.S. Prov. App. No. 60/682,063, filed May 17, 2005; U.S. Prov. App. No. 60/682,051, filed May 17, 2005; U.S. Prov. App. No. 60/682,042, filed May 17, 2005; U.S. Prov. App. No. 60/692,750, filed Jun. 22, 2005; and U.S. Prov. App. No. 60/692,960, filed Jun. 22, 2005; U.S. Prov. App. No. 60/731,528, filed Oct. 28, 2005, U.S. patent application Ser. No. 11/435,381, filed May 16, 2006, and U.S. patent application Ser. No. 11/473,347, filed Jun. 21, 2006, each of which are hereby incorporated by reference herein in their entireties including all specifications, figures, and tables, and for all purposes.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to crystallization or co-crystallization conditions for Ret and Ret surrogate proteins and/or various kinase domain sequences can be used. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in term-s of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound having the chemical structure of Formula I,

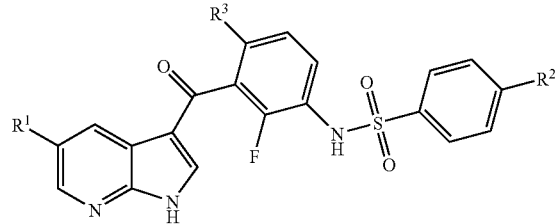

all salts, tautomers and isomers thereof,
wherein:
R$^1$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^4$, —SR$^4$, —NR$^5$R$^4$, —C(O)R$^4$, —C(S)R$^4$, —C(O)OR$^4$, —C(O)NR$^5$R$^4$, —C(S)NR$^5$R$^4$, —S(O)$_2$NR$^5$R$^4$, —NR$^5$C(O)R$^4$, —NR$^5$C(S)R$^4$, —NR$^5$S(O)$_2$R$^4$, —NR$^5$C(O)NH$_2$, —NR$^5$C(O)NR$^5$R$^4$, —NR$^5$C(S)NH$_2$, —NR$^5$C(S)NR$^5$R$^4$, —NR$^5$S(O)$_2$NH$_2$, —NR$^5$S(O)$_2$NR$^5$R$^4$, —S(O)R$^4$, and —S(O)$_2$R$^4$;

R$^2$ is selected from the group consisting of halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^4$, —SR$^4$, —NR$^5$R$^4$, —C(O)R$^4$, —C(S)R$^4$, —C(O)OR$^4$, —C(O)NR$^5$R$^4$, —C(S)NR$^5$R$^4$, —S(O)$_2$NR$^5$R$^4$, —NR$^5$C(O)R$^4$, —NR$^5$C(S)R$^4$, —NR$^5$S(O)$_2$R$^4$, —NR$^5$C(O)NH$_2$, —NR$^5$C(O)NR$^5$R$^4$, —NR$^5$C(S)NH$_2$, —NR$^5$C(S)NR$^5$R$^4$, —NR$^5$S(O)$_2$NH$_2$, —NR$^5$S(O)$_2$NR$^5$R$^4$, —S(O)R$^4$, and —S(O)$_2$R$^4$;

R³ is selected from the group consisting of hydrogen, fluoro and chloro;

R⁴ is selected from the group consisting of optionally substituted lower alkyl, optionally substituted lower alkenyl, provided, however, that when R⁴ is optionally substituted lower alkenyl, no alkene carbon thereof is bound to N, S, O, S(O), S(O)₂, C(O) or C(S) of —OR⁴, —SR⁴, —NR⁵R⁴, —C(O)R⁴, —C(S)R⁴, —C(O)OR⁴, —C(O)NR⁵R⁴, —C(S)NR⁵R⁴, —S(O)₂NR⁵R⁴, —NR⁵C(O)R⁴, —NR⁵C(S)R⁴, —NR⁵S(O)₂R⁴, —NR⁵C(O)NH₂, —NR⁵C(O)NR⁵R⁴, —NR⁵C(S)NH₂, —NR⁵C(S)NR⁵R⁴, —NR⁵S(O)₂NH₂, —NR⁵S(O)₂NR⁵R⁴, —S(O)R⁴, or —S(O)₂R⁴, optionally substituted lower alkynyl, provided, however, that when R⁴ is optionally substituted lower alkynyl, no alkyne carbon thereof is bound to N, S, O, S(O), S(O)₂, C(O) or C(S) of —OR⁴, —SR⁴, —NR⁵R⁴, —C(O)R⁴, —C(S)R⁴, —C(O)OR⁴, —C(O)NR⁵R⁴, —C(S)NR⁵R⁴, —S(O)₂NR⁵R⁴, —NR⁵C(O)R⁴—NR⁵C(S)R⁴, —NR⁵S(O)₂R⁴, —NR⁵C(O)NH₂, —NR⁵C(O)NR⁵R⁴, —NR⁵C(S)NH₂, —NR⁵C(S)NR⁵R⁴, —NR⁵S(O)₂NH₂, —NR⁵S(O)₂NR⁵R⁴, —S(O)R⁴, or —S(O)₂R⁴, optionally substituted cycloalkyl, optionally substituted heterocycloalkyl, optionally substituted aryl, and optionally substituted heteroaryl; and R⁵ is selected from the group consisting of hydrogen and optionally substituted lower alkyl, provided, however, the compound is not

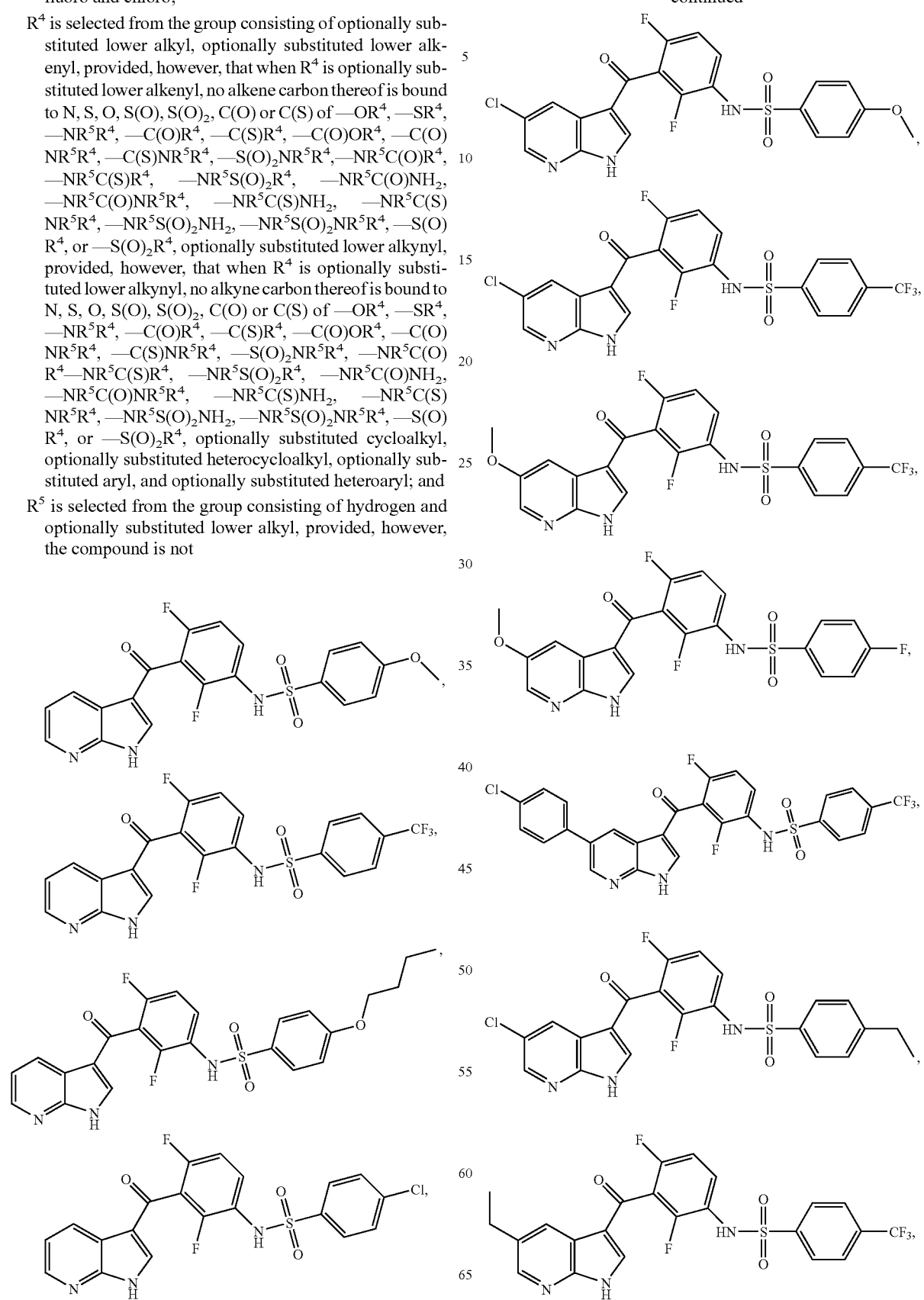

-continued
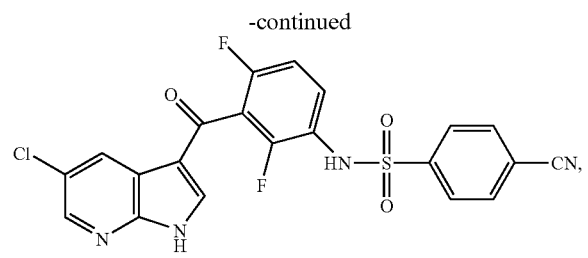
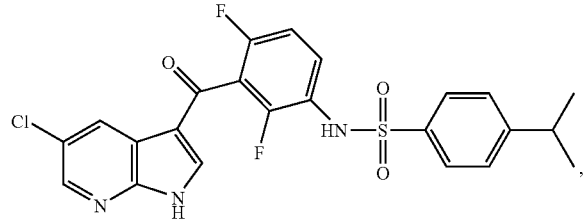
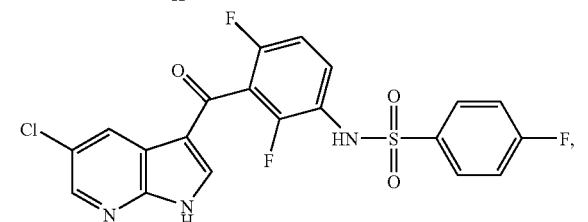
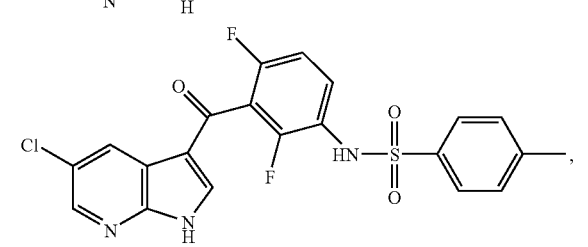
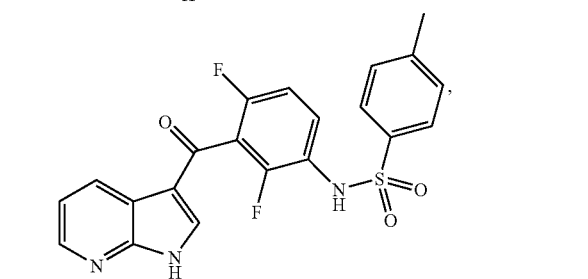
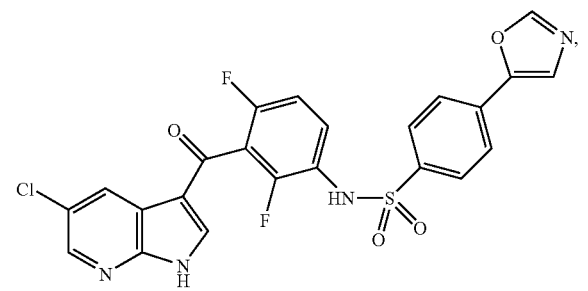
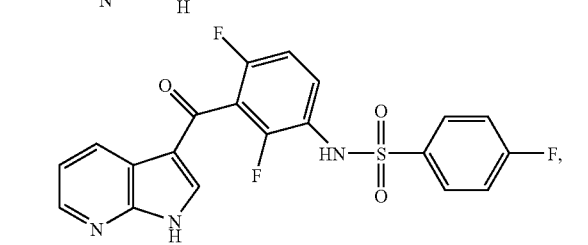
-continued
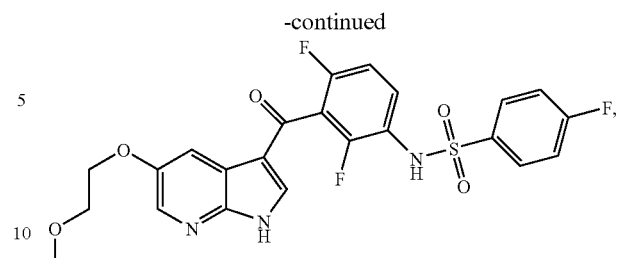
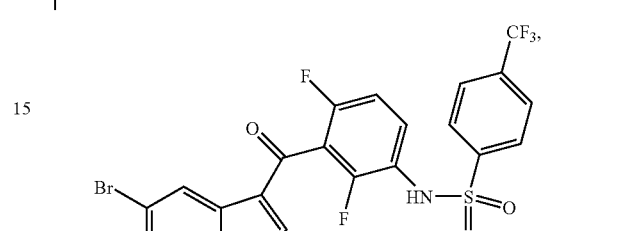
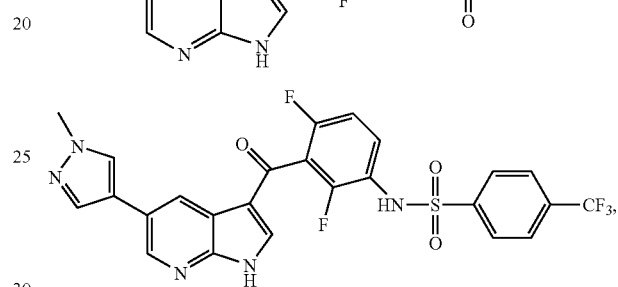
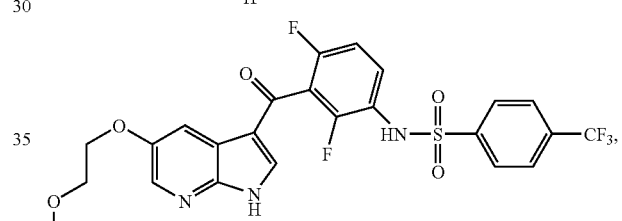
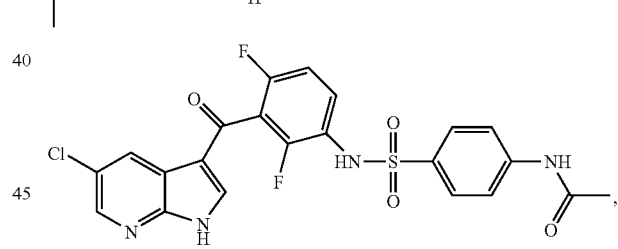
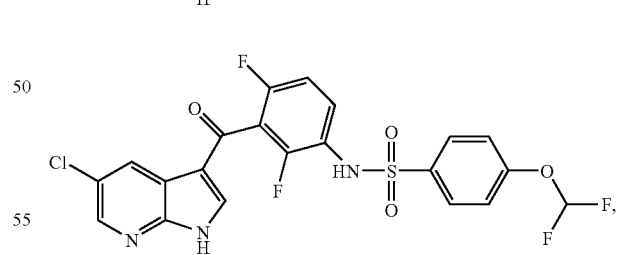
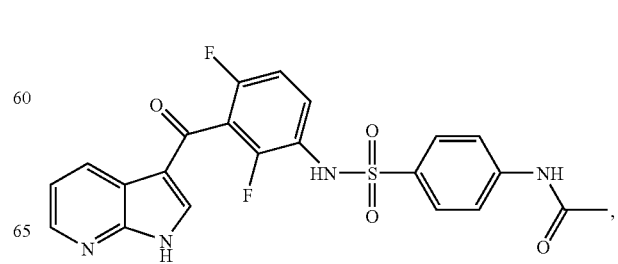

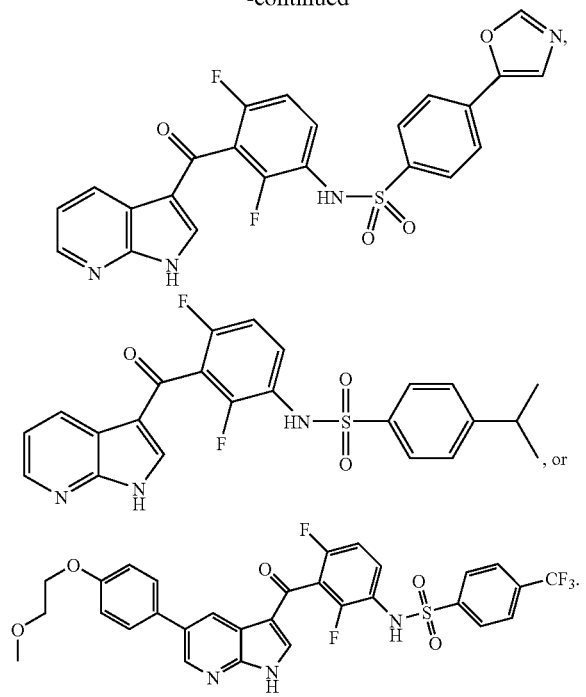

2. The compound of claim 1, wherein:

R$^1$ is selected from the group consisting of hydrogen, halogen, lower alkyl, lower alkenyl, lower alkynyl, cycloalkyl, heterocycloalkyl, aryl, heteroaryl, —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^7$, —SR$^7$, —NR$^8$R$^7$, —C(O)R$^7$, —C(S)R$^7$, —C(O)OR$^7$, —C(O)NR$^8$R$^7$, —C(S)NR$^8$R$^7$, S(O)$_2$NR$^8$R$^7$, —NR$^8$C(O)R$^7$, —NR$^8$C(S)R$^7$, —NR$^8$S(O)$_2$R$^7$, —NR$^8$C(O)NH$_2$, —NR$^8$C(O)NR$^8$R$^7$, —NR$^8$C(S)NH$_2$, —NR$^8$C(S)NR$^8$R$^7$, —NR$^8$S(O)$_2$NH$_2$, —NR$^8$S(O)$_2$NR$^8$R$^7$, —S(O)R$^7$, and —S(O)$_2$R$^7$, wherein lower alkyl, lower alkenyl or lower alkynyl are optionally substituted with one or more substituents selected from fluoro, —OH, —NH$_2$, C(O)OH, —C(O)NH$_2$, —OR$^7$, —NR$^8$R$^7$, —C(O)OR$^7$, —C(O)NR$^8$R$^7$, cycloalkyl, heterocycloalkyl, aryl, and heteroaryl, wherein cycloalkyl, heterocycloalkyl, aryl, and heteroaryl as R$^1$ or as substituents of lower alkyl, lower alkenyl or lower alkynyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NHR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino;

R$^2$ is selected from the group consisting of halogen, lower alkyl, cycloalkyl, heterocycloalkyl, aryl, heteroaryl, —OH, —NH$_2$, —CN, —NO$_2$, —C(O)OH, S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^7$, —SR$^7$, —NR$^8$R$^7$, —C(O)R$^7$, —C(S)R$^7$, —C(O)OR$^7$, —C(O)NR$^8$R$^7$, —C(S)NR$^8$R$^7$, —S(O)$_2$NR$^8$R$^7$, —NR$^8$C(O)R$^7$, —NR$^8$C(S)R$^7$, —NR$^8$S(O)$_2$R$^7$, —NR$^8$C(O)NH$_2$, —NR$^8$C(O)NR$^8$R$^7$, —NR$^8$C(S)NH$_2$, —NR$^8$C(S)NR$^8$R$^7$, —NR$^8$S(O)$_2$NH$_2$, —NR$^8$S(O)$_2$NR$^8$R$^7$, —S(O)R$^7$, and —S(O)$_2$R$^7$, wherein lower alkyl is optionally substituted with one or more substituents selected from fluoro, —OR$^7$, —NR$^8$R$^7$, cycloalkyl, heterocycloalkyl, aryl, and heteroaryl, wherein cycloalkyl, heterocycloalkyl, aryl, and heteroaryl as R$^2$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NHR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino;

R$^7$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R$^7$ or as substituents of lower alkyl are optionally substituted with one or more substituents selected from the group consisting of —OH, —NH$_2$, —CN, —NO$_2$, —S(O)NH), —C(O)NH$_2$, —OR$^9$, —SR$^9$, —NHR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino;

R$^8$ at each occurrence is independently hydrogen or lower alkyl; and

R$^9$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

3. The compound of claim 2, wherein:

R$^1$ is selected from the group consisting of hydrogen, —CN, —OR$^7$, —SR$^7$, —NR$^8$R$^7$, —NR$^8$C(O)R$^7$, —NR$^8$S(O)$_2$R$^7$—C(O)NR$^8$R$^7$, —C(O)R$^7$, —S(O)$_2$NR$^8$R$^7$, —S(O)R$^7$, —S(O)$_2$R$^7$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R$^1$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino; and R$^2$ is selected from the group consisting of —CN, —OR$^7$, —SR$^7$, —NR$^8$R$^7$, —NR$^8$C(O)R$^7$, —NR$^8$S(O)$_2$R$^7$, —(CO)NR$^8$R$^7$, —C(O)R$^7$, —S(O)$_2$NR$^8$R$^7$, —S(O)R$^7$, —S(O)$_2$R$^7$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, dialkylamino, cycloalkyl, heterocycloalkyl, aryl, and heteroaryl, as $R^2$ or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino.

4. The compound of claim 3, wherein:
$R^1$ is hydrogen, —CN, —NR$^8$R$^7$, —OR$^7$, —S(O)$_2$R$^7$, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^8$R$^7$, —OR$^7$ and —S(O)$_2$R$^7$, and
$R^2$ is —CN, fluoro, chloro, lower alkyl, fluoro substituted lower alkyl, —NR$^8$R$^7$, —OR$^7$ or —S(O)$_2$R$^7$.

5. The compound of claim 4, wherein:
$R^1$ is hydrogen, —CN, fluoro, chloro, lower alkyl, fluoro substituted lower alkyl, lower alkoxy, fluoro substituted lower alkoxy, lower alkoxy substituted C$_{2-6}$alkoxy, aryl or heteroaryl, wherein aryl or heteroaryl are optionally substituted with one or more substituents selected from the group consisting of fluoro, chloro, lower alkyl, fluoro substituted lower alkyl, lower alkoxy, fluoro substituted lower alkoxy, mono-alkylamino, di-alkylamino, and cycloalkylamino, and
$R^2$ is —CN, fluoro, chloro, lower alkyl, fluoro substituted lower alkyl, lower alkoxy, fluoro substituted lower alkoxy, mono-alkylamino, di-alkylamino, or cycloalkylamino.

6. The compound of claim 1, wherein the compound is selected from the group consisting of:
4-Butoxy—N-[3-(5-chloro-1H-pyrrolo[2,3-b]pyridine-3-carbonyl)-2,4-difluoro-phenyl]-benzenesulfonamide,
N-[3-(5—Chloro-1r-pyrrolo[2,3-b]pyridine-3-carbonyl)-2,4-difluoro-phenyl]-4-pyrazol-1-yl benzenesulfonamide,
N-[3-(5—Chloro-1H-pyrrolo[2,3-b]pyridine-3-carbonyl)-2,4-difluoro-phenyl]-4-isopropoxy-benzenesulfonamide,
4-tert-Butyl—N-[3-(5-chloro-1-pyrrolo[2,3-b]pyridine-3-carbonyl)-2,4-difluoro-phenyl]-benzenesulfonamide,
N-[3-(5—Chloro-1H-pyrrolo[2,3-b]pyridine-3-carbonyl)-2,4-difluoro-phenyl]-propyl-benzenesulfonamide,
N-{2,4-Difluoro-3-[5-(2-methoxy-ethoxy)-1H-pyrrolo[2,3-b]pyridine-3-carbonyl]-phenyl}-4-isopropyl-benzenesulfonamide,
N-{2,4-Difluoro-3-[5-(4-methyl-1H-imidazol-2-yl)-1H-pyrrolo[2,3-b]pyridine-3-carbonyl]-phenyl}-4-isopropyl-benzenesulfonamide,
4-Difluoromethoxy—N-{2,4-difluoro-3-[5-(1-methyl-1H-pyrazol-4-yl)-1H-pyrrolo[2,3-b]pyridine-3-carbonyl]-phenyl}-benzenesulfonamide,
N-{2,4-Difluoro-3-[5-(1-methyl-1H-pyrazol-4-yl)-1H-pyrrolo[2,3-b]pyridine-3-carbonyl]-phenyl}-4-propyl-benzenesulfonamide,
N-{2,4-Difluoro-3-[5-(1-methyl-1H-pyrazol-4-yl)-1H-pyrrolo[2,3-b]pyridine-3-carbonyl]-phenyl}-4-isopropyl-benzenesulfonamide,
N-{2,4-Difluoro-3-[5-(5-methyl-1H-imidazol-2-yl)-1H-pyrrolo[2,3-b]pyridine-3-carbonyl]-phenyl}-4-propyl-benzenesulfonamide,
N-{2,4-Difluoro-3-[5-(5-methyl-1H-imidazol-2-yl)-1H-pyrrolo[2,3-b]pyridine-3-carbonyl]-phenyl}-4-trifluoromethyl-benzenesulfonamide,
N-{2,4-Difluoro-3-[5-(1-methyl-1H-imidazol-2-yl)-1H-pyrrolo[2,3-b]pyridine-3-carbonyl]-phenyl}-4-propyl-benzenesulfonamide,
N-{3-[5-(1,5-Dimethyl-1H-imidazol-2-yl)-1H-pyrrolo[2,3-b]pyridine-3-carbonyl]-2,4-difluoro-phenyl}-4-propyl-benzenesulfonamide,
N-[2,4-Difluoro-3-(5-methyl-1H-pyrrolo[2,3-b]pyridine-3-carbonyl)-phenyl]-4-trifluoromethyl-benzenesulfonamide,
N-[3-(5—Cyano-1H-pyrrolo[2,3-b]pyridine-3-carbonyl)-2,4-difluoro-phenyl]-4-trifluoromethyl-benzenesulfonamide,
(E)-3-{3-[2,6-Difluoro-3-(4-trifluoromethyl-benzenesulfonylamino)-benzoyl]-1H-pyrrolo[2,3-b]pyridin-5-yl}-acrylic acid methyl ester,
3-{3-[2,6-Difluoro-3-(4-trifluoromethyl-benzenesulfonylamino)-benzoyl]-1H-pyrrolo[2,3-b]pyridin-5-yl}-propionic acid methyl ester,
3-{3-[2,6-Difluoro-3-(4-trifluoromethyl-benzenesulfonylamino)-benzoyl]-1H-pyrrolo[2,3-b]pyridin-5-yl}-propionic acid,
3-{3-[2,6-Difluoro-3-(4-trifluoromethyl-benzenesulfonylamino)-benzoyl]-1H-pyrrolo[2,3-b]pyridin-5-yl}—N-ethyl-propionamide; and
all salts, tautomers, and isomers thereof.

7. A compound having the chemical structure of Formula II,

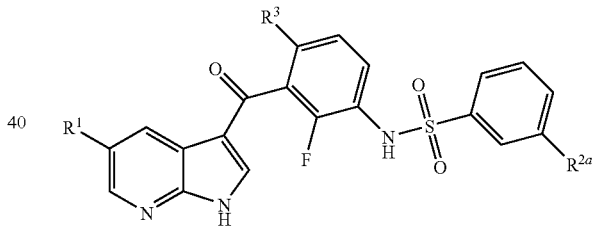

all salts, tautomers and isomers thereof,
wherein:
$R^1$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —NH$_2$, —CN, —NO$_2$, —C(O)OH, —S(O)$_2$NH$_2$, —C(O)NH$_2$, —C(S)NH$_2$, —NHC(O)NH$_2$, —NC(S)NH$_2$, —NHS(O)$_2$NH$_2$, —OR$^4$, —SR$^4$, —NR$^5$R$^4$, —C(O)R$^4$, —C(S)R$^4$, —C(O)OR$^4$, —C(O)NR$^5$R$^4$, —C(S)NR$^5$R$^4$, —S(O)$_2$NR$^5$R$^4$, —NR$^5$C(O)R$^4$, NR$^5$C(S)R$^4$, —NR$^5$S(O)$_2$R$^4$, —NR$^5$C(O)NH$_2$, —NR$^5$C(O)NR$^5$R$^4$, —NR$^5$C(S)NH$_2$, —NR$^5$C(S)NR$^5$R$^4$, —NR$^5$S(O)$_2$NH$_2$, —NR$^5$S(O)$_2$NR$^5$R$^4$, —S(O)R$^4$, and —S(O)$_2$R$^4$;
$R^{2a}$ is selected from the group consisting of halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —NH$_2$, —CN, —NO₂, —C(O)OH, —S(O)₂NH₂, —C(O)NH₂, —C(S)NH₂, —NHC(O)NH₂, —NHC(S)NH₂, —NHS(O)₂NH₂, —OR⁴, —SR⁴, —NR⁵R⁴, —C(O)R⁴, —C(S)R⁴, —C(O)OR⁴, —C(O)NR⁵R⁴, —C(S)NR⁵R⁴, —S(O)₂NR⁵R⁴, —NR⁵C(O)R⁴, —NR⁵C(S)R⁴, —NR⁵S(O)₂R⁴, —NR⁵C(O)NH₂, —NR⁵C(O)NR⁵R⁴, —NR⁵C(S)NH₂, —NR⁵C(S)NR⁵R⁴, —NR⁵S(O)₂NH₂, —NR⁵S(O)₂NR⁵R⁴, —S(O)R⁴, and —S(O)₂R⁴;

R³ is selected from the group consisting of hydrogen, fluoro and chloro;

R⁴ is selected from the group consisting of optionally substituted lower alkyl, optionally substituted lower alkenyl, provided, however, that when R⁴ is optionally substituted lower alkenyl, no alkene carbon thereof is bound to N, S, O, S(O), S(O)₂, C(O) or C(S) of —OR⁴, —SR⁴, —NR⁵R⁴, —C(O)R⁴, —C(S)R⁴, —C(O)OR⁴, —C(O)NR⁵R⁴, —C(S)NR⁵—S(O)₂NR⁵R⁴, —NR⁵C(O)R⁴, —NR⁵C(S)R⁴, —NR⁵S(O)₂R⁴, —NR⁵C(O)NH₂, —NR⁵C(O)NR⁵R⁴, —NR⁵C(S)NH₂, —NR⁵C(S)NR⁵R⁴, —NR⁵S(O)₂NH₂, —NR⁵S(O)₂NR⁵R⁴, —S(O)R⁴, or —S(O)₂R⁴, optionally substituted lower alkynyl, provided, however, that when R⁴ is optionally substituted lower alkynyl, no alkyne carbon thereof is bound to N, S, O, S(O), S(O)₂, C(O) or C(S) of —OR⁴, —SR⁴, —NR⁵R⁴, —C(O)R⁴, —C(S)R⁴, —C(O)OR⁴, —C(O)NR⁵R⁴, —C(S)NR⁵R⁴, —S(O)₂NR⁵R⁴, —NR⁵C(O)R⁴, —NR⁵C(S)R⁴, —NR⁵S(O)₂R—NR⁵C(O)NH₂, —NR⁵C(O)NR⁵R⁴, —NR⁵C(S)NH₂, —NR⁵C(S)NR⁵R⁴, —NR⁵S(O)₂NH₂, —NR⁵S(O)₂NR⁵R⁴, —S(O)R⁴, or —S(O)₂R⁴, optionally substituted cycloalkyl, optionally substituted heterocycloalkyl, optionally substituted aryl, and optionally substituted heteroaryl; and R⁵ is selected from the group consisting of hydrogen and optionally substituted lower alkyl, provided, however, the compound is not

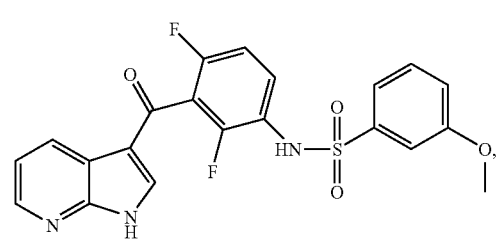

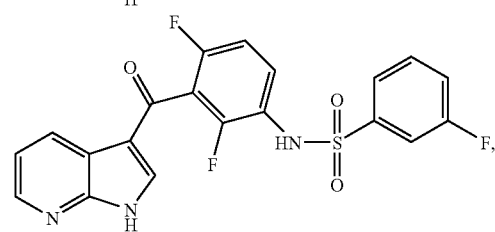

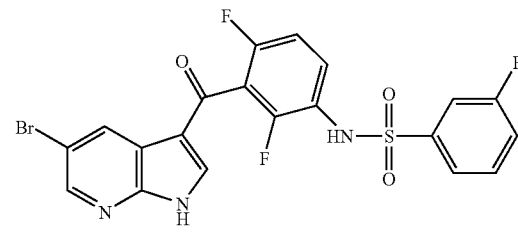

-continued

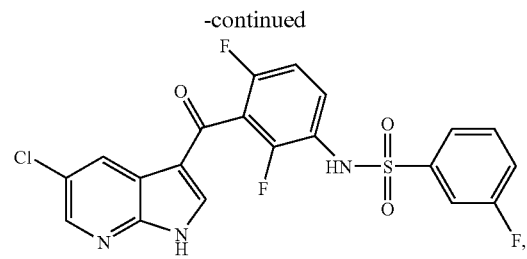

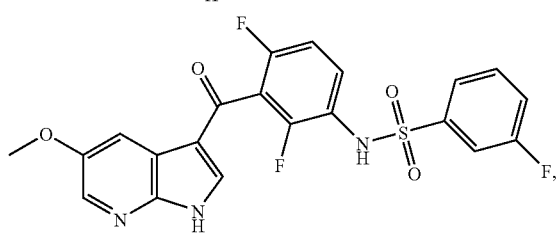

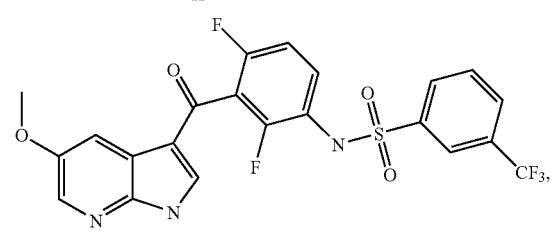

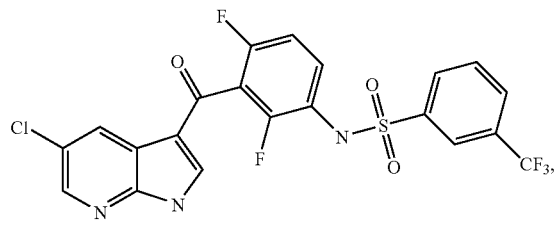

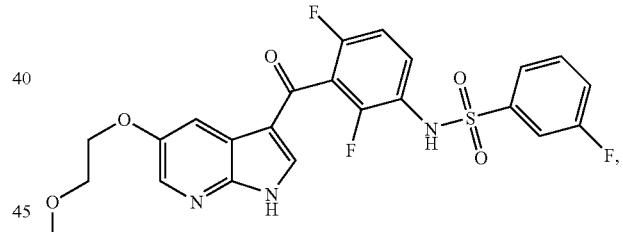

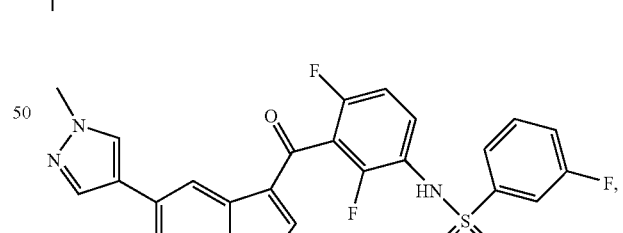

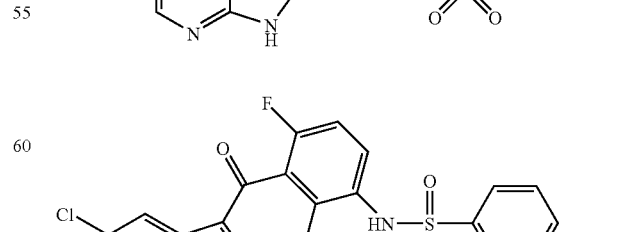

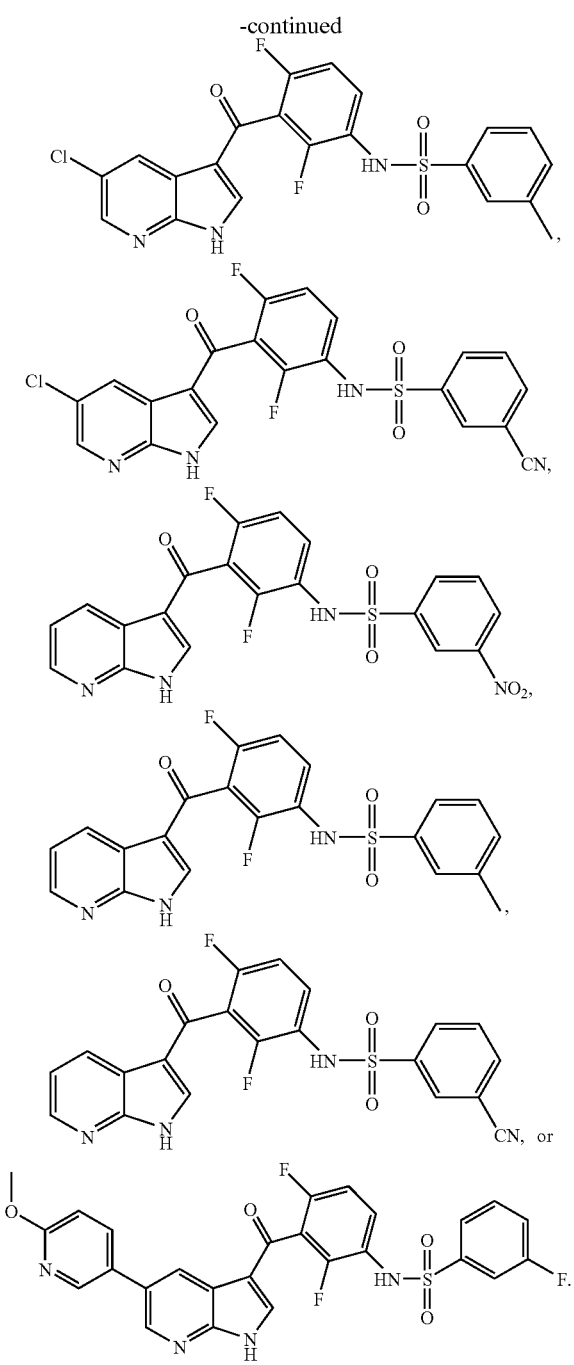

8. The compound of claim 7, wherein:

R¹ is selected from the group consisting of hydrogen, halogen, lower alkyl, lower alkenyl, lower alkynyl, cycloalkyl, heterocycloalkyl, aryl, heteroaryl, —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^7$, —SR$^7$, —NR$^8$R$^7$, —C(O)R$^7$, —C(S)R$^7$, —C(O)OR$^7$, —C(O)NR$^8$R$^7$, —C(S)NR$^8$R$^7$, —S(O)$_2$NR$^8$R$^7$, —NR$^8$C(O)R$^7$, —NR$^8$C(S)R$^7$, —NR$^8$S(O)$_2$R$^7$, —NR$^8$C(O)NH$_2$, —NR$^8$C(O)NR$^8$R$^7$, —NR$^8$C(S)NH$_2$, —NR$^8$C(S)NR$^8$R$^7$, —NR$^8$S(O)$_2$NH$_2$, —NR$^8$S(O)$_2$NR$^8$R$^7$, —S(O)R$^7$, and —S(O)$_2$R$^7$, wherein lower alkyl, lower alkenyl or lower alkynyl are optionally substituted with one or more substituents selected from fluoro, —OH, —NH$_2$, C(O)OH, —C(O)NH$_2$, —OR$^7$, —NR$^8$R$^7$, —C(O)OR$^7$, —C(O)NR$^8$R$^7$, cycloalkyl, heterocycloalkyl, aryl, and heteroaryl, wherein cycloalkyl, heterocycloalkyl, aryl, and heteroaryl as R$^1$ or as substituents of lower alkyl, lower alkenyl or lower alkynyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NR$^8$R$^9$, —NR$^8$C(O)R$^9$, —NR$^8$S(O)—R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino;

R$^{2a}$ is selected from the group consisting of halogen, lower alkyl, cycloalkyl, heterocycloalkyl aryl, heteroaryl, —OH, —NH$_2$, —CN, —NO$_2$, —C(O)OH, —S(O)$_2$NH$_2$, —C(O)NH$_2$, —C(S)NH, —NHC(O)NH$_2$, —NHC(S)NH$_2$, —NHS(O)$_2$NH$_2$, —OR$^7$, —SR$^7$, —NR$^8$R$^7$, —C(O)R$^7$, —C(S)R$^7$, —C(O)OR$^7$, —C(O)NR$^8$R$^7$, —C(S)NR$^8$R$^7$, —S(O)$_2$NR$^8$R$^7$, —NR$^8$C(O)R$^7$, NR$^8$C(S)R$^7$, —NR$^7$S(O)$_2$R$^7$, —NR$^8$C(O)NH$_2$, —NR$^8$C(O)NR$^8$R$^7$, —NR$^8$C(S)NH$_2$, —NR$^8$C(S)NR$^8$R$^7$, —NR$^8$S(O)$_2$NH$_2$, —NR$^8$S(O)$_2$NR$^8$R$^7$, —S(O)R$^7$, and —S(O)$_2$R$^7$, wherein lower alkyl is optionally substituted with one or more substituents selected from fluoro, —OR$^7$, —NR$^8$R$^7$, cycloalkyl, heterocycloalkyl, aryl, and heteroaryl, wherein cycloalkyl, heterocycloalkyl, aryl, and heteroaryl as R$^{2a}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NHR$^9$—NR$^8$R$^8$, —NR$^8$C(O)R$^8$, —NR$^8$S(O)$_2$R$^9$, —S(O)$_2$R$^9$, —S(O)$_2$NR$^8$R$^9$,—C(O)R$^9$, —C(O)NR$^8$R$^9$, halogen, lower alkyl, fluoro substituted lower alkyl, and cycloalkylamino;

R$^7$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R$^7$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$,—NHR$^9$—NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino;

R$^8$ at each occurrence is independently hydrogen or lower alkyl; and

R$^9$ at each occurrence is independently selected from the group consisting of lower alkyl, heterocycloalkyl and heteroaryl, wherein lower alkyl is optionally substituted with one of more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

9. The compound of claim 8, wherein:

$R^1$ is selected from the group consisting of hydrogen, —CN, —OR$^7$, —SR$^7$, —NR$^8$R$^7$, —NR$^8$C(O)R$^7$, —NR$^8$S(O)$_2$R$^7$, —C(O)NR$^8$R$^7$, —C(O)R$^7$, —S(O)$_2$NR$^8$R$^7$, —S(O)R$^7$, —S(O)—R$^7$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^1$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino; and $R^{2a}$ is selected from the group consisting of —CN, —OR$^7$, —SR$^7$, —NR$^8$R$^7$, —NR$^8$C(O)R$^7$, —NR$^8$S(O)$_2$R$^7$, —C(O)NR$^8$R$^7$, —C(O)R$^7$, —S(O)$_2$NR$^8$R$^7$, —S(O)R$^7$, —S(O)$_2$R$^7$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{2a}$ or as a substituent of lower alkyl are optionally substituted with one or more substituents selected from the group consisting of —OH, —NH$_2$, —CN, —NO$_2$, —S(O)$_2$N$_2$, —C(O)NH$_2$, —OR$^9$, —SR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino.

10. The compound of claim 9, wherein:

$R^1$ is hydrogen, —CN, —NR$^8$R$^7$, —OR$^7$, —S(O)$_2$R$^7$, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^8$R$^7$, —OR$^7$ and —S(O)$_2$R$^7$, and $R^{2a}$ is —CN, fluoro, chloro, lower alkyl, fluoro substituted lower alkyl, —NR$^8$R$^7$, —OR$^7$ or —S(O)$_2$R$^7$.

11. The compound of claim 10, wherein:

$R^1$ is hydrogen, —CN, fluoro, chloro, lower alkyl, fluoro substituted lower alkyl, lower alkoxy, fluoro substituted lower alkoxy, lower alkoxy substituted $C_{2-6}$alkoxy, aryl or heteroaryl, wherein aryl or heteroaryl are optionally substituted with one or more substituents selected from the group consisting of fluoro, chloro, lower alkyl, fluoro substituted lower alkyl, lower alkoxy, fluoro substituted lower alkoxy, mono-alkylamino, di-alkylamino, and cycloalkylamino, and $R^{2a}$ is —CN, fluoro, chloro, lower alkyl, fluoro substituted lower alkyl, lower alkoxy, fluoro substituted lower alkoxy, mono-alkylamino, di-alkylamino, or cycloalkylamino.

12. The compound of claim 7, wherein the compound is selected from the group consisting of:

3-[3-(5—Chloro-1-pyrrolo[2,3-b]pyridine-3-carbonyl)-2,4-difluoro-phenylsulfamoyl]-benzoic acid, N-[3-(5—Chloro-1H-pyrrolo[2,3-b]pyridine-3-carbonyl)-2,4-difluoro-phenyl]-3-difluoromethoxy-benzenesulfonamide, 3-Difluoromethoxy—N-{2,4-difluoro-3-[5-(5-methyl-1H-imidazol-2-yl)-1H-pyrrolo[2,3-b]pyridine-3-carbonyl]-phenyl}-benzenesulfonamide; and all salts, tautomers, and isomers thereof.

13. A compound having the chemical structure of Formula III,

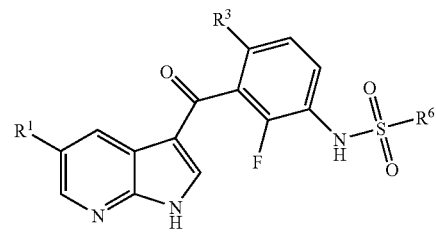

all salts, tautomers and isomers thereof, wherein:

$R^1$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^4$, —SR$^4$, —NR$^5$R$^4$, —C(O)R$^4$, —C(S)R$^4$, —C(O)OR$^4$, —C(O)NR$^5$R$^4$, —C(S)NR$^5$R$^4$, —S(O)$_2$NR$^5$R$^4$, —NR$^5$C(O)R$^4$, —NR$^5$C(S)R$^4$, —NR$^5$S(O)$_2$R$^4$, —NR$^5$C(O)NH$_2$, —NR$^5$C(O)NR$^5$R$^4$, —NR$^5$C(S)NH$_2$, —NR$^5$C(S)NR$^5$R$^4$, —NR$^5$S(O)$_2$NH$_2$, —NR$^5$S(O)$_2$NR$^5$R$^4$, —S(O)R$^4$, and —S(O)$_2$R$^4$;

$R^3$ is selected from the group consisting of hydrogen, fluoro and chloro;

$R^4$ is selected from the group consisting of optionally substituted lower alkyl, optionally substituted lower alkenyl, provided, however, that when $R^4$ is optionally substituted lower alkenyl, no alkene carbon thereof is bound to N, S, O, S(O), S(O)$_2$, C(O) or C(S) of —OR$^4$, SR$^4$, —NR$^5$R$^4$C(O)R$^4$, C(S)R$^4$, —C(O)OR$^4$, —C(O)NR$^5$R$^4$, —C(S)NR$^5$R$^4$, —S(O)$_2$NR$^5$R$^4$, —NR$^5$C(O)R$^4$, NR$^5$C(S)R$^4$, —NR$^5$S(O)$_2$R$^4$, —NR$^5$C(O)NH$_2$, —NR$^5$C(O)NR$^5$R$^4$, —NR$^5$C(S)NH$_2$, —NR$^5$C(S)NR$^5$R$^4$, —NR$^5$S(O)$_2$NH$_2$, —NR$^5$S(O)$_2$NR$^5$R$^4$, —S(O)R$^4$, or —S(O)$_2$R$^4$, optionally substituted lower alkynyl, provided, however, that when $R^4$ is optionally substituted lower alkynyl, no alkyne carbon thereof is bound to N, S, O, S(O), S(O)$_2$, C(O) or C(S) of —OR$^4$, —SR$^4$, —NR$^5$R$^4$, —C(O)R$^4$—C(S)R$^4$, —C(O)OR$^4$, —C(O)NR$^5$R$^4$, —C(S)NR$^5$R$^4$, —S(O)$_2$NR$^5$R$^4$, —NR$^5$C(O)R$^4$, —NR$^5$C(S)R$^4$, —NR$^5$S(O)$_2$R$^4$, —NR$^5$C(O)NH$_2$, —NR$^5$C(O)NR$^5$R$^4$, —NR$^5$C(S)NH$_2$, —NR$^5$C(S)NR$^5$R$^4$, —NR$^5$S(O)$_2$NH$_2$, —NR$^5$S(O)$_2$NR$^5$R$^4$, —S(O)R$^4$, or —S(O)$_2$R$^4$, optionally substituted cycloalkyl, optionally substituted heterocycloalkyl, optionally substituted aryl, and optionally substituted heteroaryl;

$R^5$ is selected from the group consisting of hydrogen and optionally substituted lower alkyl; and $R^6$ is optionally substituted heteroaryl, provided, however, the compound is not

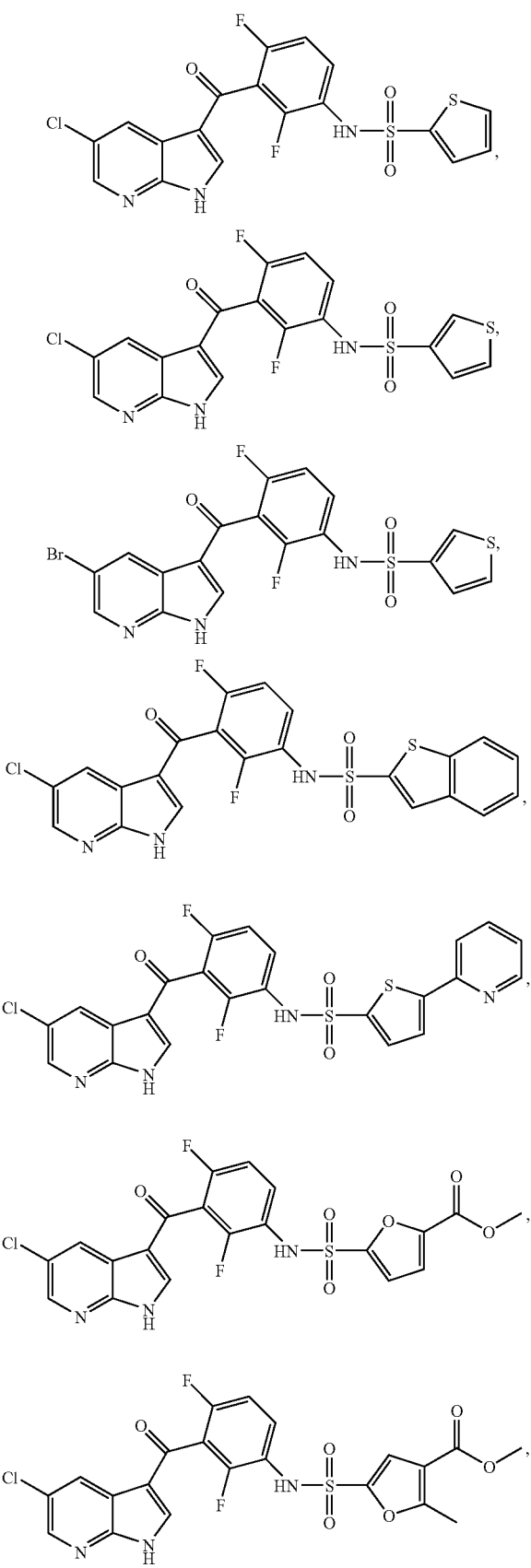

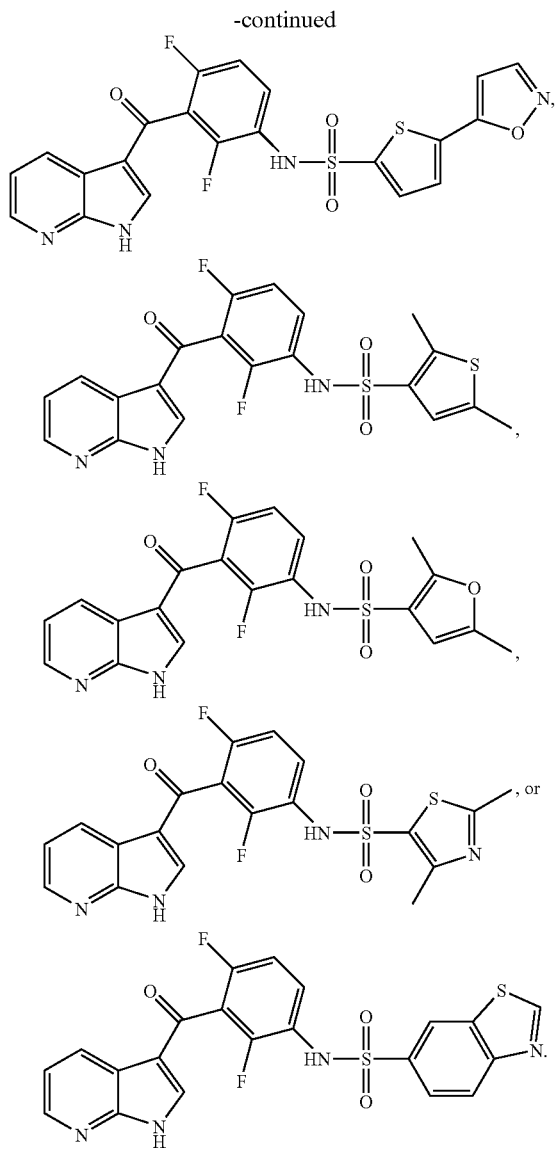

14. The compound of claim 13, wherein:

R¹ is selected from the group consisting of hydrogen, halogen, lower alkyl, lower alkenyl, lower alkynyl, cycloalkyl, heterocycloalkyl, aryl, heteroaryl, —OH, —NH—, —CN, —NO₂, —C(O)OH, —S(O)₂NH₂, —C(O)NH₂, —C(S)NH₂, —NHC(O)NH₂, —NHC(S)NH₂, —NHS(O)₂NH₂, —OR⁷, —SR⁷, —NR⁸R⁷, —C(O)R⁷, —C(S)R⁷, —C(O)OR⁷, —C(O)NR⁸R⁷, —C(S)NR⁸R⁷, —S(O)₂NR⁸R⁷, —NR⁸C(O)R⁷, —NR⁸C(S)R⁷, —NR⁸S(O)₂R⁷, —NR⁸C(O)NH₂, —NR⁸C(O)NR⁸R⁷, —NR⁸C(S)NH₂, —NR⁸C(S)NR⁸R⁷, —NR⁵S(O)₂NH₂, —NR⁸S(O)₂NR⁸R⁷, —S(O)R⁷, and —S(O)₂R⁷, wherein lower alkyl, lower alkenyl or lower alkynyl are optionally substituted with one or more substituents selected from fluoro, —OH, —NH₂, C(O)OH, —C(O)NH₂, —OR⁷, —NR⁸R⁷, —C(O)OR⁷, —C(O)NR⁸R⁷, cycloalkyl, heterocycloalkyl, aryl, and heteroaryl, wherein cycloalkyl, heterocycloalkyl, aryl, and heteroaryl as R¹ or as substituents of lower alkyl, lower alkenyl or lower alkynyl are optionally substituted with one or more substituents selected from the group consisting of —OH, —NH₂, —CN, —NO₂, —S(O)₂NH₂, —C(O)NH₂, —OR⁹, —SR⁹, —NR⁸R⁹, —NR⁸C(O)R⁹, —NR⁸S(O)₂R⁹, —S(O)₂R⁹, —S(O)₂NR⁸R⁹, —C(O)R⁹, —C(O)NR⁸R⁹, halogen, lower alkyl, fluoro substituted lower alkyl, and cycloalkylamino;

R⁶ is heteroaryl optionally substituted with one or more substituents selected from the group consisting of halogen, lower alkyl, cycloalkyl, heterocycloalkyl, aryl, heteroaryl, —OH, —NH₂, —CN, —NO₂, —C(O)OH, —S(O)₂NH₂, —C(O)NH₂, —C(S)NH₂, —NHC(O)NH₂, —NHC(S)NH₂, —NHS(O)₂NH₂, —OR⁷, —SR⁷, —NR⁸R⁷, —C(O)R⁷, —C(S)R⁷, —C(O)OR⁷, —C(O)NR⁸R⁷, —S(O)₂NR⁸R⁷, —NR⁸C(O)R⁷, —NR⁸C(S)R⁷, —NR⁸S(O)₂R⁷, —NR⁸C(O)NH₂, —NR⁸C(O)NR⁸R⁷, —NR⁸C(S)NH₂, —NR⁸C(S)NR⁸R⁷, —NR⁸S(O)₂NH₂, —NR⁸S(O)₂NR⁸R⁷, —S(O)R⁸, and —S(O)₂R⁷, wherein lower alkyl is optionally substituted with one or more substituents selected from fluoro, —OR⁷, —NR⁸R⁷, cycloalkyl, heterocycloalkyl, aryl, and heteroaryl, wherein cycloalkyl, heterocycloalkyl, aryl, and heteroaryl as a substituent of R⁶ or as a substituent of lower alkyl are optionally substituted with one or more substituents selected from the group consisting of —OH, —NH₂, —CN, —NO₂, —S(O)₂NH₂, —C(O)NH₂, —OR⁹, —SR⁹, —NR⁸R⁹, —NR⁸C(O)R⁹, —NR⁸S(O)₂R⁹, —S(O)₂R⁹, —S(O)₂NR⁸R⁹, —C(O)R⁹, —C(O)NR⁹R⁹, halogen, lower alkyl, fluoro substituted lower alkyl, and cycloalkylamino;

R⁷ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R⁷ or as substituents of lower alkyl are optionally substituted with one or more substituents selected from the group consisting of —OH, —NH₂, —CN, —NO₂, —S(O)₂NH₂,—C(O)NH₂, —OR⁹, —SR⁹,—NHR⁹, —NR⁸R⁹, —NR⁸C(O)R⁹, —NR⁸S(O)₂R⁹, —S(O)₂R⁹, —S(O)₂NR⁸R⁹, —C(O)R⁹, —C(O)NR⁸R⁹, halogen, lower alkyl, fluoro substituted lower alkyl, and cycloalkylamino;

R⁸ at each occurrence is independently hydrogen or lower alkyl; and

R⁹ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

15. The compound of claim 14, wherein:

R¹ is selected from the group consisting of hydrogen, —CN, —OR⁷, —SR⁷, —NR⁸R⁷, —NR⁸C(O)R⁷, —NR⁸S(O)₂R⁷, —C(O)NR⁸R⁷, —C(O)R⁷, —S(O)₂NR⁸R⁷, —S(O)R⁷, —S(O)₂R⁷, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^1$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^8$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino; and $R^6$ is heteroaryl optionally substituted with one or more substituents selected from the group consisting of —CN, —OR$^7$, —SR$^7$, —NR$^8$R$^7$, —NR$^8$C(O)R$^7$, —NR$^8$S(O)$_2$R$^7$, —C(O)NR$^8$R$^7$, —C(O)R$^7$, —S(O)$_2$NR$^8$R$^7$, —S(O)R$^7$, —S(O)$_2$R$^7$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as a substituent of $R^6$ or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^9$, —SR$^9$, —NR$^8$R$^9$, —NR$^8$C(O)R$^9$, —NR$^8$S(O)$_2$R$^9$, —S(O)$_2$R$^9$, —S(O)$_2$NR$^8$R$^9$, —C(O)R$^9$, —C(O)NR$^8$R$^9$, halogen, lower alkyl, fluoro substituted lower alkyl, and cycloalkylamino.

16. The compound of claim 15, wherein:

$R^1$ is hydrogen, —CN, —NR$^8$R$^7$, —OR$^7$, —S(O)$_2$R$^7$, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^8$R$^7$, —OR$^7$ and —S(O)$_2$R$^7$, and $R^6$ is heteroaryl optionally substituted with one or more of —CN, fluoro, chloro, lower alkyl, fluoro substituted lower alkyl, —NR$^8$R$^7$, —OR$^7$ or —S(O)$_2$R$^7$.

17. The compound of claim 16, wherein:

$R^1$ is hydrogen, —CN, fluoro, chloro, lower alkyl, fluoro substituted lower alkyl, lower alkoxy, fluoro substituted lower alkoxy, lower alkoxy substituted $C_{2-6}$alkoxy, aryl or heteroaryl, wherein aryl or heteroaryl are optionally substituted with one or more substituents selected from the group consisting of fluoro, chloro, lower alkyl, fluoro substituted lower alkyl, lower alkoxy, fluoro substituted lower alkoxy, mono-alkylamino, di-alkylamino, and cycloalkylamino, and $R^6$ is heteroaryl optionally substituted with one or more of —CN, fluoro, chloro, lower alkyl, fluoro substituted lower alkyl, lower alkoxy, fluoro substituted lower alkoxy, mono-alkylamino, di-alkylamino, or cycloalkylamino.

18. The compound of claim 13, wherein the compound is selected from the group consisting of:

Benzo[b]thiophene-3-sulfonic acid [3-(5-chloro-1H-pyrrolo[2,3-b]pyridine-3-carbonyl)-2,4-difluoro-phenyl]-amide, 5-Methyl-2-trifluoromethyl-furan-3-sulfonic acid [3-(5-chloro-1H-pyrrolo[2,3-b]pyridine-3-carbonyl)-2,4-difluoro-phenyl]-amide, 5—Oxazol-5-yl-thiophene-2-sulfonic acid [3-(5-chloro-1H-pyrrolo[2,3-b]pyridine-3-carbonyl)-2,4-difluoro-phenyl]-amide, 2—Oxo-2H-chromene-6-sulfonic acid [3-(5-chloro-1H-pyrrolo[2,3-b]pyridine-3-carbonyl)-2,4-difluoro-phenyl]-amide, 5-Isoxazol-5-yl-thiophene-2-sulfonic acid [3-(5-chloro-1H-pyrrolo[2,3-b]pyridine-3-carbonyl)-2,4-difluoro-phenyl]-amide, Benzothiazole-6-sulfonic acid [3-(5-chloro-1H-pyrrolo[2,3-b]pyridine-3-carbonyl)-2,4-difluoro-phenyl]-amide, 1-Methyl-3-trifluoromethyl-1H-pyrazole-4-sulfonic acid [3-(5-chloro-1H-pyrrolo[2,3-b]pyridine-3-carbonyl)-2,4-difluoro-phenyl]-amide, Benzo[1,2,5]thiadiazoe-5-sulfonic acid [3-(5-chloro-1H-pyrrolo[2,3-b]pyridine-3-carbonyl)-2,4-difluoro-phenyl]-amide, 5-Methyl-benzo[b]thiophene-2-sulfonic acid [3-(5-chloro-1H-pyrrolo[2,3-b]pyridine-3-carbonyl)-2,4-difluoro-phenyl]-amide, 5-Methyl-thiophene-2-sulfonic acid [3-(5-chloro-1H-pyrrolo[2,3-b]pyridine-3-carbonyl)-2,4-difluoro-phenyl]-amide, 1-Methyl-1-pyrazole-3-sulfonic acid [3-(5-chloro-1H-pyrrolo[2,3-b]pyridine-3-carbonyl)-2,4-difluoro-phenyl]-amide, Pyridine-2-sulfonic acid [2,4-difluoro-3-(5-methoxy-1H-pyrrolo[2,3-b]pyridine-3-carbonyl)-phenyl]-amide; and all salts, tautomers, and isomers thereof.

19. A composition comprising a pharmaceutically acceptable carrier; and a compound according to claim 1.

20. A kit comprising a compound according to claim 1.

21. A composition comprising a pharmaceutically acceptable carrier; and a compound according to claim 7.

22. A kit comprising a compound according to claim 7.

23. A composition comprising: a pharmaceutically acceptable carrier; and a compound according to claim 13.

24. A kit comprising a compound according to claim 13.

* * * * *

UNITED STATES PATENT AND TRADEMARK OFFICE
CERTIFICATE OF CORRECTION

| | | |
|---|---|---|
| PATENT NO. | : 7,863,289 B2 | Page 1 of 1 |
| APPLICATION NO. | : 11/960590 | |
| DATED | : January 4, 2011 | |
| INVENTOR(S) | : Wayne Spevak et al. | |

It is certified that error appears in the above-identified patent and that said Letters Patent is hereby corrected as shown below:

Title Page:

"(73) Assignee: Plexxikon, Inc., Berkeley, CA (US)" should read

--(73) Assignee: Plexxikon Inc., Berkeley, CA (US)--

Signed and Sealed this
Fourth Day of September, 2012

David J. Kappos
*Director of the United States Patent and Trademark Office*